(12) United States Patent
Hess et al.

(10) Patent No.: US 9,987,332 B2
(45) Date of Patent: Jun. 5, 2018

(54) PHARMACEUTICAL COMPOSITION FOR USE IN THE TREATMENT OF A NEURODEGENERATIVE DISEASE

(71) Applicants: SANOFI-AVENTIS DEUTSCHLAND GMBH, Frankfurt am Main (DE); UNIVERSITY OF ULSTER, Coleraine (GB)

(72) Inventors: Sibylle Hess, Frankfurt am Main (DE); Christian Hölscher, Northern Ireland (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days. days.

(21) Appl. No.: 15/146,255

(22) Filed: May 4, 2016

(65) Prior Publication Data

US 2016/0354445 A1    Dec. 8, 2016

Related U.S. Application Data

(63) Continuation of application No. 13/602,913, filed on Sep. 4, 2012, now Pat. No. 9,364,519.

(60) Provisional application No. 61/530,146, filed on Sep. 1, 2011.

(30) Foreign Application Priority Data

Sep. 1, 2011 (EP) .................... 11179784

(51) Int. Cl.
*A61K 38/22* (2006.01)
*A61K 38/26* (2006.01)

(52) U.S. Cl.
CPC .......... *A61K 38/2278* (2013.01); *A61K 38/26* (2013.01)

(58) Field of Classification Search
None
See application file for complete search history.

(56) References Cited

U.S. PATENT DOCUMENTS

| | | | |
|---|---|---|---|
| 3,758,683 A | 9/1973 | Jackson | |
| 3,868,358 A | 2/1975 | Jackson | |
| 4,153,689 A | 5/1979 | Hirai et al. | |
| 4,258,134 A | 3/1981 | Yoshida et al. | |
| 4,367,737 A | 1/1983 | Kozam et al. | |
| 4,608,364 A | 8/1986 | Grau | |
| 4,614,730 A | 9/1986 | Hansen et al. | |
| 4,644,057 A | 2/1987 | Bicker et al. | |
| 4,689,042 A | 8/1987 | Sarnoff et al. | |
| 4,701,440 A | 10/1987 | Grau | |
| 4,731,405 A | 3/1988 | Kirsch et al. | |
| 4,783,441 A | 11/1988 | Thurow | |
| 4,839,341 A | 6/1989 | Massey et al. | |
| 4,863,902 A | 9/1989 | Amagase et al. | |
| 4,885,164 A | 12/1989 | Thurow | |
| 4,923,162 A | 5/1990 | Fleming et al. | |
| 4,959,351 A | 9/1990 | Grau | |
| 4,960,702 A | 10/1990 | Rice et al. | |
| 4,994,439 A | 2/1991 | Longenecker et al. | |
| 5,008,241 A | 4/1991 | Markussen et al. | |
| 5,034,415 A | 7/1991 | Rubin | |
| 5,070,186 A | 12/1991 | Joergensen | |
| 5,101,013 A | 3/1992 | Doerschug et al. | |
| 5,177,058 A | 1/1993 | Doerschug | |
| 5,187,177 A | 2/1993 | Garzaran | |
| 5,227,293 A | 7/1993 | Stengelin et al. | |
| 5,253,785 A | 10/1993 | Haber et al. | |
| 5,272,135 A | 12/1993 | Takruri | |
| 5,358,708 A | 10/1994 | Patel | |
| 5,358,857 A | 10/1994 | Stengelin et al. | |
| 5,370,629 A | 12/1994 | Michel et al. | |
| 5,397,771 A | 3/1995 | Bechgaard et al. | |
| 5,407,609 A | 4/1995 | Tice et al. | |
| 5,424,286 A | 6/1995 | Eng | |
| 5,428,006 A | 6/1995 | Bechgaard et al. | |
| 5,473,049 A | 12/1995 | Obermeier et al. | |
| 5,474,978 A | 12/1995 | Bakaysa et al. | |
| 5,478,323 A | 12/1995 | Westwood et al. | |
| 5,496,924 A | 3/1996 | Habermann et al. | |
| 5,506,203 A | 4/1996 | Baeckstrom et al. | |
| 5,509,905 A | 4/1996 | Michel | |
| 5,514,646 A | 5/1996 | Chance et al. | |
| 5,524,286 A | 6/1996 | Chiesa et al. | |
| 5,534,488 A | 7/1996 | Hoffmann | |
| 5,545,618 A | 8/1996 | Buckley et al. | |
| 5,547,929 A | 8/1996 | Anderson, Jr. et al. | |
| 5,559,094 A | 9/1996 | Brems et al. | |
| 5,595,756 A | 1/1997 | Bally et al. | |
| 5,597,796 A | 1/1997 | Brange | |
| 5,614,219 A | 3/1997 | Wunderlich et al. | |
| 5,614,492 A | 3/1997 | Habener | |

(Continued)

FOREIGN PATENT DOCUMENTS

| | | |
|---|---|---|
| AU | 593274 B2 | 2/1990 |
| AU | 612324 B2 | 7/1991 |
| CA | 1173388 A | 8/1984 |
| CA | 1258427 A | 8/1989 |

(Continued)

OTHER PUBLICATIONS

Cannon et al., "A highly reproducible rotenone model of Parkinson's disease," Neurobiol. Dis. 34:279-290 (2009).*

(Continued)

*Primary Examiner* — Julie Ha
*Assistant Examiner* — Kristina M Hellman
(74) *Attorney, Agent, or Firm* — McDonnell Boehnen Hulbert & Berghoff LLP

(57) ABSTRACT

The present invention refers to a pharmaceutical composition for use in the treatment of a neurodegenerative disease.

17 Claims, 21 Drawing Sheets

(56) References Cited

U.S. PATENT DOCUMENTS

| | | |
|---|---|---|
| 5,631,224 A | 5/1997 | Efendic et al. |
| 5,654,008 A | 8/1997 | Herbert et al. |
| 5,656,722 A | 8/1997 | Doerschug |
| 5,663,291 A | 9/1997 | Obermeier et al. |
| 5,670,360 A | 9/1997 | Thorens |
| 5,693,608 A | 12/1997 | Bechgaard et al. |
| 5,700,662 A | 12/1997 | Chance et al. |
| 5,707,641 A | 1/1998 | Gertner et al. |
| 5,783,556 A | 7/1998 | Clark et al. |
| 5,824,638 A | 10/1998 | Burnside et al. |
| 5,846,747 A | 12/1998 | Thorens et al. |
| 5,846,937 A | 12/1998 | Drucker |
| 5,879,584 A | 3/1999 | Bianchetti |
| 5,948,751 A | 9/1999 | Kimer et al. |
| 5,952,297 A | 9/1999 | De Felippis et al. |
| 5,985,309 A | 11/1999 | Edwards et al. |
| 5,986,048 A | 11/1999 | Rubroder et al. |
| 6,006,753 A | 12/1999 | Efendic |
| 6,034,054 A | 3/2000 | DeFelippis et al. |
| 6,043,214 A | 3/2000 | Jensen et al. |
| 6,051,551 A | 4/2000 | Hughes et al. |
| 6,051,689 A | 4/2000 | Thorens |
| 6,100,376 A | 8/2000 | Doerschug |
| 6,110,703 A | 8/2000 | Egel-Mitani et al. |
| 6,174,856 B1 | 1/2001 | Langballe et al. |
| 6,191,102 B1 | 2/2001 | DiMarchi et al. |
| 6,197,926 B1 | 3/2001 | Guar et al. |
| 6,211,144 B1 | 4/2001 | Havelund |
| 6,227,819 B1 | 5/2001 | Gettel et al. |
| 6,248,363 B1 | 6/2001 | Patel et al. |
| 6,267,981 B1 | 7/2001 | Okamoto et al. |
| 6,268,335 B1 | 7/2001 | Brader |
| 6,268,343 B1 | 7/2001 | Knudsen et al. |
| 6,271,241 B1 | 8/2001 | DeSimone et al. |
| 6,284,725 B1 | 9/2001 | Coolidge et al. |
| 6,309,663 B1 | 10/2001 | Patel et al. |
| 6,310,038 B1 | 10/2001 | Havelund |
| 6,329,336 B1 | 12/2001 | Bridon et al. |
| 6,335,316 B1 | 1/2002 | Hughes et al. |
| 6,344,180 B1 | 2/2002 | Holst et al. |
| 6,358,924 B1 | 3/2002 | Hoffmann |
| 6,384,016 B1 | 5/2002 | Kaarsholm |
| 6,388,053 B1 | 5/2002 | Galloway et al. |
| 6,395,767 B2 | 5/2002 | Robl et al. |
| 6,410,508 B1 | 6/2002 | Isales et al. |
| 6,417,164 B1 | 7/2002 | Kolterman et al. |
| 6,444,641 B1 | 9/2002 | Flora |
| 6,468,959 B1 | 10/2002 | Wunderlich et al. |
| 6,489,292 B1 | 12/2002 | Havelund et al. |
| 6,528,486 B1 | 3/2003 | Larsen et al. |
| 6,734,162 B2 | 5/2004 | Van Antwerp et al. |
| 6,767,887 B1 | 7/2004 | Hoffmann et al. |
| 6,818,738 B2 | 11/2004 | Havelund |
| 6,852,694 B2 | 2/2005 | Van Antwerp et al. |
| 6,875,589 B1 | 4/2005 | Doerschug et al. |
| 6,908,610 B1 | 6/2005 | Sato |
| 6,908,897 B2 | 6/2005 | Brandenburg et al. |
| 6,960,561 B2 | 11/2005 | Boderke |
| 6,969,702 B2 | 11/2005 | Bertilsson et al. |
| 7,022,674 B2 | 4/2006 | DeFelippis et al. |
| 7,115,563 B2 | 10/2006 | Younis et al. |
| 7,119,086 B2 | 10/2006 | Di Malta et al. |
| 7,192,919 B2 | 3/2007 | Tzannis et al. |
| 7,205,276 B2 | 4/2007 | Boderke |
| 7,205,277 B2 | 4/2007 | Boderke |
| 7,238,663 B2 | 7/2007 | DeFelippis et al. |
| 7,405,196 B2 | 7/2008 | Rosskamp et al. |
| 7,476,652 B2 | 1/2009 | Brunner-Schwarz et al. |
| 7,544,656 B2 | 6/2009 | Sabetsky |
| 7,544,657 B2 | 6/2009 | Ebbehoj et al. |
| 7,576,050 B2 | 8/2009 | Greig et al. |
| 7,713,930 B2 | 5/2010 | Brunner-Schwarz et al. |
| 7,803,763 B2 | 9/2010 | Thurow et al. |
| 7,807,242 B2 | 10/2010 | Soerensen et al. |
| 7,918,833 B2 | 4/2011 | Veasey et al. |
| 7,939,293 B2 | 5/2011 | Habermann et al. |
| 7,977,310 B2 | 7/2011 | Rosskamp et al. |
| 8,048,854 B2 | 11/2011 | Habermann et al. |
| 8,084,420 B2 | 12/2011 | Steiner et al. |
| 8,092,421 B2 | 1/2012 | Seiferlein et al. |
| 8,092,422 B2 | 1/2012 | Seiferlein et al. |
| 8,178,495 B2 | 5/2012 | Chilkoti |
| 8,574,214 B2 | 11/2013 | Kuehn et al. |
| 8,633,156 B2 | 1/2014 | Habermann et al. |
| 8,735,349 B2 | 5/2014 | Silvestre et al. |
| 2001/0012829 A1 | 8/2001 | Anderson et al. |
| 2001/0033868 A1 | 10/2001 | Rossling et al. |
| 2001/0039260 A1 | 11/2001 | Havelund |
| 2001/0047084 A1 | 11/2001 | Knudsen et al. |
| 2002/0107265 A1 | 8/2002 | Chen et al. |
| 2002/0132760 A1 | 9/2002 | Van Antwerp et al. |
| 2002/0177151 A1 | 11/2002 | Gimeno |
| 2002/0198140 A1 | 12/2002 | Havelund |
| 2003/0004096 A1 | 1/2003 | Boderke |
| 2003/0026872 A1 | 2/2003 | Dake et al. |
| 2003/0104983 A1 | 6/2003 | DeFelippis et al. |
| 2003/0170691 A1 | 9/2003 | Gimeno et al. |
| 2004/0037893 A1 | 2/2004 | Hansen et al. |
| 2004/0048783 A1 | 3/2004 | Brunner-Schwarz et al. |
| 2004/0092590 A1 | 5/2004 | Arterburn et al. |
| 2004/0097410 A1 | 5/2004 | Zheng et al. |
| 2004/0106547 A1 | 6/2004 | Larsen et al. |
| 2004/0186046 A1 | 9/2004 | Burgess et al. |
| 2004/0229774 A1 | 11/2004 | Rosskamp et al. |
| 2004/0235710 A1 | 11/2004 | DeFelippis et al. |
| 2004/0242853 A1 | 12/2004 | Greig et al. |
| 2005/0014679 A1 | 1/2005 | Beals et al. |
| 2005/0079996 A1 | 4/2005 | Horiguchi et al. |
| 2005/0106147 A1 | 5/2005 | Jordan et al. |
| 2005/0171009 A1 | 8/2005 | Brunner-Schwarz et al. |
| 2005/0209142 A1 | 9/2005 | Bertilsson et al. |
| 2006/0004049 A1 | 1/2006 | Yao et al. |
| 2006/0014678 A1 | 1/2006 | Cowley et al. |
| 2006/0019347 A1 | 1/2006 | Cho et al. |
| 2006/0057137 A1 | 3/2006 | Steiness |
| 2006/0073213 A1 | 4/2006 | Hotamisligil et al. |
| 2006/0093576 A1 | 5/2006 | Chen et al. |
| 2006/0194719 A1 | 8/2006 | Ebbehoj et al. |
| 2006/0239933 A1 | 10/2006 | Nilsson et al. |
| 2006/0287221 A1 | 12/2006 | Knudsen et al. |
| 2007/0027063 A1 | 2/2007 | Boss et al. |
| 2007/0111940 A1 | 5/2007 | Larsen et al. |
| 2007/0128193 A1 | 6/2007 | O'Neil et al. |
| 2007/0135338 A1 | 6/2007 | O'Neil et al. |
| 2007/0155653 A1 | 7/2007 | Boderke |
| 2007/0191271 A1 | 8/2007 | Mayhew et al. |
| 2007/0237827 A1 | 10/2007 | Sung et al. |
| 2008/0064856 A1 | 3/2008 | Warne et al. |
| 2008/0146490 A1 | 6/2008 | Joabsson et al. |
| 2008/0234200 A1 | 9/2008 | Quay et al. |
| 2008/0248999 A1 | 10/2008 | Steiner |
| 2008/0260840 A1 | 10/2008 | Alessi et al. |
| 2008/0267907 A1 | 10/2008 | Poulsen |
| 2009/0082255 A1 | 3/2009 | Brunner-Schwarz et al. |
| 2009/0088369 A1 | 4/2009 | Steiness |
| 2009/0099064 A1 | 4/2009 | Lougheed |
| 2009/0142338 A1 | 6/2009 | Levetan |
| 2009/0175840 A1 | 7/2009 | Kashyap et al. |
| 2009/0176692 A1 | 7/2009 | Habermann et al. |
| 2009/0180953 A1 | 7/2009 | Gotthardt et al. |
| 2009/0186819 A1 | 7/2009 | Carrier et al. |
| 2009/0208565 A1 | 8/2009 | Ebbehoj et al. |
| 2009/0214468 A1 | 8/2009 | Lin et al. |
| 2009/0214657 A1 | 8/2009 | Qazi et al. |
| 2009/0304665 A1 | 12/2009 | Frost et al. |
| 2009/0312236 A1 | 12/2009 | Beals et al. |
| 2009/0324701 A1 | 12/2009 | Williams |
| 2010/0029558 A1 | 2/2010 | Bristow |
| 2010/0055049 A1 | 3/2010 | Kuo et al. |
| 2010/0057194 A1 | 3/2010 | Ryan |
| 2010/0069292 A1 | 3/2010 | Pohl et al. |
| 2010/0069293 A1 | 3/2010 | Bolotin et al. |
| 2010/0227816 A1 | 9/2010 | Flatt et al. |
| 2010/0279931 A1 | 11/2010 | Garibay et al. |

(56) References Cited

U.S. PATENT DOCUMENTS

| | | |
|---|---|---|
| 2010/0311112 A1 | 12/2010 | Rissom et al. |
| 2011/0020294 A1 | 1/2011 | Hammerman |
| 2011/0021423 A1 | 1/2011 | Olsen et al. |
| 2011/0077197 A1 | 3/2011 | Habermann et al. |
| 2011/0118178 A1 | 5/2011 | Silvestre et al. |
| 2011/0118180 A1 | 5/2011 | Silvestre et al. |
| 2011/0144008 A1 | 6/2011 | Larsen et al. |
| 2011/0152185 A1 | 6/2011 | Plum et al. |
| 2011/0173722 A1 | 7/2011 | Habermann et al. |
| 2011/0230402 A1 | 9/2011 | Johansen et al. |
| 2011/0236925 A1 | 9/2011 | Hazra et al. |
| 2011/0245165 A1 | 10/2011 | Larsen et al. |
| 2011/0281790 A1 | 11/2011 | Pohl et al. |
| 2011/0301081 A1 | 12/2011 | Becker et al. |
| 2012/0021978 A1 | 1/2012 | Werner et al. |
| 2012/0121611 A1 | 5/2012 | Lodie et al. |
| 2012/0122774 A1 | 5/2012 | Becker et al. |
| 2012/0183616 A1 | 7/2012 | Sprogoe et al. |
| 2012/0232002 A1 | 9/2012 | Schoettle et al. |
| 2012/0241356 A1 | 9/2012 | Pfenninger et al. |
| 2012/0252724 A1 | 10/2012 | Schoettle et al. |
| 2012/0277147 A1 | 11/2012 | Boka et al. |
| 2012/0283179 A1 | 11/2012 | Brunner-Schwarz et al. |
| 2012/0295846 A1 | 11/2012 | Hagendorf et al. |
| 2012/0316108 A1 | 12/2012 | Chen et al. |
| 2013/0005649 A1 | 1/2013 | Niemoeller et al. |
| 2013/0012433 A1 | 1/2013 | Rosskamp et al. |
| 2013/0023467 A1 | 1/2013 | Silvestre et al. |
| 2013/0040878 A1 | 2/2013 | Silvestre et al. |
| 2013/0065828 A1 | 3/2013 | Ruus et al. |
| 2013/0079279 A1 | 3/2013 | Becker et al. |
| 2013/0085102 A1 | 4/2013 | Silvestre et al. |
| 2013/0096059 A1 | 4/2013 | Stechl et al. |
| 2013/0096060 A1 | 4/2013 | Stechl et al. |
| 2013/0203666 A1 | 8/2013 | Niemoeller et al. |
| 2013/0284912 A1 | 10/2013 | Vogel et al. |
| 2013/0296236 A1 | 11/2013 | Silvestre et al. |
| 2013/0317477 A1 | 11/2013 | Edwards et al. |
| 2014/0148384 A1 | 5/2014 | Boka et al. |
| 2014/0206611 A1 | 7/2014 | Becker et al. |
| 2014/0221285 A1 | 8/2014 | Bley et al. |
| 2014/0248365 A1 | 9/2014 | Rademacher et al. |
| 2014/0371141 A1 | 12/2014 | Souhami et al. |

FOREIGN PATENT DOCUMENTS

| | | |
|---|---|---|
| CA | 1336329 C | 7/1995 |
| CA | 1341203 C | 3/2001 |
| CN | 1276731 A | 12/2000 |
| CN | 1413582 A | 4/2003 |
| CN | 101366692 A | 2/2009 |
| CN | 101444618 A | 6/2009 |
| CN | 101454019 A | 6/2009 |
| CN | 101670096 A | 3/2010 |
| DE | 19637230 A1 | 3/1998 |
| DE | 102008003566 A1 | 7/2009 |
| DE | 102008003568 A1 | 7/2009 |
| DE | 102008053048 A1 | 4/2010 |
| EP | 0018609 B1 | 9/1983 |
| EP | 0046979 B1 | 9/1983 |
| EP | 0132769 A1 | 2/1985 |
| EP | 0140084 A1 | 5/1985 |
| EP | 0166529 A1 | 1/1986 |
| EP | 0200383 A2 | 11/1986 |
| EP | 0211299 A2 | 2/1987 |
| EP | 0214826 A2 | 3/1987 |
| EP | 0224885 A1 | 6/1987 |
| EP | 0227938 A2 | 7/1987 |
| EP | 0229956 A1 | 7/1987 |
| EP | 0229998 A2 | 7/1987 |
| EP | 0254516 A2 | 1/1988 |
| EP | 0305760 A2 | 3/1989 |
| EP | 0368187 A2 | 5/1990 |
| EP | 0375437 A2 | 6/1990 |
| EP | 0383472 A2 | 8/1990 |
| EP | 0194864 B1 | 6/1992 |
| EP | 0419504 B1 | 1/1994 |
| EP | 0600372 A1 | 6/1994 |
| EP | 0668282 A1 | 8/1995 |
| EP | 0668292 A2 | 8/1995 |
| EP | 0678522 A1 | 10/1995 |
| EP | 0837072 A2 | 4/1998 |
| EP | 0845265 A1 | 6/1998 |
| EP | 0885961 A1 | 12/1998 |
| EP | 1076066 A1 | 2/2001 |
| EP | 1172114 A2 | 1/2002 |
| EP | 1222207 A1 | 7/2002 |
| EP | 1523993 A1 | 4/2005 |
| EP | 2112161 A2 | 10/2009 |
| EP | 2324853 A1 | 5/2011 |
| EP | 2329848 A1 | 6/2011 |
| EP | 2389945 A1 | 11/2011 |
| EP | 0921812 B2 | 12/2011 |
| EP | 2387989 B1 | 7/2014 |
| FR | 2456522 A1 | 12/1980 |
| GB | 835638 A | 5/1960 |
| GB | 840870 A | 7/1960 |
| GB | 1527605 A | 10/1978 |
| GB | 1554157 A | 10/1979 |
| JP | S61212598 A | 9/1986 |
| JP | S6399096 A | 4/1988 |
| JP | H02218696 A | 8/1990 |
| JP | H02264798 A | 10/1990 |
| JP | H03504240 A | 9/1991 |
| JP | H06506444 A | 7/1994 |
| JP | 2001521004 A | 11/2001 |
| JP | 2002516880 A | 6/2002 |
| JP | 2006515267 A | 5/2006 |
| JP | 2006137678 A | 6/2006 |
| JP | 2007204498 A | 8/2007 |
| JP | 2009091363 A | 4/2009 |
| JP | 2012255040 A | 12/2012 |
| RU | 2386631 C2 | 4/2010 |
| TW | 157005 B | 5/1991 |
| TW | 562806 B | 11/2003 |
| WO | WO-8300288 A1 | 2/1983 |
| WO | WO-8806599 A1 | 9/1988 |
| WO | WO-8910937 A1 | 11/1989 |
| WO | WO-9007522 A1 | 7/1990 |
| WO | WO-9011299 A1 | 10/1990 |
| WO | WO-9103550 A1 | 3/1991 |
| WO | WO-9116929 A1 | 11/1991 |
| WO | WO-9200321 A1 | 1/1992 |
| WO | WO-9212999 A1 | 8/1992 |
| WO | WO-9318786 A1 | 9/1993 |
| WO | WO-9414461 A1 | 7/1994 |
| WO | WO-9500550 A1 | 1/1995 |
| WO | WO-9524183 A1 | 9/1995 |
| WO | WO-9604307 A1 | 2/1996 |
| WO | WO-9607399 A1 | 3/1996 |
| WO | WO-9611705 A1 | 4/1996 |
| WO | WO-9632414 A1 | 10/1996 |
| WO | WO-9634882 A1 | 11/1996 |
| WO | WO-9641606 A2 | 12/1996 |
| WO | WO-9701331 A2 | 1/1997 |
| WO | WO-9748413 A1 | 12/1997 |
| WO | WO-9805351 A1 | 2/1998 |
| WO | WO-9808531 A1 | 3/1998 |
| WO | WO-9808871 A1 | 3/1998 |
| WO | WO-9808873 A1 | 3/1998 |
| WO | WO-9819698 A1 | 5/1998 |
| WO | WO-9830231 A1 | 7/1998 |
| WO | WO-9835033 A1 | 8/1998 |
| WO | WO-9839022 A1 | 9/1998 |
| WO | WO-9842749 A1 | 10/1998 |
| WO | WO-9856406 A1 | 12/1998 |
| WO | WO-9856418 A1 | 12/1998 |
| WO | WO-9907404 A1 | 2/1999 |
| WO | WO-9921573 A1 | 5/1999 |
| WO | WO-9921578 A1 | 5/1999 |
| WO | WO-9924071 A1 | 5/1999 |
| WO | WO-9925727 A2 | 5/1999 |
| WO | WO-9925728 A1 | 5/1999 |
| WO | WO-9940788 A1 | 8/1999 |

(56) References Cited

FOREIGN PATENT DOCUMENTS

| | | |
|---|---|---|
| WO | WO-9943708 A1 | 9/1999 |
| WO | WO-9946283 A1 | 9/1999 |
| WO | WO-9962558 A1 | 12/1999 |
| WO | WO-0023098 A1 | 4/2000 |
| WO | WO-0023099 A1 | 4/2000 |
| WO | WO-0029013 A1 | 5/2000 |
| WO | WO-0041546 A2 | 7/2000 |
| WO | WO-0066629 A1 | 11/2000 |
| WO | WO-0074736 A1 | 12/2000 |
| WO | WO-0100223 A2 | 1/2001 |
| WO | WO-0102039 A1 | 1/2001 |
| WO | WO-0104156 A1 | 1/2001 |
| WO | WO-0112155 A1 | 2/2001 |
| WO | WO-0121154 A2 | 3/2001 |
| WO | WO 01/24814 | 4/2001 |
| WO | WO-0125278 A1 | 4/2001 |
| WO | WO-0128555 A1 | 4/2001 |
| WO | WO 01/32157 | 5/2001 |
| WO | WO-0137808 A1 | 5/2001 |
| WO | WO-0143762 A2 | 6/2001 |
| WO | WO-0151071 A2 | 7/2001 |
| WO | WO-0152937 A1 | 7/2001 |
| WO | WO-0193837 A2 | 12/2001 |
| WO | WO-0200243 A2 | 1/2002 |
| WO | WO-0224214 A2 | 3/2002 |
| WO | WO-02064115 A1 | 8/2002 |
| WO | WO-02065985 A2 | 8/2002 |
| WO | WO-02066628 A2 | 8/2002 |
| WO | WO-02068660 A1 | 9/2002 |
| WO | WO-02070722 A1 | 9/2002 |
| WO | WO-02076495 A1 | 10/2002 |
| WO | WO-02079250 A1 | 10/2002 |
| WO | WO-03002021 A2 | 1/2003 |
| WO | WO-03020201 A2 | 3/2003 |
| WO | WO-03035028 A1 | 5/2003 |
| WO | WO-03035051 A2 | 5/2003 |
| WO | WO-03044210 A2 | 5/2003 |
| WO | WO-03053339 A2 | 7/2003 |
| WO | WO-03066084 A1 | 8/2003 |
| WO | WO-03094951 A1 | 11/2003 |
| WO | WO-03094956 A1 | 11/2003 |
| WO | WO-03101395 A2 | 12/2003 |
| WO | WO-03105888 A1 | 12/2003 |
| WO | WO-2004005342 A1 | 1/2004 |
| WO | WO-2004035623 A2 | 4/2004 |
| WO | WO-2004045592 A2 | 6/2004 |
| WO | WO-2004064862 A1 | 8/2004 |
| WO | WO-2004078196 A1 | 9/2004 |
| WO | WO-2004078197 A1 | 9/2004 |
| WO | WO-2004078198 A1 | 9/2004 |
| WO | WO-2004080480 A1 | 9/2004 |
| WO | WO-2004096854 A2 | 11/2004 |
| WO | WO-2004105781 A2 | 12/2004 |
| WO | WO-2004107979 A1 | 12/2004 |
| WO | WO-2005021022 A2 | 3/2005 |
| WO | WO-2005023291 A2 | 3/2005 |
| WO | WO-2005028516 A2 | 3/2005 |
| WO | WO-2005046716 A1 | 5/2005 |
| WO | WO 2004/050115 | 6/2005 |
| WO | WO-2005048950 A2 | 6/2005 |
| WO | WO-2005112949 A1 | 12/2005 |
| WO | WO-2005117948 A1 | 12/2005 |
| WO | WO-2006000567 A2 | 1/2006 |
| WO | WO-2006015879 A1 | 2/2006 |
| WO | WO-2006029634 A2 | 3/2006 |
| WO | WO-2006051103 A2 | 5/2006 |
| WO | WO-2006051110 A2 | 5/2006 |
| WO | WO-2006058620 A2 | 6/2006 |
| WO | WO-2006110551 A2 | 10/2006 |
| WO | WO 2007/006307 | 1/2007 |
| WO | WO-2007001150 A2 | 1/2007 |
| WO | WO-2007024700 A2 | 3/2007 |
| WO | WO-2007028394 A2 | 3/2007 |
| WO | WO-2007031187 A1 | 3/2007 |
| WO | WO-2007035665 A1 | 3/2007 |
| WO | WO-2007036299 A2 | 4/2007 |
| WO | WO-2007037607 A1 | 4/2007 |
| WO | WO-2007044867 A2 | 4/2007 |
| WO | WO-2007050656 A2 | 5/2007 |
| WO | WO 2007/081792 | 7/2007 |
| WO | WO-2007075534 A2 | 7/2007 |
| WO | WO-2007081824 A2 | 7/2007 |
| WO | WO-2007082381 A1 | 7/2007 |
| WO | WO-2007095288 A2 | 8/2007 |
| WO | WO-2007104786 A1 | 9/2007 |
| WO | WO-2007109221 A2 | 9/2007 |
| WO | WO-2007113205 A1 | 10/2007 |
| WO | WO-2007120899 A2 | 10/2007 |
| WO | WO-2008006496 A1 | 1/2008 |
| WO | WO-2008013938 A2 | 1/2008 |
| WO | WO 2008/021560 | 2/2008 |
| WO | WO-2008023050 A1 | 2/2008 |
| WO | WO-2008028914 A1 | 3/2008 |
| WO | WO-2008034881 A1 | 3/2008 |
| WO | WO-2008124522 A2 | 10/2008 |
| WO | WO-2008133908 A2 | 11/2008 |
| WO | WO-2008145323 A1 | 12/2008 |
| WO | WO-2009004627 A2 | 1/2009 |
| WO | WO-2009030498 A2 | 3/2009 |
| WO | WO-2009030499 A1 | 3/2009 |
| WO | WO-2009039963 A1 | 4/2009 |
| WO | WO-2009048959 A1 | 4/2009 |
| WO | WO-2009056569 A1 | 5/2009 |
| WO | WO-2009063072 A2 | 5/2009 |
| WO | WO-2009087081 A2 | 7/2009 |
| WO | WO-2009087082 A2 | 7/2009 |
| WO | WO-2009089181 A1 | 7/2009 |
| WO | WO-2009098318 A1 | 8/2009 |
| WO | WO-2009102467 A2 | 8/2009 |
| WO | WO 2009/143014 | 11/2009 |
| WO | WO-2009134380 A2 | 11/2009 |
| WO | WO-2010030670 A2 | 3/2010 |
| WO | WO-2010043566 A2 | 4/2010 |
| WO | WO-2010044867 A1 | 4/2010 |
| WO | WO 2010/089304 | 8/2010 |
| WO | WO-2010092163 A2 | 8/2010 |
| WO | WO 2010/138671 | 12/2010 |
| WO | WO-2011012719 A1 | 2/2011 |
| WO | WO-2011017554 A2 | 2/2011 |
| WO | WO-2011029892 A2 | 3/2011 |
| WO | WO-2011058082 A1 | 5/2011 |
| WO | WO-2011058083 A1 | 5/2011 |
| WO | WO-2011089203 A1 | 7/2011 |
| WO | WO-2011103575 A1 | 8/2011 |
| WO | WO-2011122921 A2 | 10/2011 |
| WO | WO-2011128374 A1 | 10/2011 |
| WO | WO-2011144673 A2 | 11/2011 |
| WO | WO-2011144674 A2 | 11/2011 |
| WO | WO-2011147980 A1 | 12/2011 |
| WO | WO-2011157402 A1 | 12/2011 |
| WO | WO-2011160066 A1 | 12/2011 |
| WO | WO-2012012352 A2 | 1/2012 |
| WO | WO-2012028172 A1 | 3/2012 |
| WO | WO-2012055967 A2 | 5/2012 |
| WO | WO-2012065996 A1 | 5/2012 |
| WO | WO-2012066086 A1 | 5/2012 |
| WO | WO-2012080320 A1 | 6/2012 |
| WO | WO-2012104342 A1 | 8/2012 |
| WO | WO-2012125569 A2 | 9/2012 |
| WO | WO-2012156296 A1 | 11/2012 |
| WO | WO-2012156299 A1 | 11/2012 |
| WO | WO-2012177929 A2 | 12/2012 |
| WO | WO-2013060850 A1 | 5/2013 |
| WO | WO-2014017849 A1 | 1/2014 |
| WO | WO-2014118355 A1 | 8/2014 |
| WO | WO 2014/202483 | 12/2014 |
| WO | WO 2015/059302 | 4/2015 |

OTHER PUBLICATIONS

18th World Health Congress (Helsinki). WMA Declaration of Helsinki—Ethical Principles for Medical Research Involving Human Subjects; WMA; Jun. 1964, pp. 1-8.

(56) References Cited

OTHER PUBLICATIONS

Abbas et al., "Impairment of Synaptic Plasticity and Memory formation in GLP-1 Receptor Ko Mice: Interaction Between Type 2 Diabetes and Alzheimer's Disease," Behavioural Brain Research, 2009, vol. 205 (1), pp. 265-271.
Action to Control Cardiovascular Risk in Diabetes Study Group, "Effects of Intensive Glucose Lowering in Type 2 Diabetes," The New England Journal of Medicine, 2008, vol. 358 (24), pp. 2545-2559.
Actrapid® prescribing information, Apr. 2011, pp. 1-4.
Actrapid® summary of product characteristics, Apr. 2011, pp. 1-11.
Aderinwale O.G., et al., "Current Therapies and New Strategies for the Management of Alzheimer's Disease," American Journal of Alzheimer's Disease and Other Dementias, 2010, vol. 25 (5), pp. 414-424.
Agholme L., et al., "An in Vitro Model for Neuroscience: Differentiation of SH-SY5Y Cells into Cells with Morphological and Biochemical Characteristics of Mature Neurons," Journal of Alzheimer's Disease, 2010, vol. 20, pp. 1069-1082.
Ahren et al., Abstract "Efficacy and Safety of Lixisenatide QD Morning and Evening Injections vs Placebo in T2DM Inadequately Controlled on Metformin (GetGoal-M)" Oral presentation O-0591 presented at the World Diabetes Congress in Dubai, Dec. 5-8, 2011, one page.
Akbar D.H., "Sub-Optimal Postprandial Blood Glucose Level in Diabetics Attending the Outpatient Clinic of a University Hospital," Saudi Med Journal, Oct. 2003, vol. 24 (10), pp. 1109-1112.
American Diabetes Association (ADA) Committee Report—The Expert Committee on the Diagnosis and Classification of Diabetes Mellitus—Report of the Expert Committee on the Diagnosis and Classification of Diabetes Mellitus, Diabetes Care, 21(Supplement 1): S5-S19 (Jan. 1998).
Aoki K., et al., "Hydrolysis of Nonionic Surfactants," Annual Report Takeda Research Laboratory, 1968, vol. 27, pp. 172-176.
Apidra® prescribing information, Apr. 2012, pp. 1-6.
Arnolds et al., "Insulin Glargine (GLAR) plus Metformin (MET): An Efficacious and Safe Regimen that can be combined with Exenatide (EXE) or Sitagliptin (SITA)" Diabetes, 58(Suppl. 1): A141, Jun. 2009.
Arnolds S., et al., "Basal Insulin Glargine Vs Prandial Insulin Lispro in Type 2 Diabetes," Lancet, 2008, vol. 378 (9636), pp. 370-371.
Arnolds S., et al., "Further Improvement in Postprandial Glucose Control with Addition of Exenatide or Sitagliptin to Combination therapy with Insulin Glargine and Metformin—A Proof-of-Concept Study," Diabetes Care, 2010, vol. 33 (7), pp. 1509-1515.
Auerbach R., et al., "Angiogenesis Assays: Problems and Pitfalls," Cancer Metastasis Reviews, 2000, vol. 19 (1-2), pp. 167-172.
Bakaysa D.L., et al., "Physicochemical Basis for the Rapid Time-Action of Lys$^{b28}$ Pro$^{b29}$-Insulin: Dissociation of a Protein-Ligand Complex," Protein science, 1996, vol. 5 (12), pp. 2521-2531.
Banks W.A., et al., "Brain Uptake of the Glucagon-Like Peptide-1 Antagonist Exendin(9-39) After intranasal Administration," The Journal of Pharmacology and Experimental Therapeutics, 2004, vol. 309 (2), pp. 469-475.
Barnett A., "Dosing of Insulin Glargine in the Treatment of Type 2 Diabetes," Clinical Therapeutics, Jun. 2007, vol. 29 (6), pp. 987-999.
Barnett A.H., et al., "Tolerability and Efficacy of Exenatide and Titrated Insulin Glargine in Adult Patients with Type 2 Diabetes Previously Uncontrolled with Metformin or a Sulfonylurea: A Multinational, Randomized, Open-Label, Two-Period, Crossover Noninferiority Trial," Clinical Therapeutics, Nov. 2007, vol. 29 (11), pp. 2333-2348.
Barnett A.H., "Insulin Glargine in the Treatment of Type 1 and Type 2 Diabetes," Vascular Health and Risk Management, Published Jan. 25, 2006, vol. 2 (1), pp. 59-67.
Barnett A.H., "Lixisenatide: Evidence for its Potential Use in the Treatment of Type 2 Diabetes," Core Evidence, Published Online Sep. 8, 2011, vol. 6, pp. 67-79.

Barnett R.O., et al., "Insulin Analogues," Lancet, 1997, vol. 349 (9044), pp. 47-51.
Behar J., et al., "Functional Gallbladder and Sphincter of Oddi Disorders," Gastroenterology, 2006, vol. 130 (5), pp. 1498-1509.
Beintema J.J., et al., "Molecular Evolution of Rodent Insulins," Molecular Biology and Evolution, 1987, vol. 4 (1), pp. 10-18.
Berger M., "Towards More Physiological Insulin Therapy in the 1990s a Comment," Diabetes Research and Clinical Practice, May 1989, vol. 6 (4), pp. S25-S31.
Berlie H., et al., "Glucagon-Like Peptide-1 Receptor Agonists as Add-On therapy to Basal Insulin in Patients with Type 2 Diabetes: A Systematic Review," Diabetes, Metabolic Syndrome and Obesity: Targets and Therapy, 2012, vol. 5, pp. 165-174.
Berlinsulin® H prescribing information, Apr. 2012, pp. 1-4.
Berlinsulin® H summary of product characteristics, Apr. 2012, pp. 1-11.
Bertram L., et al., "The Genetics of Alzheimer Disease: Back to the Future," Neuron, 2010, vol. 68 (2), pp. 270-281.
Best, Mathmatics and Statistics pp. 1-39, 1988.
Bethel M.A., et al., "Basal Insulin Therapy in Type 2 Diabetes," The Journal of the American Board of the Family Practice, May-Jun. 2005, vol. 18 (3), pp. 199-204.
Bhatt N.P., et al., "Chemical Pathways of Peptide Degradation. I. Deamidation of Adrenocorticotropic Hormone," Pharmaceutical Research, 1990, vol. 7 (6), pp. 593-599.
Blanchard V., et al., "Time Sequence of Maturation of Dystrophic Neurites Associated with Abeta Deposits in APP/PS1 Transgenic Mice," Experimental Neurology, 2003, vol. 184, pp. 247-263.
Bland J.M., et al., "Measurement Error," British Medical Journal, Jun. 29, 1996, vol. 312 (7047), pp. 1654.
Bolen et al., "Systematic Review: Comparative Effectiveness and Safety of oral Medications for Type 2 Diabetes Mellitus," Annals of Internal Medicine, Epub Jul. 16, 2007, vol. 147 (6), pp. 386-399.
Bolli et al., "Efficacy and safety of lixisenatide once-daily versus placebo in patients with type 2 diabetes mellitus insufficiently controlled on metformin (GetGoal-F1)." Presentation Abstract No. 784, EASD Meeting Sep. 12-16, 2014.
Bolli G.B., et al., "Efficacy and Safety of Lixisenatide once Daily Vs Placebo in People with Type 2 Diabetes Insufficiently Controlled on Metformin (Getgoal-F1)," Diabetic Medicine, Published Online Oct. 24, 2014, vol. 31 (2), pp. 176-184.
Bolli G.B., "The Pharmacokinetic Basis of Insulin Therapy in Diabetes Mellitus," Diabetes Research and Clinical Practice, May 1989, vol. 6 (4), pp. S3-S15.
Boutajangout A., et al., "Characterisation of Cytoskeletal Abnormalities in Mice Transgenic for Wild-Type Human Tau and Familial Alzheimer's Disease Mutants of APP and Presenilin-1," Neurobiology of Disease, 2004, vol. 15 (1), pp. 47-60.
Boutajangout A., et al., "Increased Tau Phosphorylation But Absence of formation of Neurofibrillary Tangles in Mice Double Transgenic for Human Tau and Alzheimer Mutant (M146L) Presenilin-1," Neuroscience Letters, 2002, vol. 318 (1), pp. 29-33.
Brange & Langkjaer, "Insulin Structure and Stability," Pharmaceutical Biotechnology,Chapter 11, 1993, vol. 5, pp. 315-350.
Brange "Galenics of Insulin" 1987, p. 35-36.
Brange J., et al., "Chemical Stability of Insulin 3. Influence of Excipients, formulation, and Ph," Acta Pharmaceutica Nordica, 1992, vol. 4 (3), pp. 149-158.
Brange J., et al., "Design of Insulin Analogues for Meal-Related therapy," Journal of Diabetes and Its Complications, 1993, vol. 7 (2), pp. 106-112. Abstract only submitted.
Brange J., et al., "Monomeric Insulins and their Experimental and Clinical Implications," Diabetes Care, Sep. 1990, vol. 13 (9), pp. 923-954.
Brange J., et al., "Neutral Insulin Solutions Physically Stabilized by Addition of Zn2+," Diabetic Medicine, Nov.-Dec. 1986, vol. 3, pp. 532-536.
Brange J., et al., "Toward Understanding Insulin Fibrillation," Journal of Pharmaceutical Sciences, 1997, vol. 86 (5), pp. 517-525.
Brod M., et al., "Adherence Patterns in Patients with Type 2 Diabetes on Basal Insulin Analogues: Missed, Mistimed and Reduced Doses," Current Medical Research and Opinion, 2012, vol. 28 (12), pp. 1933-1946.

(56) References Cited

OTHER PUBLICATIONS

Brod M., et al., "Examining Correlates of Treatment Satisfaction for injectable Insulin in Type 2 Diabetes: Lessons Learned from a Clinical Trial Comparing Biphasic and Basal Analogues," Health Quality of Life Outcomes, 2007, vol. 5, pp. 1-10.

Broderick J., et al., "Guidelines for the Management of Spontaneous intracerebral Hemorrhage in Adults," Circulation, 2007, vol. 116 (16), pp. e391-e413.

Brown J.B., et al., "Slow Response to Loss of Glycemic Control in Type 2 Diabetes Mellitus," American Journal of Managed Care, 2003, vol. 9 (3), pp. 213-217.

"Buffer" Oxford Dictionary of Biochemistry and Molecular Biology, Oxford University Press, 2001, p. 83.

Burgermeister W., et al., "The Isolation of Insuin from the Pancreas," Insulin, 1975, vol. Part 2, pp. 715-727.

Burke G.T., et al., "Nature of the B10 Amino Acid Residue Requirements for High Biological Activity of Insulin," International Journal of Peptide and Protein Research, 1984, vol. 23 (4), pp. 394-401.

Buse J.B., et al., "Use of Twice-Daily Exenatide in Basal Insulin-Treated Patients with Type 2 Diabetes: A Randomized, Controlled Trial," Annals of Internal Medicine, Jan. 2011, vol. 154 (2), pp. 103-112.

Byetta—Summary of Product Characteristics, updated Jan. 27, 2015, last accessed Apr. 18, 2015, pp. 1-12.

Byrne M.M., et al., "Inhibitory Effects of Hyperglycaemia on Fed Jejunal Motility: Potential Role of Hyperinsulinaemia," European Journal of Clinical Investigation, 1998, vol. 28 (1), pp. 72-78.

Cadario B., "SITAGLIPTIN," Drug Information Perspectives, 2010, vol. 30 (4), pp. 1-6.

Campas C., et al., "Ave-0010 GLP-1 Receptor Agonist Treatment of Diabetes," Drugs of the Future, Oct. 2008, vol. 33 (10), pp. 838-840.

Campbell R.K., et al., "Insulin Glargine," Clinical Therapeutics, 2001, vol. 23 (12), pp. 1938-1957.

Casas C., et al., "Massive CA1/2 Neuronal Loss with Intraneuronal and N-Terminal Truncated Abeta42 Accumulation in a Novel Alzheimer Transgenic Model," American Journal of Pathology, 2004, vol. 165 (4), pp. 1289-1300.

Chancel, "Natixis Conference on Diabetes." Sanofi, Paris, pp. 1-23 (Nov. 8, 2011).

Charles M.A., et al., "Prevention of Type 2 Diabetes: Role of Metformin," Drugs, Sep. 1999, vol. 58 (Suppl 1), pp. 71-73.

Chatterjee S., et al., "Insulin Glargine and its Place in the Treatment of Types 1 and 2 Diabetes Mellitus," Expert Opinion on Pharmacotherapy, 2006, vol. 7 (10), pp. 1357-1371.

Chen Y.E., et al., "Tissue-Specific Expression of Unique mRNAs That Encode Proglucagon-Derived Peptides or Exendin 4 in the Lizard," The Journal of Biological Chemistry, 1997, vol. 272 (7), pp. 4108-4115.

Cheung Y.T., et al., "Effects of All-Trans-Retinoic Acid on Human SH-SY5Y Neuroblastoma as in Vitro Model in Neurotoxicity Research," Neurotoxicology, 2009, vol. 30 (1), pp. 127-135.

Childs B.P., et al., "Defining and Reporting Hypoglycemia in Diabetes: A Report from the American Diabetes Association Workgroup on Hypoglycemia," Diabetes Care, May 2005, vol. 28 (5), pp. 1245-1249.

Cholangiocarcinoma, Johns Hopkins Medicine Webstite, https://gi.jhsps.org/GDLDisease.aspx?CurrentUDV=31&GDLCat_ID=AF793A59-B736-42CB-9E1FE79D2B9FC358&GDL_Disease_ID=A6D1OE80-887D-49A7-B3BB-0517D38CE757, accessed on May 14, 2014, pp. 1-12.

Christensen M., et al., "Lixisenatide, a Novel GLP-1 Receptor Agonist for the Treatment of Type 2 Diabetes Mellitus," IDrugs: The Investigational Drugs Journal, Aug. 2009, vol. 12 (8), pp. 503-513.

Christensen M., et al., "Lixisenatide for Type 2 Diabetes Mellitus," Expert Opinion on Investigational Drugs, Epub Mar. 11, 2011, vol. 20 (4), pp. 549-557.

Cochran E., et al., "The Use of U-500 in Patients with Extreme Insulin Resistance," Diabetes Care, 2005, vol. 28 (5), pp. 1240-1244.

Colclough et al., Abstract "Levels of FPG and HbA1c Control and the Relationship to BMI in T2D Patients Treated with Basal Insulin and OAD Therapy." Abstract 2416-PO; Presented at the 72nd Scientific Session at the American Diabetes Association Meeting, 2012, A609, one page.

Colino E., et al., "Therapy with Insulin Glargine (Lantus) in toddlers, Children and Adolescents with Type 1 Diabetes," Diabetes Research and Clinical Practice, 2005, vol. 70 (1), pp. 1-7.

Community register of medicinal products for human use, Chemical Subgroup A10BX, "Lyxumia" European Commision—Public Health, p. 1-2 (May 2, 2013).

Correa, "Pautas para el examen de patentes farmaceuticas. Una perspectiva desde la Salud Publica. Documento de Trabajo" Universidad de Buenos Aires, Mar. 2008, see English on pp. 19-20, pp. 1-66.

Craig et al., "ISPAD Clinical Practice Consensus Guidelines 2014 Compendium—Definition, epidemiology, and classification of diabetes in children and adolescents." Pediatric Diabetes, 15(Suppl. 20):4-17 (2014).

Crapo P.A., et al., "Postprandial Plasma-Glucose and -Insulin Responses to Different Complex Carbohydrates," Diabetes, Dec. 1977, vol. 26 (12), pp. 1178-1183.

Croom K.F., et al., "Liraglutide a Review of its Use in Type 2 Diabetes Mellitus," Drugs, 2009, vol. 69 (14), pp. 1985-2004.

Cryer P.E., "Hypoglycemia Is the Limiting Factor in the Management of Diabetes," Diabetes/Metabolism Research and Reviews, Jan.-Feb. 1999, vol. 15 (1), pp. 42-46.

Cvetkovic R.S., et al., "Exenatide a Review of its Use in Patients with Type 2 Diabetes Mellitus (As an Adjunct to Metformin and/or a Sulfonylurea)," Drugs, 2007, vol. 67 (6), pp. 935-954.

Czech C., et al., "Proteolytical Processing of Mutated Human Amyloid Precursor Protein in Transgenic Mice," Brain Research Molecular Brain Research, 1997, vol. 47 (1-2), pp. 108-116.

D'Alessio D., "GLP-1 Receptor Agonists: Strategies for PPG Control," Medical Nursing Education,vol. 3, pp. 1-26 (Jan. 2010).

D'Alessio D.A., et al., "Glucagon-Like Peptide 1 Enhances Glucose tolerance both by Stimulation of Insulin Release and by increasing Insulin-Independent Glucose Disposal," Journal of Clinical Investigation, 1994, vol. 93 (5), pp. 2263-2266.

Database, ADISCTI, "A randomized, 4-sequence, cross-over, double bind, dose response study of 0.4, 0.6 and 0.09 U/kg insluin glarine U300 compared to 0.4 U/kg Lantus U100 in patients with diabetes mellitus type I using euglycemic clamp technique" last updated Dec. 16, 2010, pp. 1-4.

Davis How to Convert mg to mmol/L, available online at http://www.ehow.com/how_8498850_convert mg-mmoll.html (accessed on Nov. 11, 2015).

De Arriba S.G., et al., "Carbonyl Stress and Nmda Receptor Activation Contribute to Methylglyoxal Neurotoxicity," Free Radical Biology and Medicine, 2006, vol. 40 (5), pp. 779-790.

De La Pena A., et al., "Pharmacokinetics and Pharmacodynamics of High-Dose Human Regular U-500 Insulin Versus Human Regular U-100 Insulin in Healthy Obese Subjects," Diabetes Care, 2011, vol. 34 (12), pp. 2496-2501.

De Rosa R., et al., "Intranasal Administration of Nerve Growth Factor (Ngf) Rescues Recognition Memory Deficits in Ad11 Anti-Ngf Transgenic Mice," Proceedings of the National Academy of Sciences of the United States of America, 2005, vol. 102 (10), pp. 3811-3816.

Deacon C.F., et al., "Dipeptidyl Peptidase IV inhibition Potentiates the Insulinotropic Effect of Glucagon-Like Peptide 1 in the Anesthetized Pig," Diabetes, 1998, vol. 47 (5), pp. 764-769.

Deacon C.F., et al., "Dipeptidyl Peptidase IV Resistant Analogues of Glucagon-Like Peptide-1 Which have Extended Metabolic Stability and Improved Biological Activity," Diabetologia, 1998, vol. 41 (3), pp. 271-278.

Definition of indication, Merriam-Webster online, accessed Oct. 22, 2015, 2 pages.

Definition of palliative, http://medicaldictionary.thefreedictionary.com/, accessed on Nov. 6, 2014, pp. 1-2.

(56) References Cited

OTHER PUBLICATIONS

Definition of sphincter of pancreatic duct in the Medical Dictionary, http://medicaldictionary.thefreedictionary.com/, accessed on May 22, 2014, pp. 1-2.

Defronzo R.A., et al., "Effects of Exenatide (Exendin-4) on Glycemic Control and Weight Over 30 Weeks in Metformin-Treated Patients with Type 2 Diabetes," Diabetes care, May 2005, vol. 28 (5), pp. 1092-1100.

Defronzo R.A., "Pathogenesis of Type 2 Diabetes: Implications for Metformin," Drugs, Sep. 1999, vol. 58 (Suppl 1), pp. 29-30.

Defronzo R.A., "Pharmacologic therapy for Type 2 Diabetes Mellitus," Annals of Internal Medicine, 1999, vol. 131 (4), pp. 281-303.

Delatour B., et al., "Alzheimer Pathology Disorganizes Cortico-Cortical Circuitry: Direct Evidence from a Transgenic Animal Model," Neurobiology of Disease, 2004, vol. 16 (1), pp. 41-47.

Devries J.H., et al., "Sequential intensification of Metformin Treatment in Type 2 Diabetes with Liraglutide Followed by Randomized Addition of Basal Insulin Prompted by A1C Targets," Diabetes Care, 2012, vol. 35 (7), pp. 1446-1454.

Dewitt D.E., "Case Study: Treating New on-Set Catabolic Type 2 Diabetes with Glargine and Lispro," Clinical Diabetes, Oct. 2006, vol. 24 (4), pp. 180-181.

Diabetes Prevention Program Research Group, "Reduction in the incidence of Type 2 Diabetes with Lifestyle intervention or Metformin," The New England Journal of Medicine, 2002, vol. 346 (6), pp. 393-403.

Distiller et al., Poster: "Pharmacokinetics and Pharmacodynamics of a New GLP-1 Agonist AVE0010 in Type 2 Diabetes Patients" Meeting: 68th Scientific Sessions (Jun. 2008) Poster No. 520-P.

Dixon G.H., et al., "Regeneration of Insulin Activity from the Separated and inactive A and B Chains," Nature, 1960, vol. 188 (4752), pp. 721-724.

Donelli G., et al., "Plastic Biliary Stent Occlusion: Factors Involved and Possible Preventive Approaches," Clinical Medicine & Research, 2007, vol. 5 (1), pp. 53-60.

Dormandy J.A., et al., "Secondary Prevention of Macrovascular Events in Patients with Type 2 Diabetes in the Proactive Study (Prospective Pioglitazone Clinical Trial in Macrovascular Events): A Randomised Controlled Trial," Lancet, Oct. 8, 2005, vol. 366 (9493), pp. 1279-1289.

Doyle M.E. et al., "Mechanisms of Action of Glucagon-Like Peptide 1 in the Pancreas," Pharmacology & Therapeutics, Mar. 2007, vol. 113 (3), pp. 546-593.

Drucker D.J. et al., "The incretin System: Glucagon-Like Peptide-1 Receptor Agonists and Dipeptidyl Peptidase-4 inhibitors in Type 2 Diabetes," Lancet, Nov. 11, 2006, vol. 368 (9548), pp. 1696-1705.

Drucker D.J., "Glucagon-Like Peptides," Diabetes, 1998, vol. 47 (2), pp. 159-169.

Drucker D.J., "Mini Review: The Glucagon-Like Peptides," Endocrinology, 2001, vol. 142 (2), pp. 521-527.

Drucker D.J., "The Biology of Lncretin Hormones," Cell Metabolism, 2006, vol. 3 (3), pp. 153-165.

DrugBank, "Insulin glargine," available online at http://www.drugbank.ca/drugs/DB00047, 16 pages (accessed online Sep. 25, 2014).

Drury P.L., et al., "Diabetic Nephropathy," British Medical Bulletin, 1989, vol. 45 (1), pp. 127-147.

Dubois B., et al., "Revising the Definition of Alzheimer's Disease: A New Lexicon," Lancet Neurology, 2010, vol. 9 (11), pp. 1118-1127.

Dunn C.J., et al., "Insulin Glargine: An Updated Review of its Use in the Management of Diabetes Mellitus," Drugs, 2003, vol. 63 (16), pp. 1743-1778.

During M.J., et al., "Glucagon-Like Peptide-1 Receptor is involved in Learning and Neuroprotection," Nature Medicine, 2003, vol. 9 (9), pp. 1173-1179.

Eckert A., et al., "Alzheimer's Disease-Like Alterations in Peripheral Cells from Presenilin-1 Transgenic Mice," Neurobiology of Disease, 2001, vol. 8 (2), pp. 331-342.

EFC10780 (Sanofi study), "A randomized, double-blind, double-dummy, 2-arm parallel-group, multicenter 24-week study comparing the efficacy and safety of AVE0010 to sitagliptin as add-on to metformin in obese type 2 diabetic patients younger than 50 and not adequately controlled with metformin (EFC10780)" p. 1-4 (Jan. 29, 2014).

EFC10781 Clinical Trials, "24-week Treatment With Lixisenatide in Type 2 Diabetes Insufficiently Controlled With Metformin and Insulin Glargine" ClinicalTrials.gov; EFC10781 pp. 1-5 (Sep. 2009).

EFC6017; Clinical Trial Eudra CT No. 2007-005884-92, accessed Apr. 24, 2015, one page.

EFC6018; Clinical trial EudraCT 2007-005887-29, "GETGOAL-MONO" accessed Jul. 27, 2014; pp. 1-16.

EMA—Science Medicines Health "TOUJEO" EPAR Summary for the Public, first published Nov. 5, 2009, pp. 1-3.

EMA Press Release, "European Medicines Agency recommends suspension of Avandia, Avandamet and Avaglim" pp. 1-2 (Sep. 23, 2010).

Eng J., et al., "Isolation and Characterization of Exendin-4, An Exendin-3 Analogue, from Heloderma Suspectum Venom Further Evidence for an Exendin Receptor on Dispersed Acini from Guinea Pig Pancreas," The Journal of Biological Chemistry, 1992, vol. 267 (11), pp. 7402-7405.

English translation of Search Report for Chinese Patent Application No. 201280053404.6; dated Feb. 10, 2015, pp. 1-3.

English translation of Search Report for Chinese Patent Application No. 20140220537.9; dated Feb. 13, 2015, pp. 1-2.

English translation of the TIPO Search Report for ROC Patent Application No. 104116749, dated Feb. 22, 2016, One page.

English translation of the TIPO Search Report for ROC Patent Application No. 101131466; dated Mar. 2, 2016, one page.

European Medicines Agency—Science Medicines Health, "Guideline on clinical investigation of medicinal products in the treatment of diabetes mellitus" Committee for Medicinal Products for Human Use, Jan. 20, 2010, pp. 1-19.

*Ex Parte Herrmann*, Appeal No. 2009-001777 U.S. Appl. No. 10/616,457 (B. Pai. Nov. 13, 2009).

Executive Summary, "Standards of Medical Care in Diabetes—2009" Diabetes Care,32(Suppl. 1):S6-S12 (Jan. 2009).

Extended European Search Report for Euorpean Application No. 98 11 0889.7; dated Oct. 14, 1998, pp. 1-4.

Extended European Search Report for European Application No. 09 17 5876.3; dated Mar. 24, 2010, pp. 1-4.

Extended European Search Report for European Application No. 09 17 5877.1; dated Apr. 29, 2010, pp. 1-5.

Extended European Search Report for European Application No. 10 16 4368.2; dated Oct. 14, 2010, pp. 1-6.

Extended European Search Report for European Application No. 10 30 5780; dated Nov. 16, 2010, pp. 1-3.

Extended European Search Report for European Application No. 11 15 3106; dated Jul. 6, 2011, pp. 1-12.

Extended European Search Report for European Application No. 11 16 0270.2; dated Sep. 19, 2011, pp. 1-8.

Extended European Search Report for European Application No. 11 16 6415; dated Mar. 12, 2012, pp. 1-12.

Extended European Search Report for European Application No. 11 17 9149.7; dated Feb. 9, 2012, pp. 1-8.

Extended European Search Report for European Application No. 13 305 126; dated Apr. 11, 2013, pp. 1-7.

Extended European Search Report for European Application No. 13 305 432.0; dated Sep. 13, 2013, pp. 1-5.

Extended European Search Report for European Application No. 14 16 6877.2; of Aug. 18, 2014, pp. 1-6.

Extended European Search Report for European Application No. 14 19 7154.9: dated Apr. 8, 2015, pp. 1-7.

Fabunmi R., et al., "Patient Characteristics, Drug Adherence Patterns, and Hypoglycemia Costs for Patients with Type 2 Diabetes Mellitus Newly initiated on Exenatide or Insulin Glargine," Current Medical Research and Opinion, 2009, vol. 25 (3), pp. 777-786.

Faivre E., et al., "Effects of Gip Analogues in Neuronal Signalling, Cell Proliferation and Learning and Memory," Regulatory Peptides, Aug. 2010, vol. 164 (1), pp. 40-41.

(56) References Cited

OTHER PUBLICATIONS

FDA Frequently Asked Questions about Combination Products;accessed from www.fda.gov/CombinationProducts/AboutCombinationProducts/usm101496.1/htm, 2009 downloaded Jul. 13, 2012, pp. 1-18.
FDA Guidance for Industry, US Department of Health and Human Services, Food and Drug Administration, Center for Drug Evaluation and Research (CDER), pp. 1-11, Feb. 2014.
FDA label of Apidra®, May 2014, pp. 1-35.
FDA label of Humalog®, Mar. 2013, pp. 1-27.
FDA label of Lantus®, Oct. 2013, pp. 1-44.
Feinglos M.N., et al., "Effects of Liraglutide (Nn2211), A Long-Acting GLP-1 Analogue, on Glycaemic Control and Bodyweight in Subjects with Type 2 Diabetes," Diabetic Medicine, Jul. 2005, vol. 22 (8), pp. 1016-1023.
Fieller E.C., "Symposium on Interval Estimation; Some Problems with Interval Estimation," Journal of the Royal Statistical Society, 1954, vol. 16 (2), pp. 175-185.
Final Office Action from U.S. Appl. No. 12/617,805; dated Feb. 11, 2013, pp. 1-13.
Final Office Action from U.S. Appl. No. 12/617,805; dated Jan. 12, 2012, pp. 1-14.
Final Office Action from U.S. Appl. No. 12/617,805; dated Jan. 13, 2015, pp. 1-11.
Final Office Action issued in U.S. Appl. No. 13/123,835; dated Feb. 12, 2013, pp. 1-13.
Final Rejection in U.S. Appl. No. 13/633,496; dated Nov. 18, 2014, pp. 1-11.
Final Rejection in U.S. Appl. No. 13/633,496; dated Nov. 4, 2013, pp. 1-7.
Final Rejection in U.S. Appl. No. 13/633,563; dated Apr. 22, 2015, pp. 1-12.
Final Rejection in U.S. Appl. No. 13/633,563; dated Dec. 16, 2013, pp. 1-58.
Final Rejection issued in U.S. Appl. No. 14/172,151; dated Jul. 20, 2015, pp. 1-18.
Final Rejection issued in U.S. Appl. No. 12/617,811; dated Jan. 4, 2013, pp. 1-6.
Final Rejection issued in U.S. Appl. No. 12/617,811; dated Jul. 31, 2015, pp. 1-15.
Final Rejection issued in U.S. Appl. No. 13/110,568; dated Feb. 21, 2013, pp. 1-20.
Final Rejection issued in U.S. Appl. No. 13/310,118; dated Aug. 2, 2012, pp. 1-20.
Final Rejection issued in U.S. Appl. No. 13/363,956; dated May 20, 2014, pp. 1-16.
Final Rejection issued in U.S. Appl. No. 13/382,442; dated Jul. 17, 2013, pp. 1-30.
Final Rejection issued in U.S. Appl. No. 13/382,442; dated Jun. 13, 2014, pp. 1-29.
Final Rejection issued in U.S. Appl. No. 13/382,772; dated Jun. 3, 2014, pp. 1-34.
Final Rejection issued in U.S. Appl. No. 13/382,772; dated Feb. 10, 2015, pp. 1-36.
Final Rejection issued in U.S. Appl. No. 13/467,707; dated Feb. 12, 2016, pp. 1-12.
Final Rejection issued in U.S. Appl. No. 13/467,707; dated Feb. 25, 2014, pp. 1-18.
Final Rejection issued in U.S. Appl. No. 13/467,707; dated Jan. 7, 2015, pp. 1-8.
Final Rejection issued in U.S. Appl. No. 13/468,422; dated Jan. 6, 2014, pp. 1-21.
Final Rejection issued in U.S. Appl. No. 13/468,422; dated Jan. 23, 2015, pp. 1-27.
Final Rejection issued in U.S. Appl. No. 13/469,633; dated Dec. 4, 2013, pp. 1-17.
Final Rejection issued in U.S. Appl. No. 13/469,633; dated Jan. 23, 2015, pp. 1-12.
Final Rejection issued in U.S. Appl. No. 13/509,507; dated Jul. 23, 2015, pp. 1-11.
Final Rejection issued in U.S. Appl. No. 13/509,542; dated Nov. 21, 2013, pp. 1-34.
Final Rejection issued in U.S. Appl. No. 13/509,542, dated Jan. 28, 2015, pp. 1-26.
Final Rejection issued in U.S. Appl. No. 13/595,590; dated Apr. 2, 2014, pp. 1-7.
Final Rejection issued in U.S. Appl. No. 13/595,590; dated Dec. 19, 2014, pp. 1-14.
Final Rejection issued in U.S. Appl. No. 13/661,476, dated on Oct. 2, 2014, pp. 1-33.
Final Rejection issued in U.S. Appl. No. 13/692,640; dated Jan. 6, 2015, pp. 1-11.
Final Rejection issued in U.S. Appl. No. 13/692,640; dated Jun. 2, 2015, pp. 1-12.
Final Rejection issued in U.S. Appl. No. 13/700,631; dated Apr. 13, 2015, pp. 1-19.
Final Rejection issued in U.S. Appl. No. 13/700,631; dated Jun. 18, 2014, pp. 1-25.
Final Rejection issued in U.S. Appl. No. 13/819,114; dated Mar. 2, 2015, pp. 1-10.
Final-Rejection issued in U.S. Appl. No. 13/432,811; dated Dec. 12, 2014, pp. 1-8.
Final-Rejection issued in U.S. Appl. No. 13/432,811; dated Mar. 31, 2015, pp. 1-9.
Final-Rejection issued in U.S. Appl. No. 13/432,811; dated Sep. 6, 2014, pp. 1-8.
Final Rejection issued in U.S. Appl. No. 13/509,542, dated Feb. 10, 2016, pp. 1-40.
Final-Rejection issued in U.S. Appl. No. 13/432,811; dated Feb. 10, 2016, pp. 1-9.
Fonseca V.A., et al., "Efficacy and Safety of the once-Daily GLP-1 Receptor Agonist Lixisenatide in Monotherapy: A Randomized, Double-Blind, Placebo-Controlled Trial in Patients with Type 2 Diabetes (Getgoal-Mono)," Diabetes Care, 2012, vol. 35 (6), pp. 1225-1231.
Fox J.D., et al., "Single Amino Acid Substitutions on the Surface of *Escherichia coli* Maltose-Binding Protein can have a Profound Impact on the Solubility of Fusion Proteins," Protein Science, 2001, vol. 10 (3), pp. 622-630.
Fransson J., et al., "Oxidation of Human Insulin-Like Growth Factor I in formulation Studies: Kinetics of Methionine Oxidation in Aqueous Solution and in Solid State," Pharmaceutical Research, Aug. 1996, vol. 13 (8), pp. 1252-1257.
Galloway J.A., et al., "New forms of Insulin," Diabetes, 1972, vol. 21 (2 Suppl), pp. 637-648.
Gallwitz B., "Liraglutide. GLP-1 Receptor Agonist Treatment of Type 2 Diabetes Treatment of Obesity," Drugs of the Future, Jan. 2008, vol. 33 (1), pp. 13-20.
Gandhi S., et al., "Molecular Pathogenesis of Parkinson's Disease," Human Molecular Genetics, 2005, vol. 14 (18), pp. 2749-2755.
Garber A., et al., "Liraglutide Versus Glimepiride Monotherapy for Type 2 Diabetes (Lead-3 Mono): A Randomised, 52-Week, Phase III, Double-Blind, Parallel-Treatment Trial," The Lancet, Feb. 7, 2009, vol. 373 (9662), pp. 473-481.
Garg R., et al., "U-500 Insulin: Why, When and How to Use in Clinical Practice," Diabetes/Metabolism Research and Reviews, 2007, vol. 23 (4), pp. 265-268.
Garriques L.N., et al., "The Effect of Mutations on the Structure of Insulin Fibrils Studied by Fourier Transform infrared (FTIR) Spectroscopy and Electron Microscopy," Journal of Pharmaceutical Sciences, 2002, vol. 91 (12), pp. 2473-2480.
Gault V.A., et al., "GLP-1 Agonists Facilitate Hippocampal Ltp and Reverse the Impairment of LTP induced by Beta-Amyloid," European Journal of Pharmacology, Jun. 10, 2008; published online Mar. 29, 2008, vol. 587 (1-3), pp. 112-117.
Gavin J.R., "Report of the Expert Committee on the Diagnosis and Classification of Diabetes Mellitus," Diabetes Care, Jul. 1997, vol. 20 (7), pp. 1183-1197.
Geiger R., "The Chemistry of Insulin," Chemiker Zeitung, Jan. 1976, vol. 100 (3), pp. 54-56.
Gengler S., et al., "Val(8)GLP-1 Rescues Synaptic Plasticity and Reduces Dense Core Plaques in APP/PS1 Mice," Neurobiology of Aging, 2012, vol. 33 (2), pp. 265-276.

(56) References Cited

OTHER PUBLICATIONS

Gerich et al., "Monotherapy with GLP-1 receptor agonist, Lixisenatide, significantly improves glycaemic control in type 2 diabetic patients," Diabetologia 53(Supplement 1)p. S330, Abstract 830, Presented at 46th Annual Meeting of EASD, Stockholm, Sweden, p. 1 (Sep. 2010).
Giugliano D., et al., "Treatment Regimens with Insulin Analogues and Haemoglobin A1C Target of <7% in Type 2 Diabetes: A Systematic Review," Diabetes Research and Clinical Practice, 2010, vol. 92 (1), pp. 1-10.
Goke R., et al., "Distribution of GLP-1 Binding Sites in the Rat Brain: Evidence That Exendin-4 is a Ligand of Brain GLP-1 Binding Sites," European Journal of Neuroscience, 1995, vol. 7 (11), pp. 2294-2300.
Goke R., et al., "Exendin-4 is a High Potency Agonist and Truncated Exendin-(9-39)-Amide an Antagonist at the Glucagon-Like Peptide 1-(7-36)-Amide Receptor of Insulin-Secreting Beta-Cells," The Journal of Biological Chemistry, 1993, vol. 268 (26), pp. 19650-19655.
Goldstein D.E., et al., "Tests of Glycemia in Diabetes," Diabetes Care, Jun. 1995, vol. 18 (6), pp. 896-909.
Gough K., et al., "Assessment of Dose Proportionality: Report from the Statisticians in the Pharmaceutical Industry/ Pharmacokinetics UK Joint Working Party," Drug Information Journal, 1995, vol. 29, pp. 1039-1048.
Goykhman S., et al., "Insulin Glargine: A Review 8 Years After its introduction," Expert Opinion on Pharmacotherapy, 2009, vol. 10 (4), pp. 705-718.
Greig N.H., et al., "Once Daily Injection of Exendin-4 to Diabetic Mice Achieves Long-Term Beneficial Effects on Blood Glucose Concentrations," Diabetologia, 1999, vol. 42 (1), pp. 45-50.
Gura T., "Systems for Identifying New Drugs Are often Faulty," Science, 1997, vol. 278 (5340), pp. 1041-1042.
Gutniak M., et al., "Antidiabetogenic Effect of Glucagon-Like Peptide-1 (7-36) Amide in Normal Subjects and Patients with Diabetes Mellitus," The New England Journal of Medicine, 1992, vol. 326 (20), pp. 1316-1322.
Gygi S.P., et al, "Quantitative Analysis of Complex Protein Mixtures Using Isotope-Coded Affinity Tags," Nature Biotechnology, Oct. 1999, vol. 17 (10), pp. 994-999.
Hamilton A., et al., "Novel GLP-1 Mimetics Developed to Treat Type 2 Diabetes Promote Progenitor Cell Proliferation in the Brain," Journal of Neuroscience Research, 2011, vol. 89 (4), pp. 481-489.
Hamilton A., et al., "Receptors for the incretin Glucagon-Like Peptide-1 are Expressed on Neurons in the Central Nervous System," NeuroReport, 2009, vol. 20 (13), pp. 1161-1166.
Hanas R., et al., "2010 Consensus Statement on the Worldwide Standardization of the Hemoglobin A1C Measurement," Diabetes Care, Aug. 2010, vol. 33 (8), pp. 1903-1904.
Hanefeld M., et al., "The Postprandial State and the Risk of Atherosclerosis," Diabetic Medicine, 1997, vol. 14 (Suppl 3), pp. S6-S11.
Hanefeld M., "Normnahe Postprandiale Hyperglykamie—Eine Essenzielle Komponente Guter Diabeteskontrolle Und Prävention Kardiovaskulärer Erkrankungen (Near-Normal Postprandial Hyperglycemia—An Essential Component of Good Diabetes Control and Prevention of Cardiovascular Diseases)," Paul Langerhans Lecture Diabetologie und Stoffwechsel, 2007, vol. 2, pp. 362-369, In German with English abstract.
Hanna et al., "Canadian Diabetes Association Clinical Practice Guidelines Expert Committee Pharmacologic Management of Type 2 Diabetes," Canadian Journal of Diabetes, Dec. 2003, vol. 27 (Supp 2), pp. S37-S42.
Harkavyi A., et al., "Glucagon-Like Peptide I Receptor Stimulation Reverses Key Deficits in Distinct Rodent Models of Parkinson's Disease," Journal of Neuroinflammation, 2008, vol. 5 (19), pp. 1-9.
Harris S.B., et al., "Clinical inertia in Patients with T2Dm Requiring Insulin in Family Practice," Canadian Family Physician, 2010, vol. 56 (12), pp. e418-e424.

Hartmann H., et al., "Biological Activity of Des-(626-630)-Insulinamide and Related Analogues in Rat Hepatocyte Cultures," Diabetologia, 1989, vol. 32 (7), pp. 416-420.
Heinrich G., et al., "Pre-Proglucagon Messenger Ribonucleic Acid: Nucleotide and Encoded Amino Acid Sequences of the Rat Pancreatic Complementary Deoxyribonucleic Acid," Endocrinology, 1984, vol. 115 (6), pp. 2176-2181.
Hellstrom M., et al., "T1388 GTP-010 as a Therapetuic tool in IBS Pain Relief: Prospective, Randomized, Palebo-Controlled Study of a GLP-1 Analog," Gastroenterology, Apr. 2008, vol. 134 (4), pp. A-544.
Higgins G.C., et al., "Oxidative Stress: Emerging Mitochondrial and Cellular themes and Variations in Neuronal Injury," Journal of Alzheimer's Disease, 2010, vol. 20, pp. S453-S473.
Himeno T., et al., "Beneficial Effects of Exendin-4 on Experimental Polyneuropathy in Diabetic Mice," Diabetes, 2011, vol. 60 (9), pp. 2397-2406.
Hinds K., et al., "Synthesis and Characterization of Poly(Ethylene Glycol)-Insulin Conjugates," Bioconjugate Chemistry, Mar.-Apr. 2000, vol. 11 (2), pp. 195-201.
Hoe 901/2004 Study Investigators Group, "Safety and Efficacy of Insulin Glargine (Hoe 901) Versus NPH Insulin in Combination with oral Treatment in Type 2 Diabetic Patients," Diabetic Medicine, 2003, vol. 20, pp. 545-551.
Holman R.R., et al., "10-Year Follow-Up of intensive Glucose Control in Type 2 Diabetes," The New England Journal of Medicine, 2008, vol. 359 (15), pp. 1577-1589.
Holscher C., "Development of Beta-Amyloid-induced Neurodegeneration in Alzheimer's Disease and Novel Neuroprotective Strategies," Reviews in the Neurosciences, 2005, vol. 16 (3), pp. 181-212.
Holscher C., et al., "New Roles for Insulin-Like Hormones in Neuronal Signalling and Protection: New Hopes for Novel Treatments of Alzheimer's Disease?," Neurobiology of Aging, 2008, vol. 31 (9), pp. 1495-1502.
Holscher C., "Incretin Analogues that have been Developed to Treat Type 2 Diabetes Hold Promise as a Novel Treatment Strategy for Alzheimer's Disease," Recent Patents on Cns Drug Discovery, 2010, vol. 5 (2), pp. 109-117.
Holscher C., "Possible Causes of Alzheimer's Disease: Amyloid Fragments, Free Radical, and Calcium Homeostasis," Neurobiology of Disease, 1998, vol. 5 (3), pp. 129-141.
Holscher C., "The Role of GLP-1 in Neuronal Activity and Neurodegeneration," Vitamins and Hormones, 2010, vol. 84, pp. 331-354.
Holst J.J., et al., "Combining GLP-1 Receptor Agonists with Insulin: therapeutic Rationales and Clinical Findings," Diabetes, Obesity and Metabolism, 2013, vol. 15 (1), pp. 3-14.
Holst J.J., "Glucagon-Like Peptide-1, a Gastrointestinal Hormone with a Pharmaceutical Potential," Current Medicinal Chemistry, 1999, vol. 6 (11), pp. 1005-1017.
Home P.D., et al., "Insulin Treatment: A Decade of Change," British Medical Bulletin, 1989, vol. 45 (1), pp. 92-110.
http://diabetes.emedtv.com/lantus/generic-lantus.html; one page, last accessed Dec. 23, 2015.
Humalog® prescribing information, Apr. 2012, pp. 1-6.
Hunter K., et al., "Drugs Developed to Treat Diabetes, Liraglutide and Lixisenatide, Cross the Blood Brain Barrier and Enhance Neurogenesis," BMC Neuroscience, 2012, vol. 13, pp. 1-6.
Inpharma, Product News. "AVE0010 set to deliver in type 2 diabetes mellitus," Database Adisnews, retrieved from STN, Jun. 2008, pp. 1-3.
"Insulin Aspart Injection." Formulated Preparations: Specific Monographs. British Pharmacopoeia 3. pp. 1-3 (2012).
Insulinpraparat Wikipedia, http://de.wikipedia.org/wiki/Insulinpr%C3%A4parat, pp. 1-15 (Feb. 5, 2013).
Insuman® Comb25 prescribing information, Feb. 2011, pp. 1-4.
Insuman® Infusat prescribing information, Feb. 2011, pp. 1-4.
International Search Report by the ISA for International Application No. PCT/EP2007/005932; dated Oct. 9, 2007, pp. 1-6.
International Search Report by the ISA for International Application No. PCT/EP2009/000017; dated Jun. 22, 2009, pp. 1-7.

(56) References Cited

OTHER PUBLICATIONS

International Search Report by the ISA for International Application No. PCT/EP2009/063195; dated May 6, 2010.
International Search Report by the ISA for International Application No. PCT/EP2010/059436; dated Jun. 17, 2011, pp. 1-5.
International Search Report by the ISA for International Application No. PCT/EP2010/059438; dated Oct. 4, 2010, pp. 1-3.
International Search Report by the ISA for International Application No. PCT/EP2010/062638; dated Mar. 18, 2011, pp. 1-5.
International Search Report by the ISA for International Application No. PCT/EP2010/067250; dated Mar. 23, 2011, pp. 1-3.
International Search Report by the ISA for International Application No. PCT/EP2011/058079; dated Mar. 22, 2012, pp. 1-6.
International Search Report by the ISA for International Application No. PCT/EP2011/058764; dated Jun. 30, 2011, pp. 1-9.
International Search Report by the ISA for International Application No. PCT/EP2012/051670; dated Mar. 26, 2012, pp. 1-16.
International Search Report by the ISA for International Application No. PCT/EP2012/055660; dated May 10, 2012, pp. 1-6.
International Search Report by the ISA for International Application No. PCT/EP2012/058745; dated Jul. 12, 2012, pp. 1-6.
International Search Report by the ISA for International Application No. PCT/EP2012/058747; dated Jul. 8, 2012, pp. 1-6.
International Search Report by the ISA for International Application No. PCT/EP2012/058749; dated Jul. 31, 2012, pp. 1-6.
International Search Report by the ISA for International Application No. PCT/EP2012/058779; dated Aug. 28, 2012, pp. 1-5.
International Search Report by the ISA for International Application No. PCT/EP2012/066617; dated Nov. 22, 2012, pp. 1-5.
International Search Report by the ISA for International Application No. PCT/EP2012/067144; dated Aug. 11, 2012, pp. 1-5.
International Search Report by the ISA for International Application No. PCT/EP2012/069483; dated Nov. 29, 2011, pp. 1-4.
International Search Report by the ISA for International Application No. PCT/EP2012/069485; dated Dec. 11, 2012, pp. 1-5.
International Search Report by the ISA for International Application No. PCT/EP2012/071271; dated Jan. 30, 2013, pp. 1-5.
International Search Report by the ISA for International Application No. PCT/EP2012/074150; dated Nov. 20, 2012, pp. 1-4.
International Search Report by the ISA for International Application No. PCT/EP2014/051976; dated Mar. 4, 2014, pp. 1-3.
International Search Report by the ISA for International Application No. PCT/EP2014/056498; dated Jun. 25, 2014, pp. 1-10.
International Search Report by the ISA for International Application No. PCT/EP2014/062418; dated Sep. 22, 2014, pp. 1-4.
International Search Report by the ISA for International Application No. PCT/EP2015/079285; dated Mar. 9, 2016, pp. 1-7.
Inzucchi S.E., et al., "Management of Hyperglycemia in Type 2 Diabetes: A Patient-Centered Approach," Diabetes Care, Jun. 2012, vol. 35, pp. 1364-1379.
Isacson R., et al., "The Glucagon-Like Peptide 1 Receptor Agonist Exendin-4 improves Reference Memory Performance and Decreases Immobility in the forced Swim Test," European Journal of Pharmacology,650(1):249-55 (Jan. 2011, Epub Oct. 14, 2010).
ISPAD, International Diabetes Federation; "Global/IDF/ISPAD Guideline for Diabetes in Childhood and Adolescence," pp. 1-132 (2011).
Jackson R.L., et al., "Neutral Regular Insulin," Diabetes, 1972, vol. 21 (4), pp. 235-245.
Jain R.K., "Barriers to Drug Delivery in Solid Tumors," Scientific American, Jul. 1994, vol. 271 (1), pp. 58-65.
Jang J.H., et al., "Neuroprotective Effects of *Triticum aestivum* L. Against B-Amyloid-induced Cell Death and Memory Impairments," Phytotherapy Research, 2010, vol. 24 (1), pp. 76-84.
Jekel P.A., et al., "Use of Endoproteinase Lys-C from Lysobacter Enzymogenes in Protein Sequence Analysis," Analytical Biochemistry, 1983, vol. 134 (2), pp. 347-354.
Jendle J., et al., "Insulin and GLP-1 Analog Combinations in Type 2 Diabetes Mellitus: A Critical Review," Expert Opinion on Investigational Drugs, 2012, vol. 21 (10), pp. 1463-1474.

Jimenez S., et al., "Inflammatory Response in the Hippocampus of PS1M146L/App751SL Mouse Model of Alzheimer'S Disease: Age-Dependent Switch in the Microglial Phenotype from Alternative to Classic," The Journal of Neuroscience, 2008, vol. 28 (45), pp. 11650-11661.
Johnson et al., "When is a unit of insulin not a unit of insulin? Detemir dosing in type 2 diabetes" Poster, one page, 2008. http://professional.diabetes.org/ContenUPosters/2008/p8-LB.pdf.
Jorgensen K.H., et al., "Five Fold Increase of Insulin Concentration Delays the Absorption of Subcutaneously Injected Human Insulin Suspensions in Pigs," Diabetes Research and Clinical Practice, 2000, vol. 50, pp. 161-167.
Kaarsholm N.C., et al., "Engineering Stability of the Insulin Monomer Fold with Application to Structure-Activity Relationships," Biochemistry, 1993, vol. 32 (40), pp. 10773-10778.
Kadima W., "Role of Metal Ions in the T- to R-Allosteric Transition in the Insulin Hexamer," Biochemistry, Oct. 1999, vol. 38 (41), pp. 13443-13452.
Kaduszkiewicz H., et al., "Cholinesterase inhibitors for Patients with Alzheimer's Disease: Systematic Review of Randomised Clinical Trials," British Medical Journal (Clinical Research ed.), 2005, vol. 331 (7512), pp. 321-327.
Kaech S., et al., "Culturing Hippocampal Neurons," Nature Protocols, 2006, vol. 1 (5), pp. 2406-2415.
Kahn S.E., et al., "Glycemic Durability of Rosiglitazone, Metformin, or Glyburide Monotherapy," The New England Journal of Medicine, 2006, vol. 355 (23), pp. 2427-2443.
Kakhki V.R.D., et al., "Normal Values of Gallbladder Ejection Fraction Using 99m Tc-Sestamibi Scintigraphy after a Fatty Meal formula," Journal of Gastrointestinal and Liver Diseases, Jun. 2007, vol. 16 (2), pp. 157-161.
Kamisawa T., et al., "Pancreatographic investigation of Pancreatic Duct System and Pancreaticobiliary Malformation," Journal of Anatomy, 2008, vol. 212 (2), pp. 125-134.
Kanazawa M., et al., "Criteria and Classification of Obesity in Japan and Asia-Oceania," Asia Pacific Journal of Clinical Nutrition, Dec. 2002, vol. 11 (Suppl 7), pp. S732-S737.
Kang S., et al., "Subcutaneous Insulin Absorption Explained by Insulin'S Physicochemical Properties Evidence from Absorption Studies of Soluble Human Insulin and Insulin Analogues in Humans," Diabetes Care, Nov. 1991, vol. 14 (11), pp. 942-948.
Kao C.H., et al., "The Evaluation of Gallbladder Function by Quantitative Radionuclide Cholescintigraphy in Patients with Noninsulin-Dependent Diabetes Mellitus," Nuclear Medicine Communications, 1993, vol. 14 (10), pp. 868-872.
Kapitza et al., Abstract "Pharmacodynamic Characteristics of Lixisenatide QD vs Liraglutide QD in Patients with T2DM Inadequately Controlled with Metformin" Abtract D-0740, presented at the World Diabetes Congress in Dubai, Dec. 5-8, 2011, one page.
Kastin A.J., et al., "Entry of Exedin-4 into Brain is Rapid but may be Limited at High Doses International Journal of Obesity and Related Metabolic Disorders," Journal of the International Association for the Study of Obesity, 2003, vol. 27 (3), pp. 313-318.
Kastin A.J., et al., "Interactions of Glucagon-Like Peptide-1 (GLP-1) with the Blood-Brain Barrier," Journal of Molecular Neuroscience, 2001, vol. 18 (1-2), pp. 7-14.
Kemmler W., et al., "Studies on the Conversion of ProInsulin to Insulin," The Journal of Biological Chemistry, 1971, vol. 246 (22), pp. 6786-6791.
Kendall D.M., et al., "Effects of Exenatide (Exendin-4) on Glycemic Control Over 30 Weeks in Patients with Type 2 Diabetes Treated with Metformin and a Sulfonylurea," Diabetes care, May 2005, vol. 28 (5), pp. 1083-1091.
Kielgast U., et al., "Treatment of Type 1 Diabetic Patients with Glucagon-Like Peptide-1 (GLP-1) and GLP-1R Agonists," Current Diabetes Reviews, Nov. 2009, vol. 5 (4), pp. 266-275.
Kim S., et al., "Exendin-4 Protects Dopaminergic Neurons by Inhibition of Microglial Activation and Matrix Metalloproteinase-3 Expression in an Animal Model of Parkinson's Disease," Journal of Endocrinology, 2009, vol. 202 (3), pp. 431-439.

(56) References Cited

OTHER PUBLICATIONS

Knee T.S., et al., "A Novel Use of U-500 Insulin for Continuous Subcutaneous Insulin infusion in Patients with Insulin Resistance: A Case Series," Endocrine Practice, May/Jun. 2003, vol. 9 (3), pp. 181-186.

Knudsen L.B., et al., "Potent Derivatives of Glucagon-Like Peptide-1 with Pharmacokinetic Properties Suitable for once Daily Administration," Journal of Medicinal Chemistry, 2000, vol. 43 (9), pp. 1664-1669.

Kohn W.D., et al., "Pi-Shifted Insulin Analogs with Extended in Vivo Time Action and Favorable Receptor Selectivity," Peptides, 2007, vol. 28 (4), pp. 935-948.

Kohner E.M., "Diabetic Retinopathy," British Medical Bulletin, 1989, vol. 45 (1), pp. 148-173.

Kolterman O.G., et al., "Synthetic Exendin-4 (Exenatide) Significantly Reduces Postprandial and Fasting Plasma Glucose in Subjects with Type 2 Diabetes," The Journal of Clinical Endocrinology & Metabolism, 2003, vol. 88 (7), pp. 3082-3089.

Korczyn A.D., et al, "Emerging therapies in the Pharmacological Treatment of Parkinson's Disease," Drugs, 2002, vol. 62 (5), pp. 775-786.

Krishnamurthy G.T., et al., "Constancy and Variability of Gallbladder Ejection Fraction: Impact on Diagnosis and therapy," Journal of Nuclear Medicine, Nov. 2004, vol. 45 (11), pp. 1872-1877.

Lando, "The New 'Designer' Insulins", Clinical Diabetes, 18(4): Fall 2000 (http://journal.diabetes.org/clinical diabelesN18N42000/pg154.hlm; accessed Oct. 22, 2013, pp. 1-13).

Langston J.W., et al., "Chronic Parkinsonism in Humans due to a Product of Meperedine- Analog Synthesis," Science, 1983, vol. 219 (4587), pp. 979-980.

Langui D., et al., "Subcellular Topography of Neuronal Aβ Peptide in APPxPS1 Transgenic Mice," The American Journal of Pathology, 2004, vol. 165 (5), pp. 1465-1477.

Lantus® ANNEX I—Summary of product characteristics. Date of first authorisation: Jun. 9, 2000, pp. 1-164.

Lantus® prescribing information, May 2012, pp. 1-6.

Lantus® Product Information—European Medicines Agency, first published Aug. 5, 2009, pp. 1-2.

Larsen B.D., et al., "Sequence-Assisted Peptide Synthesis (SAPS)," Journal of Peptide Research, 1998, vol. 52 (6), pp. 470-476.

Larsen P.J., et al., "Combination of the Insulin Sensitizer, Pioglitazone, and the Long-Acting Glp-1 Human Analog, Liraglutide, Exerts Potent Synergistic Glucose-Lowering Efficacy in Severely Diabetic ZDF Rats," Diabetes, Obesity and Metabolism, 2008, vol. 10, pp. 301-311.

Laursen K., et al., "Enhanced Monitoring of Biopharmaceutical Product Purity Using Liquid Chromatography-Mass Spectrometry," Journal of Chromatography A, Jul. 2011; Epub May 2011, vol. 1218 (28), pp. 4340-4348.

Lee C.H., et al., "Ischemia-Induced Changes in Glucagon-Like Peptide-1 Receptor and Neuroprotective Effect of its Agonist, Exendin-4, in Experimental Transient Cerebral Ischemia," Journal of Neuroscience Research, 2011, vol. 89 (7), pp. 1103-1113.

Leib R.D., et al., "Direct Quantitation of Peptide Mixtures without Standards Using Clusters formed by Electrospray Ionization Mass Spectrometry," Analytical Chemistry, May 2009, vol. 81 (10), pp. 3965-3972.

Lens J., "The Terminal Carboxyl Groups of Insulin," Biochimica et Biophysica Acta, 1949, vol. 3, pp. 367-370.

Levemir® prescribing information, Dec. 2011, pp. 1-6.

Levene P.A., et al., "Calculation of Isoelectric Point," The Journal of Biological Chemistry, 1923, vol. 55, pp. 801-813.

Levin P., et al., "Combination therapy with Insulin Glargine and Exenatide: Real-World Outcomes in Patients with Type 2 Diabetes," Current Medical Research and Opinion, 2012, vol. 28 (3), pp. 439-446.

Levine R.L., et al., "Oxidation of Methionine in Proteins: Roles in Antioxidant Defense and Cellular Regulation," IUBMB life, Oct. 2000, vol. 50 (4-5), pp. 301-307.

Leyer S., et al., "The Role of the C-Terminus of the Insulin B-Chain in Modulating Structural and Functional Properties of the Hormone," International Journal of Peptide and Protein Research, 1995, vol. 46 (5), pp. 397-407.

Li H., et al., "Chronic Treatment of Exendin-4 Affects Cell Proliferation and Neuroblast Differentiation in the Adult Mouse Hippocampal Dentate Gyrus," Neuroscience letters, 2010, vol. 19, pp. 1205-1219.

Li L., et al., "Common Pathological Processes in Alzheimer Disease and Type 2 Diabetes: A Review," Brain Research Reviews, 2007, vol. 56, pp. 384-402.

Li Y., et al., "Enhancing the GLP-1 Receptor Signaling Pathway Leads to Proliferation and Neuroprotection in Human Neuroblastoma Cells," Journal of Neurochemistry, 2010, vol. 113 (6), pp. 1621-1631.

Li Y., et al., "GLP-1 Receptor Stimulation Preserves Primary Cortical and Dopaminergic Neurons in Cellular and Rodent Models of Stroke and Parkinsonism," Proceedings of the National Academy of Sciences of the United States of America, 2009, vol. 106 (4), pp. 1285-1290.

Li Y., et al., "GLP-1 Receptor Stimulation Reduces Amyloid-Beta Peptide Accumulation and Cytotoxicity in Cellular and Animal Models of Alzheimer's Disease," Journal of Alzheimer's Disease, 2010, vol. 19 (4), pp. 1205-1219.

Lill N., "Production of Fast-Acting Insulins and Delayed-Release Insulins—How can this Problem be Solved by Technology? Insulin formulations," Pharmazie in Unserer Zeit, 2001, vol. 30 (1), pp. 56-61, (English Translation Included).

Liu & Ruus, Abstract "Pharmacokinetics and Safety of the GLP-1 Agonist AVE0010 in Patients with Renal Impairment," Diabetes 58 (Suppl. 1): Abstract 557-P for the 69th Scientific Session of the American Diabetes Association Jun. 5-9, 2009, New Orleans, Louisiana, pp. 1-2.

Lixisenatide, Chemical Structure CID 16139342, Pubchem, accessed Feb. 5, 2015 at URL pubchem.ncbi.nlm.nih.gov/summary/summary.cgi?sid=135267128&viewopt=Deposited, pp. 1-3.

Lopez-Delgado M.I., et al., "Effects of Glucagon-Like Peptide 1 on the Kinetics of Glycogen Synthase a in Hepatocytes from Normal and Diabetic Rats," Endocrinology, 1998, vol. 139 (6), pp. 2811-2817.

Lotharius J., et al., "Effect of Mutant Alpha-Synuclein on Dopamine Homeostasis in a New Human Mesencephalic Cell Line," The Journal of Biological Chemistry, 2002, vol. 277 (41), pp. 38884-38894.

Lotharius J., et al., "Progressive Degeneration of Human Mesencephalic Neuron-Derived Cells Triggered by Dopamine-Dependent Oxidative Stress is Dependent on the Mixed-Lineage Kinase Pathway," Journal of Neuroscience, 2005, vol. 25 (27), pp. 6329-6342.

Lougheed W.D., et al., "Physical Stability of Insulin Formulations," Diabetes, 1983, vol. 32 (5), pp. 424-432.

Lyxumia 10 micrograms solution for injection, Summary of Product Characteristics, updated Oct. 31, 2014, pp. 1-12.

Lyxumia® ANNEX I—Summary of product characteristics. Date of first authorisation: Feb. 1, 2013, pp. 1-92.

Lyxumia, Chemical Subgroup A10BX, Community Register of Medicinal Products for Human Use, Eurpean Commission Public Health, p. 1-2 (May 2, 2013).

Lyxumia® Product Information—European Medicines Agency, first published Mar. 14, 2013, pp. 1-2.

Mancuso M., et al., "Clinical Features and Pathogenesis of Alzheimer's Disease: involvement of Mitochondria and Mitochondrial DNA," Advances in Experimental Medicine and Biology, 2010, vol. 685, pp. 34-44.

Marbury T.C., et al., "A Pilot Study to Examine the Feasibility of Insulin Glargine in Subjects with Impaired Fasting Glucose, Impaired Glucose tolerance or New-onset Type 2 Diabetes," Experimental and Clinical Endocrinology & Diabetes, May 2008, vol. 116 (5), pp. 282-288.

Margolis R.L., et al., "Diagnosis of Huntington Disease," Clinical Chemistry, 2003, vol. 49 (10), pp. 1726-1732.

(56) References Cited

OTHER PUBLICATIONS

Markussen J., et al., "Soluble, Prolonged-Acting Insulin Derivatives. I. Degree of Protraction and Crystallizability of Insulins Substituted in the Termini of the B-Chain," Protein Engineering, 1987, vol. 1 (3), pp. 205-213.
Markussen J., et al., "Soluble, Prolonged-Acting Insulin Derivatives II Degree of Protraction and Crystallizability of Insulins Substituted in Positions A17, B8, B13, B27 and B30," Protein Engineering, 1987, vol. 1 (3), pp. 215-223.
Markussen J., et al., "Soluble, Prolonged-Acting Insulin Derivatives. III. Degree of Protraction, Crystallizability and Chemical Stability of Insulins Substituted in Positions A21, B13, B23, B27 and B30," Protein Engineering, 1988, vol. 2 (2), pp. 157-166.
Martin B., et al., "Exendin-4 Improves Glycemic Control, Ameliorates Brain and Pancreatic Pathologies, and Extends Survival in a Mouse Model of Huntington's Disease," Diabetes, 2009, vol. 58 (2), pp. 318-328.
Martin L.J., et al., "Neurodegeneration in Excitotoxicity, Global Cerebral Ischemia, and Target Deprivation: A Perspective on the Contributions of Apoptosis and Necrosis," Brain Research Bulletin, 1998, vol. 46 (4), pp. 281-309.
Mattson M.P., "Calcium and Neurodegeneration," Aging Cell, 2007, vol. 6 (3), pp. 337-350.
McClean P.L., et al., "Glucagon-Like Peptide-1 Analogues Enhance Synaptic Plasticity in the Brain: A Link between Diabetes and Alzheimer's Disease," European Journal of Pharmacology, 2010, vol. 630 (1-3), pp. 158-162.
McClean P.L., et al., "The Diabetes Drug Liraglutide Prevents Degenerative Processes in a Mouse Model of Alzheimer's Disease," The Journal of Neuroscience, 2011, vol. 31 (17), pp. 6587-6594.
Mecklenburg R.S., et al., "Complications of Insulin Pump therapy: The Effect of Insulin Preparation," Diabetes Care, 1985, vol. 8 (4), pp. 367-370.
Medline Plus, "Obesity" available at http://www.nlm.nih.gov/medlineplus/obesity.html, Retrieved Aug. 22, 2013, one page.
Meier J.J., "GLP-1 Receptor Agonists for individualized Treatment of Type 2 Diabetes Mellitus," Nature Reviews. Endocrinology, 2012, vol. 8 (12), pp. 728-742.
Merrifield B., "Solid Phase Synthesis," Science, 1986, vol. 232 (4748), pp. 341-347.
Mikhail N.E., "Is Liraglutide a Useful Addition to Diabetes therapy?," Endocrine Practice, Nov.-Dec. 2010, vol. 16 (6), pp. 1028-1037.
Monnier L., et al., "The Loss of Postprandial Glycemic Control Precedes Stepwise Deterioration of Fasting with Worsening Diabetes," Diabetes Care, 2007, vol. 30 (2), pp. 263-269.
Moreno-Gonzalez I., et al., "Extracellular Amyloid-B and Cytotoxic Glial Activation Induce Significant Entorhinal Neuron Loss in Young PS1M146L/APP751SL Mice," Journal of Alzheimer's Disease, 2009, vol. 18, pp. 755-776.
Moretto T.J., et al., "Efficacy and tolerability of Exenatide Monotherapy Over 24 Weeks in Antidiabetic Drug-Naive Patients with Type 2 Diabetes: A Randomized, Double-Blind, Placebo-Controlled, Parallel-Group Study," Clinical Therapeutics, Aug. 2008, vol. 30 (8), pp. 1448-1460.
Muller G., et al., "Insulin Signaling in the Yeast *Saccharomyces cerevisiae*. 1. Stimulation of Glucose Metabolism and Snf 1 Kinase by Human Insulin," Biochemistry, Jun. 1998, vol. 37 (24), pp. 8683-8695.
Muzaffar M., et al., "The Mechanism of Enhanced Insulin Amyloid Fibril formation by Naciis Better Explained by a Conformational Change Model," PLoS One, 2011, vol. 6 (11), pp. 1-11, e27906.
Nakagawa A., et al., "Receptor Gene Expression of Glucagon-Like Peptide-1, but not Glucose-Dependent Insulinotropic Polypeptide, in Rat Nodose Ganglion Cells," Autonomic Neuroscience, 2004, vol. 110, pp. 36-43.
Nathan D.M., et al., "Management of Hyperglycaemia in Type 2 Diabetes Mellitus: A Consensus Algorithm for the initiation and Adjustment of therapy. Update Regarding the Thiazolidinediones," Diabetologia, 2008, vol. 51 (1), pp. 8-11.

Nathan M.D., et al., "Insulinotropic Action of Glucagon Like Peptide-1-(7-37) in Diabetic and Nondiabetic Subjects," Diabetes Care, 1992, vol. 15 (2), pp. 270-276.
Nauck M.A., et al., "Comparative Evaluation of Incretin-Based Antidiabetic Medications and Alternative therapies to be Added to Melformin in the Case of Monotherapy Failure," Journal of Diabetes Investigation, Feb.-Apr. 2010, vol. 1 (1-2), pp. 24-36.
Nauck M.A., et al., "Effects of Subcutaneous Glucagon-Like Peptide 1 (GLP-1 [7-36 Amide]) in Patients with NIDDM," Diabetologia, 1996, vol. 39 (12), pp. 1546-1553.
Nauck M.A., et al., "Glucagon-Like Peptide 1 and its Potential in the Treatment of Non-Insulin-Dependent Diabetes Mellitus," Hormone and Metabolic Research, 1997, vol. 29 (9), pp. 411-416.
Nauck M.A., et al., "Glucagon-Like Peptide 1 (GLP-1) as a New therapeutic Approach for Type 2-Diabetes," Experimental and Clinical Endocrinology, 1997, vol. 105 (4), pp. 187-195.
NCT00299871, ClinicalTrials.gov, "Dose Ranging Study of the GLP-1 Agonist AVE0010 in Metformin-Treated Subjects With Type 2 Diabetes Mellitus," Jun. 22, 2010, Retrieved Nov. 7, 2011, pp. 1-5.
NCT00688701 Clinical Trials.gov "GLP-1 Receptor Agonist Lixisenatide in Patients with Type 2 Diabetes for Glycemic Control and Safety Evaluation in Monotherapy (GETGOAL-MONO)" accessed Jul. 27, 2014; pp. 1-5.
NCT00712673, Clinical Trials.gov, "GLP-A Agonist AVE0010 (Morning or Evening) in Patients with Type 2 Diabetes for Glycemic Control and Safety Evaluation, on Top of Metformin", Mar. 22, 2011, pp. 1-4.
NCT00715624 Clinical Trials.gov "GLP-1 Receptor Agonist Lixisenatide in Patients With Type 2 Diabetes for Glycemic Control and Safety Evaluation, on Top of Basal Insulin (GETGOAL-L)" (2008-2014), p. 1-6 (Feb. 2011).
NCT00763815, ClinicalTrials.gov, U.S. National Institutes of Health: "GLP-1 Agonist AVE0010 in Patients With Type 2 Diabetes for Glycemic Control and Safety Evaluation on Top of Pioglitazone (GETGOAL-P)" pp. 1-8 (Jun. 27, 2011).
NCT00975286, Clinical Trials.gov, "24-week Treatment with Lixisenalide in Type 2 Diabetes Insufficiently Controlled With Melformin and Insulin Glargine", Aug. 8, 2011, pp. 1-4.
NCT00976937, ClinicalTrials.gov, "24-week Study Comparing Lixisenatide (AVE0010) to Sitagliptin as add-on to Metformin in Obese Type 2 Diabetic Patients Younger Than 50," May 6, 2011, Retrieved Nov. 7, 2011, pp. 1-4.
NCT01146678, ClinicalTrials.gov "Relative Bioavailability and Activity of Different Formulations of Insulin Glargine and Lixisenatide in Patients With Diabetes Mellitus Type 1" last updated Sep. 10, 2010, pp. 1-4.
NCT01174810, ClinicalTrials.gov "Exendin-4 as a Treatment for Parkinson's Disease—Pilot Study" accessed Aug. 8, 2011, pp. 1-5.
NCT01195454, NIH Clinical Trials, "Euglycemic clamp dose-response study comparing insulin glargine U300 with Lantus U100" last updated Dec. 13, 2010, pp. 1-4.
NCT01255163, ClinicalTrials.gov "A Clinical Trial of Exendin-4 for the Treatment of Alzheimer's Disease" accessed Aug. 8, 2011, pp. 1-7.
NCT02058147 ClinicalTrials.gov "Efficacy and Safety of Insulin Glargine/Lixisenatide Fixed Ratio Combination Compared to Insulin Glargine Alone and Lixisenatide Alone on Top Metformin in Patients With T2DM (LixLan-O)" first received by ClinicalTrials.gov on Feb. 6, 2014, pp. 1-3.
NCT02058160 ClinicalTrials.gov "Efficacy and Safety of the Insulin Glargine/Lixisenatide Fixed Ratio Combination Versus Insulin Glargine in Patients With Type 2 Diabetes (LixiLan-L)" first received by ClinicalTrials.gov on Feb. 6, 2014, pp. 1-3.
Needleman S.B., et al., "A General Method Applicable to the Search for Similarities in the Amino Acid Sequence of Two Proteins," Journal of Molecular Biology, 1970, vol. 48 (3), pp. 443-453.
Neidle, "18.2 Failure Modes in the Discovery Process" Cancer Drug Design and Discovery, Elsevier/Academic Press, pp. 427-431 (2008).
Nettleton E.J., et al., "Characterization of the Oligomeric States of Insulin in Self-Assembly and Amyloid Fibril formation by Mass Spectrometry," Biophysical Journal, 2000, vol. 79 (2), pp. 1053-1065.

(56) References Cited

OTHER PUBLICATIONS

NHSC—National Horizon Scanning Center, "AVE0010 (ZP10) for type 2 diabetes mellitus" University of Birmingham, England; pp. 1-6 (Dec. 2008).
Nicklas et al., "Inhibition of Nadh-Linked Oxidation in Brain Mitochondria by 1-Methyl-4-Phenyl-Pyridine, a Metabolite of the Neurotoxin, 1-Methyl-4-Phenyl-1,2,5,6-Tetrahydropyridine," Life Sciences, 1985, vol. 36, pp. 2503-2508.
Nielsen L.L., et al., "Pharmacology of Exenatide (Synthetic Exendin-4): A Potential therapeutic for Improved Glycemic Control of Type 2 Diabetes," Regulatory Peptides, 2004, vol. 117 (2), pp. 77-88.
Noble S.L., et al., "Insulin Lispro: A Fast-Acting Insulin Analog," American Family Physician, 1998, vol. 57 (2), pp. 279-286.
Non-Final Office Action from U.S. Appl. No. 12/617,805; dated Jul. 24, 2014, pp. 1-12.
Non-Final Office Action from U.S. Appl. No. 12/617,805; dated May 2, 2012, pp. 1-11.
Non-Final Office Action from U.S. Appl. No. 12/617,805; dated May 10, 2011, pp. 1-12.
Non-Final Office Action from U.S. Appl. No. 12/617,805; dated Sep. 15, 2015, pp. 1-12.
Non-Final Office Action issued in U.S. Appl. No. 13/123,835; dated Dec. 22, 2014, pp. 1-13.
Non-Final Office Action issued in U.S. Appl. No. 13/123,835; dated Jul. 19, 2012, pp. 1-14.
Non-Final Office Action issued in U.S. Appl. No. 13/123,835; dated May 28, 2015, pp. 1-11.
Non-Final Rejection in U.S. Appl. No. 13/633,496; dated Apr. 29, 2013, pp. 1-53.
Non-Final Rejection in U.S. Appl. No. 13/633,496; dated Apr. 6, 2015, pp. 1-14.
Non-Final Rejection in U.S. Appl. No. 13/633,496; dated May 22, 2014, pp. 1-11.
Non-Final Rejection in U.S. Appl. No. 13/633,563; dated Dec. 1, 2014, pp. 1-9.
Non-Final Rejection in U.S. Appl. No. 13/633,563; dated Jul. 1, 2013, pp. 1-56.
Non-Final Rejection in U.S. Appl. No. 13/633,563; dated Jun. 4, 2014, pp. 1-11.
Non-Final Rejection in U.S. Appl. No. 13/633,563; dated Oct. 6, 2015, pp. 1-12.
Non-Final Rejection issued in U.S. Appl. No. 14/172,151; dated Mar. 24, 2015, pp. 1-16.
Non-Final Rejection issued in U.S. Appl. No. 12/617,811; dated Apr. 27, 2011, pp. 1-10.
Non-Final Rejection issued in U.S. Appl. No. 12/617,811; dated Jan. 14, 2015, pp. 1-15.
Non-Final Rejection issued in U.S. Appl. No. 12/617,811; dated Jun. 21, 2012, pp. 1-7.
Non-Final Rejection issued in U.S. Appl. No. 12/617,811; dated Oct. 27, 2011, pp. 1-13.
Non-Final Rejection issued in U.S. Appl. No. 13/110,568; dated Mar. 19, 2012, pp. 1-18.
Non-Final Rejection issued in U.S. Appl. No. 13/310,118; dated Mar. 19, 2012, pp. 1-19.
Non-Final Rejection issued in U.S. Appl. No. 13/310,118, dated Mar. 29, 2013, pp. 1-21.
Non-Final Rejection issued in U.S. Appl. No. 13/310,118, dated Mar. 25, 2015, pp. 1-15.
Non-Final Rejection issued in U.S. Appl. No. 13/363,956; dated Apr. 10, 2013, pp. 1-15.
Non-Final Rejection issued in U.S. Appl. No. 13/363,956; dated Feb. 11, 2015, pp. 1-18.
Non-Final Rejection issued in U.S. Appl. No. 13/363,956; dated May 29, 2015, pp. 1-17.
Non-Final Rejection issued in U.S. Appl. No. 13/363,956; dated Nov. 20, 2013, pp. 1-10.
Non-Final Rejection issued in U.S. Appl. No. 13/382,442; dated Nov. 7, 2012, pp. 1-26.
Non-Final Rejection issued in U.S. Appl. No. 13/382,442; dated Dec. 19, 2013, pp. 1-29.
Non-Final Rejection issued in U.S. Appl. No. 13/382,442; dated Feb. 5, 2015, pp. 1-31.
Non-Final Rejection issued in U.S. Appl. No. 13/382,442; dated Mar. 31, 2016, pp. 1-29.
Non-Final Rejection issued in U.S. Appl. No. 13/382,772; dated Nov. 21, 2013, pp. 1-42.
Non-Final Rejection issued in U.S. Appl. No. 13/382,772; dated Sep. 29, 2014, pp. 1-33.
Non-Final Rejection issued in U.S. Appl. No. 13/382,772; dated Sep. 14, 2015, pp. 1-42.
Non-Final Rejection issued in U.S. Appl. No. 13/467,707; dated Jul. 15, 2013, pp. 1-20.
Non-Final Rejection issued in U.S. Appl. No. 13/467,707; dated Jul. 25, 2014, pp. 1-22.
Non-Final Rejection issued in U.S. Appl. No. 13/467,707; dated Sep. 16, 2015, pp. 1-13.
Non-Final Rejection issued in U.S. Appl. No. 13/468,422; dated Nov. 4, 2015; pp. 1-27.
Non-Final Rejection issued in U.S. Appl. No. 13/469,633; dated Aug. 19, 2013, pp. 1-25.
Non-Final Rejection issued in U.S. Appl. No. 13/469,633; dated Aug. 22, 2014, pp. 1-23.
Non-Final Rejection issued in U.S. Appl. No. 13/509,507; dated Aug. 6, 2013, pp. 1-11.
Non-Final Rejection issued in U.S. Appl. No. 13/509,507; dated Sep. 19, 2014, pp. 1-9.
Non-Final Rejection issued in U.S. Appl. No. 13/509,507; dated Feb. 19, 2015, pp. 1-10.
Non-Final Rejection issued in U.S. Appl. No. 13/509,507; dated Dec. 8, 2015, pp. 1-14.
Non-Final Rejection issued in U.S. Appl. No. 13/509,542; dated May 23, 2013, pp. 1-21.
Non-Final Rejection issued in U.S. Appl. No. 13/509,542; dated Apr. 2, 2014, pp. 1-20.
Non-Final Rejection issued in U.S. Appl. No. 13/509,542; dated Aug. 11, 2015, pp. 1-30.
Non-Final Rejection issued in U.S. Appl. No. 13/595,590; dated Jun. 5, 2015, pp. 1-9.
Non-Final Rejection issued in U.S. Appl. No. 13/595,590; dated Oct. 16, 2013, pp. 1-7.
Non-Final Rejection issued in U.S. Appl. No. 13/595,590; dated Sep. 5, 2014, pp. 1-10.
Non-Final Rejection issued in U.S. Appl. No. 13/661,476; dated Jun. 4, 2015, pp. 1-31.
Non-Final Rejection issued in U.S. Appl. No. 13/661,476, dated on Dec. 4, 2013, pp. 1-11.
Non-Final Rejection issued in U.S. Appl. No. 13/661,476, dated Mar. 6, 2014, pp. 1-28.
Non-Final Rejection issued in U.S. Appl. No. 13/661,476, dated Sep. 16, 2013, pp. 1-19.
Non-Final Rejection issued in U.S. Appl. No. 13/692,640; dated May 6, 2014, pp. 1-10.
Non-Final Rejection issued in U.S. Appl. No. 13/692,640; dated Oct. 31, 2013, pp. 1-10.
Non-Final Rejection issued in U.S. Appl. No. 13/700,631; dated Apr. 22, 2013, pp. 1-27.
Non-Final Rejection issued in U.S. Appl. No. 13/700,631; dated Dec. 17, 2015, pp. 1-18.
Non-Final Rejection issued in U.S. Appl. No. 13/700,631; dated Nov. 18, 2014, pp. 1-22.
Non-Final Rejection issued in U.S. Appl. No. 13/700,631; dated Nov. 29, 2013, pp. 1-23.
Non-Final Rejection issued in U.S. Appl. No. 13/819,114; dated Dec. 2, 2015, pp. 1-14.
Non-Final Rejection issued in U.S. Appl. No. 13/819,114; dated Jul. 31, 2014, pp. 1-9.
Non-Final Rejection issued in U.S. Appl. No. 14/303,895; dated May 21, 2015, pp. 1-11.
Non-Final Rejection issued in U.S. Appl. No. 14/303,895; dated Sep. 9, 2015, pp. 1-12.

(56) References Cited

OTHER PUBLICATIONS

Non-Final Rejection issued in U.S. Appl. No. 13/467,757; dated Apr. 17, 2013, pp. 1-9.
Non-Final Rejection issued in U.S. Appl. No. 13/468,422; dated Jun. 4, 2014, pp. 1-24.
Non-Final Rejection issued in U.S. Appl. No. 13/468,422; dated Mar. 27, 2013, pp. 1-27.
Non-Final Rejection issued in U.S. Appl. No. 13/468,422; dated Sep. 16, 2013, pp. 1-19.
Non-Final Rejection issued in U.S. Appl. No. 13/382,772; dated Apr. 10, 2013, pp. 1-48.
Non-Final-Rejection issued in U.S. Appl. No. 13/432,811; dated Apr. 8, 2013, pp. 1-7.
Non-Final-Rejection issued in U.S. Appl. No. 13/432,811; dated Jul. 29, 2014, pp. 1-8.
Non-Final-Rejection issued in U.S. Appl. No. 13/432,811; dated Sep. 9, 2015, pp. 1-11.
Novolog® product information, Oct. 2009, pp. 1-4.
NovoMix® prescribing information, Feb. 2011, pp. 1-5.
NovoRapid® prescribing infonnation, Jul. 2012, pp. 1-5.
Organization for Economic Co-Ooperation and Development; OECD Principles of Good Laboratory Practice and Compliance Monitoring (as revised in 1997); ENV/MC/CHEM (98)17:1-41 (Jan. 21, 1998).
Orskov C., "Glucagon-Like Peptide-1, A New Hormone of the Entero-insular Axis," Diabetologia, 1992, vol. 35 (8), pp. 701-711.
Ott P., et al., "Diabetes in Germany(Dig) Study a Prospective 4-Year-Follow-Up Study on the Quality of Treatment for Type 2 Diabetes in Daily Practice," Deutsche Medizinische Wochenschrift, 2009, vol. 134 (7), pp. 291-297, English Absract submitted.
Park C.W., et al., "PPARalpha Agonist Fenofibrate Improves Diabetic Nephropathy in Db/Db Mice," Kidney International, Published Online Mar. 1, 2006, vol. 69 (9), pp. 1511-1517.
Parkin "Guideline for Management of Postmeal Glucose" International Diabetes Federation, pp. 1-32 (Oct. 2007).
Patel & Advance Collaborative Group, "Effects of a Fixed Combination of Perindopril and indapamide on Macrovascular and Microvascular Outcomes in Patients with Type 2 Diabetes Mellitus (the Advance Trial): A Randomised Controlled Trial," Lancet, 2007, vol. 370 (9590), pp. 829-840.
Patel K., et al., "Chemical Pathways of Peptide Degradation. II. Kinetics of Deamidation of an Asparaginyl Residue in a Model Hexapeptide," Pharmaceutical Research, 1990, vol. 7 (8), pp. 703-711.
Pederson R.A., et al., "Improved Glucose tolerance in Zucker Fatty Rats by oral Administration of the Dipeptidyl Peptidase IV inhibitor Isoleucine Thiazolidide," Diabetes, 1998, vol. 47 (8), pp. 1253-1258.
Perfetti R., "Combining Basal Insulin Analogs with Glucagon-Like Peptide-1 Mimetics," Diabetes Technology & Therapeutics, 2011, vol. 13 (9), pp. 873-881.
Perry T., et al., "A Novel Neurotrophic Property of Glucagon-Like Peptide 1: A Promoter of Nerve Growth Factor-Mediated Differentiation in PC12 Cells," The Journal of Pharmacology and Experimental Therapeutics, 2002, vol. 300 (3), pp. 958-966.
Perry T., et al., "Evidence of GLP-1-Mediated Neuroprotection in an Animal Model of Pyridoxine-induced Peripheral Sensory Neuropathy," Experimental Neurology, 2007, vol. 203 (2), pp. 293-301.
Perry T., et al., "Protection and Reversal of Excitotoxic Neuronal Damage by Glucagon-Like Peptide-1 and Exendin-4," The Journal of Pharmacology and Experimental Therapeutics, 2002, vol. 302 (3), pp. 881-888.
Perry T., et al., "The Glucagon-Like Peptides: A Double-Edged therapeutic Sword?," Trends in Pharmacological Sciences, 2003, vol. 24 (7), pp. 377-383.
Perry T.A., et al., "A New Alzheimer's Disease interventive Strategy: GLP-1," Current Drug Targets, Aug. 2004, vol. 5 (6), pp. 565-571.
Pillion D.J., et al., "Dodecylmaltoside-Mediated Nasal and Ocular Absorption of Lyspro-Insulin: Independence of Surfactant from Multimer Dissociation," Pharmaceutical Research, Oct. 1998, vol. 15(10), pp. 1637-1639.
Pinget M., et al., "Efficacy and safety of lixisenatide once daily versus placebo in type 2 diabetes insufficiently controlled on pioglitazone (GetGoal-P)," Diabetes,61(Supp 1):A258, Poster 1010-P (Jun. 2012).
Pi-Sunyer F.X., "The Effects of Pharmacologic Agents for Type 2 Diabetes Mellitus on Body Weight," Postgraduate Medicine, Jul. 2008, vol. 120 (2), pp. 5-17.
Pohl M., et al., "Molecular Cloning of the Heloderman and Exendin-4 cDNAs in the Lizard," The Journal of Biological Chemistry, 1998, vol. 273 (16), pp. 9778-9784.
Porter D.W., et al., "Four Weeks Administration of Liraglutide Improves Memory and Learning as Well as Glycaemic Control in Mice with High Fat Dietary-induced Obesity and Insulin Resistance," Diabetes, Obesity and Metabolism, 2010, vol. 12 (10), pp. 891-899.
Pradier L et al. "Animal Models of Alzheimer's disease." Demences (Dementias); eds. Duyckaerts C. and Pasquier F.; publisher Doin; 165-170 (Sep. 10, 2002; available Aug. 27, 2002).
Prandini N., "Methods of Measuring Gallbladder Motor Functions—the Need for Standardization: Scintigraphy," Digestive and Liver Disease, 2003, vol. 35 (Suppl 3), pp. S62-S66.
"Preferable." Merriam-Webster.com. Merriam-Webster, n.d. Web. Sep. 7, 2015. http://www.merriamwebster.com/dictionary/preferable).
Pugeat M., et al., "Insulin Resistance, Polycystic Ovary Syndrome and Metformin," Drugs, Sep. 1999, vol. 58 (Suppl 1), pp. 41-46.
Quianzon C.L., et al., "Lixisentide-Once Daily Glucagon-Like Peptide-1 Receptor Agonist in the Management of Type 2 Diabetes," US Endocrinology, 2011, vol. 7 (2), pp. 104-109, (Winter 2011).
Raccah D., et al., "When Basal Insulin therapy in Type 2 Diabetes Mellitus is not Enough—What Next?," Diabetes/Metabolism Research and Reviews, Published Online Feb. 21, 2007, vol. 23 (4), pp. 257-264.
Raju R.P., et al., "Optimum Palliation of inoperable Hilar Cholangiocarcinoma: Comparative Assessment of the Efficacy of Plastic and Self-Expanding Metal Stents," Digestive Diseases and Sciences, published online, Jan. 11, 2011, vol. 56, pp. 1557-1564.
Ramos B., et al., "Early Neuropathology of Somatostatin/NPY Gabaergic Cells in the Hippocampus of a Ps1xAPP Transgenic Model of Alzheimer's Disease," Neurobiology of Aging, 2006, vol. 27 (11), pp. 1658-1672.
Rao A.D., et al., "Is the Combination of Sulfonylureas and Metformin Associated with an increased Risk of Cardiovascular Disease or all-Cause Mortality? A Meta-Analysis of Observational Studies," Diabetes Care, 2008, vol. 31 (8), pp. 1672-1678.
Ratner R.E., et al., "Dose-Dependent Effects of the Once-Daily GLP-1 Receptor Agonist Lixisenatide in Patients with Type 2 Diabetes Inadequately Controlled with Metformin: A Randomized Double-Blind, Placebo-Controlled Trial," Diabetic Medicine, Sep. 2010, vol. 27 (9), pp. 1024-1032.
Ratner R.E., et al., "Post-Meal Pharmacodynamics Profile of Ave0010, a Once-Daily GLP-1 Receptor Agonist, in Patiens with Type 2 Diabetes Inadequately Controlled on Metformin," Diabetologia, Sep. 2009, vol. 52 (Suppl 1), pp. S60. Abstract 131.
Ratner R.E., et al., "Abstract # 433-P, a Dose-Finding Study of the New GLP-1 Agonist AVE0010 in Type 2 Diabetes Insufficiently Controlled with Metformin," Diabetes, Poster, 68th Annual Meeting of the American Diabetes Association, San Francisco, Jun. 6-10, 2008, vol. 57 (Suppl 1), p. A129.
Raufman J.P., "Bioactive Peptides from Lizard Venoms," Regulatory peptides, 1996, vol. 61 (1), pp. 1-18.
Request for "Type C" Meeting letter sent by Michael Lutz addressed to Mary Parks, dated Apr. 21, 2006, pp. 1-10.
Richter, von Margret, "Oldtimer as Newcomer" Pharmazie, pp. 1-9; http://www.pharmazeutische-zeitung.de/pza/2002-12/pharm1.htm (Feb. 2002).
Riddle M., et al., "Contributions of Basal and Postprandial Hyperglycemia over a Wide Range of A 1 C Levels before and after

(56) References Cited

OTHER PUBLICATIONS

Treatment Intensification in Type 2 Diabetes," Diabetes Care, Published Online Oct. 25, 2011, vol. 34, pp. 2508-2514.
Riddle M.C., et al., "Adding Once-Daily Lixisenatide for Type 2 Diabetes Inadequately Controlled by Established Basal Insulin: A 24-Week, Randomized, Placebo-Controlled Comparison (Getgoal-L)," Diabetes Care, Sep. 2013, vol. 36 (9), pp. 2489-2496.
Riddle M.C., et al., "Adding once-Daily Lixisenatide for Type 2 Diabetes inadequately Controlled with Newly initiated and Continuously Titrated Basal Insulin Glargine," Diabetes Care, Sep. 2013, pp. 2497-2503.
Ritzel U., et al., "A Synthetic Glucagon-Like Peptide-1 Analog with Improved Plasma Stability," The Journal of Endocrinology, 1998, vol. 159 (1), pp. 93-102.
Rohrmann C.A., "Differential Diagnosis of Pancreatic and Biliary Duct Diseases," Diseases of the Abdomen and Pelvis Syllabus, 1999, pp. 170-174.
Rosenstock J., et al., "Efficacy and Safety of Lixisenatide Once Daily vs Exenatiide Twice Daily in Type 2 DM Inadequately Controlled on Metformin (GetGoal-X)," 71st Scientific Sessions, Nov. 2011. Poster.
Rosenstocket al., Abstract 145 "Dose Range Effects of the New Once Daily GLP-1 Receptor Agonist AVE0010 Added to Metformin in Type 2 Diabetes," Diabetologia, Sep. 2008, vol. 51 (Suppl 1), pp. S66.
Rosenstocket al., "Post-Meal Effects of AVE0010, a Once-Daily GLP-1 Receptor Agonist, in Type 2 Diabetes Inadequately Controlled on Metformin," Diabetes, Jun. 1, 2009, vol. 58 (Suppl 1), pp. A151-A152. Abstract 564P.
Rubino A., et al., "Delayed initiation of Subcutaneous Insulin therapy after Failure of oral Glucose-Lowering Agents in Patients with Type 2 Diabetes: A Population-Based Analysis in the UK," Diabetic Medicine, 2007, vol. 24 (12), pp. 1412-1418.
Sampson H.A., et al., "Second Symposium on the Definition and Management of Anaphylaxis: Summary Report—Second National institute of Allergy and infectious Disease/Food Allergy and Anaphylaxis Network Symposium," The Journal of Allergy and Clinical Immunology, 2006, vol. 117 (2), pp. 391-397.
Sanger F., et al., "The Amide Groups of Insulin," The Biochemical Journal, 1955, vol. 59 (3), pp. 509-518.
Sanofi and Zealand Pharma Press Release (Evaluate), "Additional Positive Results from Global Phase III Program With Lixisenatide for Type 2 Diabetes", (Apr. 12, 2011) pp. 1-3.
Sanofi's Lantus Draft Prescribing Information/Package Insert: "NDA 21-081 Draft package insert" (Sponsor revision #5) Date of submission: Apr. 20, 2000; see http://www.drugbank.ca/system/fds_labels/DB00047.pdf 1265922812; pp. 1-14.
Sanofi Press Release entitled "FDA Accepts Sanofi's New Drug Application for Basal Insulin Toujeo®," dated Jul. 8, 2014, pp. 1-2.
Sanofi Press Release; "Lyxumia (lixisenatide) in Combination with Basal insulin plus Oral Anti-Diabetics Significantly Reduced HbA1c and Post-Prandial Glucose"; Paris, France (Jun. 9, 2012) pp. 1-6.
Sanofi Press Release (Peron and Schaeffer), "Sanofi GetGoal Program on Lyxumia®, as an Add-on to Basal Insulin, Shows Significant Positive Phase III Results," Paris, France (May 31, 2011) pp. 1-2.
Sanofi Press release (Peron and Schaeffer); "Sanofi Reports Positive Results for Once-daily Lyxumia® (lixisenatide) in Combination with Lantus® (insulin glargine) in Type 2 Diabetes" Paris, France (Dec. 6, 2011) pp. 1-3.
Sanofi Press Release (Peron and Schaeffer), "Lyxumia® (lixisenatide) One-Step Regimen as Effective as Two-Step Regimen in Improving Glycemic Control in Type 2 Diabetes" Paris, France (Sep. 12, 2011) pp. 1-3.
Sanofi Press Release "Positive Results for Investigational Compound Lyxumia (Lixisenatide) Presented at American Diabetes Association's 71st Annual Scientific Sessions," (Jun. 24, 2011), pp. 1-5.
Sanofi Press Release (Sigurd), "Lixisenatide Significantly Reduces HbA1c Without Increasing Hypoglycemia in Patients Uncontrolled on Sulfonylureas", Pressmeddelande (Apr. 12, 2011) pp. 1-2.
Sanofi-aventis Press Release (Gabriel), "New Diabetes Compound AVE0010 Showed Clear Dose Response Results With Once-A-Day Injection in Phase IIb Study" Paris, France (Jun. 7, 2008) pp. 1-2.
Sanofi-aventis Press Release, "Once Daily Lixisenatide (AVE 0010) Given as Monotherapy Successfully Meets Phase III Study Endpoints in Diabetes" Paris, France (Apr. 15, 2010) pp. 1-2.
Sanofi-aventis Press Release (Peron and Schaeffer), "Sanofi-aventis Announces Positive Top-line Lixisentatide Phase III Results" Paris, France (Feb. 2, 2011) pp. 1-2.
Sanofi Press Release entitled "Sanofi Receives FDA Approval of Once-Daily Basal Insulin Toujeo®," dated Feb. 26, 2015, pp. 1-4.
Schapira A.H., "Causes of Neuronal Death in Parkinson's Disease," Advances in Neurology, 2001, vol. 86, pp. 155-162.
Schellenberger V., et al., "Attempts for Quantifying the S' Subsite Specificity of Serine Proteases, Selected Papers Presented at the 2nd International Meeting on the Molecular and Cellular Regulation of Enzyme Activity, Advances in the Biosciences, Peptides and Proteases," Recent Advances, 1987, vol. 65, pp. 159-166.
Schellenberger V., et al., "Protease-Catalyzed Kinetically Controlled Peptide Synthesis," Angewante Chemie, 1991, vol. 30 (11), pp. 1437-1449.
Schindowski K., et al., "Impact of Aging: Sporadic, and Genetic Risk Factors on Vulnerability to Apoptosis in Alzheimer's Disease," Neuromolecular Medicine, 2003, vol. 4 (3), pp. 161-178.
Schmitz C., et al., "Hippocampal Neuron Loss Exceeds Amyloid Plaque Load in a Transgenic Mouse Model of Alzheimer's Disease," The American Journal of Pathology, 2004, vol. 164 (4), pp. 1495-1502.
Schubert-Zsilavecz M., et al., "Better Blood Sugar Control in Diabetics. Insulin Glargin—A Long Acting Insulin Analogue," Pharmazie in Unserer Zeit, 2001, vol. 30 (2), pp. 125-130, With English translation.
Schwartz G.P., et al., "A Superactive Insulin: [B10-Aspartic Acid]Insulin(Human)," Proceedings of the National Academy of Sciences of the United States of America, Sep. 1987, vol. 84 (18), pp. 6408-6411.
Search Report of the Indecopi for Patent Application in Peru No. 000643-2012/DIN, dated Jul. 23, 2015, pp. 1-2.
Search Report of the Intellectual Property Corporation of Malaysia for Malaysian Patent Application No. PI 2011006204; dated Sep. 15, 2015, pp. 1-3.
Search Report of the Intellectual Property Office of Singapore for Patent Application No. 10201500871T, dated Nov. 2, 2015, pp. 1-3.
Secnik Boye K., et al., "Patient-Reported Outcomes in a Trial of Exenatide and Insulin Glargine for the Treatment of Type 2 Diabetes," Health and Quality of Life Outcomes, Oct. 2006, vol. 4 (80), pp. 1-8.
Seino Y., et al., "Report of the Committee on the Classification and Diagnostic Criteria of Diabetes Mellitus," Journal of the Japan Diabetes Society, 2010, vol. 53, pp. 450-467 (in Japanese) English summary also provided.
Seino Y., et al., "Randomized, Double-Blind, Placebo-Controlled Trial of the Once-Daily GLP-1 Receptor Agonist Lixisenatide in Asian Patients with Type 2 Diabetes Insufficiently Controlled on Basal Insulin with or without a Sulfonylurea (Getgoal-L-Asia)," Diabetes, Obesity and Metabolism, 2012, vol. 14 (10), pp. 910-917.
Sharplin P., et al., "Improved Glycaemic Control by Switching from Insulin NPH to Insulin Glargine: A Retrospective Observational Study," Cardiovascular Diabetology, Published Jan. 19, 2009, vol. 8 (3), pp. 1-8.
Sherer T.B., et al., "Subcutaneous Rotenone Exposure Causes Highly Selective Dopaminergic Degeneration and A-Synuclein Aggregation," Experimental Neurology, 2003, vol. 179, pp. 9-16.
Sluzky V., et al., "Kinetics of Insulin Aggregation in Aqueous Solutions Upon Agitation in the Presence of Hydrophobic Surfaces," Proceedings of the National Academy of Sciences of the United States of America, Nov. 1991, vol. 88 (21), pp. 9377-9381.

(56) References Cited

OTHER PUBLICATIONS

Smolka M.B., et al., "Optimization of the Isotope-Coded Affinity Tag-Labeling Procedure for Quantitative Proteome Analysis," Analytical Biochemistry, Oct. 2001, vol. 297 (1), pp. 25-31, Abstract only submitted.

Sporn M.B., et al., "Chemoprevention of Cancer," Carcinogenesis, 2000, vol. 21 (3), pp. 535-530.

St. John Providence Health Center, "Preventing Obesity" http://www.stjohnprovidence.org/HealthInfolib/swarticle.aspx?type=85&id= P07863, Retrieved Aug. 22, 2013, pp. 1-2.

Starkova N.T., "Clinical Endocrinology," Guide for physicians, Medicine, 1991, pp. 192-262.

Stolk R.P., et al., "Insulin and Cognitive Function in an Elderly Population the Rotterdam Study," Diabetes Care, 1997, vol. 20 (5), pp. 792-795.

Summary of Product Characteristics Lyxumia 10 micrograms solution for injection, pp. 1-93, published Mar. 14, 2013.

Sundby F., "Separation and Characterization of Acid-induced Insulin Transformation Products by Paper Electrophoresis in 7 M Urea," The Journal of Biological Chemistry, Nov. 1962, vol. 237 (11), pp. 3406-3411.

Tanner C.M., et al., "Rotenone, Paraquat, and Parkinson's Disease," Environmental Health Perspectives, 2011, vol. 119 (6), pp. 866-872.

Tempero M.A., "How I Treat Pancreatic Ductal Adenocarcinoma," Current Clinical Issues, Journal of Oncology Practice, 2008, vol. 4 (1), pp. 46-47.

Teramoto S., et al., "Exendin-4, a Glucagon-Like Peptide-1 Receptor Agonist, provides Neuroprotection in Mice Transient Focal Cerebral Ischemia," Journal of Cerebral Blood Flow and Metabolism, 2011, vol. 31 ( 8), pp. 1696-1705.

Tessari P., et al., "Insulin in Methionine and Homocysteine Kinetics in Healthy Humans: Plasma Vs intracellular Models," American Journal of Physiology. Endocrinology and Metabolism, 2005, vol. 288 (6), pp. E1270-E1276.

Tetich M., et al., "Neuroprotective Effects of (24R)-1,24-Dihydroxycholecalciferol in Human Neuroblastoma SH-SY5Y Cell Line," The Journal of Steroid Biochemistry and Molecular Biology, 2004, vol. 89-90 (1-5), pp. 365-370.

Tews D., et al., "Enhanced Protection against Cytokine- and Fatty Acid-Induced Apoptosis in Lns-1 Beta-Cells by Combined Treatment with Insulin Glargine and the Novel GLP-1 Receptor Agonist Ave0010," Diabetes, 2007, vol. 56 (Suppl 1), pp. A72-A73.

Tews D., et al., "Enhanced Protection Against Cytokine- and Fatty Acid-induced Apoptosis in Pancreatic Beta Cells by Combined Treatment with Glucagon-Like Peptide-1 Receptor Agonists and Insulin Analogues," Hormone and Metabolic Research, Mar. 2008, vol. 40 (3), pp. 172-180.

The Diabetes Control and Complications Trial Research Group, "The Effect of intensive Treatment of Diabetes on the Development and Progression of Long-Term Complications in Insulin-Dependent Diabetes Mellitus," The New England Journal of Medicine, Sep. 1993, vol. 329, pp. 977-986.

Thong K.Y., et al., "Safety, Efficacy and tolerability of Exenatide in Combination with Insulin in the Association of British Clinical Diabetologists Nationwide Exenatide Audit," Diabetes, Obesity and Metabolism, 2011, vol. 13 (8), pp. 703-710.

Thurow H., et al., "Stabilisation of Dissolved Proteins against Denaturation at Hydrophobic Interfaces," Diabetologia, Aug. 1984, vol. 27 (2), pp. 212-218.

Toth M.L., et al., "Neurite Sprouting and Synapse Deterioration in the Aging Caenorhabditis Elegans Nervous System," The Journal of Neuroscience, 2012, vol. 32 (26), pp. 8778-8790.

Translation of pp. 1109, 1116 and 1117 of "Clinical Effectiveness of Long-Term Administration of BAY g5421 (Acarbose) on Insulin-Treated Diabetes," Jpn. Pharmacal. Ther; 1996 vol. 24 No. 5: 1109-1129, pp. 1-4.

Translation of pp. 121 and 124 of Igaku to Yakugaku, "Utility of Voglibose Long-term Combined Therapy in Non-Insulin Dependent Diabtetic Patients with Little Effective of Sulfonylureas," 1999, vol. 42, No. 1: 121-129, pp. 1-3.

Translation of pp. 2346 and 2348 of Rinsho to Kenkyu, "Effectiveness of Combination Therapy Using Voglibose and Insulin in Patients with NIDDM," 1997, vol. 74, No. 9: 2346-2352, pp. 1-3.

Translation of pp. 750, 753 and 754 of Igaku No Ayumi, "Incretin Receptors," May 2010, vol. 233; No. 9: 750-754, pp. 1-4.

Turner R.C., et al., "Glycemic Control with Diet, Sulfonylurea, Metformin, or Insulin in Patients with Type 2 Diabetes Mellitus: Progressive Requirement for Multiple therapies (UKPDS 49)," JAMA, 1999, vol. 281 (21), pp. 2005-2012.

Tyler-Cross R., et al., "Effects of Amino Acid Sequence, Buffers, and Ionic Strength on the Rate and Mechanism of Deamidation of Asparagine Residues in Small Peptides," The Journal of Biological Chemistry, 1991, vol. 266 (33), pp. 22549-22556.

UK Prospective Diabetes Study (UKPDS) Group, "Effect of intensive Blood-Glucose Control with Metformin on Complications in Overweight Patients with Type 2 Diabetes (UKPDS 34)," Lancet, Sep. 1998, vol. 352 (9131), pp. 854-865.

UK Prospective Diabetes Study (UKPDS) Group, "Intensive Blood-Glucose Control with Sulphonylureas or Insulin Compared with Conventional Treatment and Risk of Complications in Patients with Type 2 Diabetes (UKPDS 33)," The Lancet, Sep. 12, 1998, vol. 352, pp. 837-853.

"Suspension" Stedman's Medical Dictionary, 20th Edition, p. 1450 (Williams & Wilkins Co., Baltimore 1961).

"Suspension" Taber's Cyclopedic Medical Dictionary, 19th Edition, p. 2097 (F.A. Davis Co., Philadelphia 2001).

Uttenthal L.O., et al., "Molecular forms of Glucagon-Like Peptide-1 in Human Pancreas and Glucagonomas," The Journal of Clinical Endocrinology & Metabolism, 1985, vol. 61 (3), pp. 472-479.

Valle J., et al., "Cisplatin Plus Gemcitabine Versus Gemcitabine for Biliary Tract Cancer," The New England Journal of Medicine, Apr. 2010, vol. 362 (14), pp. 1273-1281.

Van Delden, "Pancreas-Carcinoma, CT Assessment of Resectability," Radiology Department of the Academical Medical Centre, Apr. 2006, pp. 1-12.

Varadarajan S., et al., "Review: Alzheimer's Amyloid Beta-Peptide-Associated Free Radical Oxidative Stress and Neurotoxicity," Journal of Structural Biology, 2000, vol. 130 (2-3), pp. 184-208.

Venezia V., et al., "Apoptotic Cell Death and Amyloid Precursor Protein Signaling in Neuroblastoma SH-SY5Y Cells," Annals of the New York Academy of Sciences, 2004, vol. 1030, pp. 339-347.

Victoza® ANNEX I—Summary of product characteristics. First published 2009, pp. 1-32.

Victoza Press Release, "Diabetes drugs show promise in Alzheimer's" published Jan. 17, 2011, pp. 1-2.

Victoza® Product information—European Medicines Agency, first published Aug. 7, 2009, pp. 1-2.

Volund A., et al., "In Vitro and in Vivo Potency of Insulin Analogues Designed for Clinical Use," Diabetic Medicine, Nov. 1991, vol. 8 (9), pp. 839-847.

Vora J., et al., "Incretin-Based therapy in Combination with Basal Insulin: A Promising Tactic for the Treatment of Type 2 Diabetes," Diabetes & Metabolism, 2013, vol. 39 (1), pp. 6-15.

Wafa W.S., et al., "Use of U-500 Regular Insulin in Type 2 Diabetes," Diabetes Care, 2006, vol. 29 (9), pp. 2175-2176.

Wajchenberg B.L., "Clinical Approaches to Preserve Beta-Cell Function in Diabetes," Advances in Experimental Medicine and Biology, 2010, vol. 654, pp. 515-535.

Wan Z., et al., "Enhancing the Activity of Insulin at the Receptor Interface: Crystal Structure and Photo-Cross-Linking of A8 Analogues," Biochemistry, 2004, vol. 43 (51), pp. 16119-16133.

Wang L., et al., "Real-World Outcomes of US Employees with Type 2 Diabetes Mellitus Treated with Insulin Glargine or Neutral Protamine Hagedorn Insulin: A Comparative Retrospective Database Study," BMJ Open, 2013, vol. 3 (4), pp. e002348 1-e002348 9.

Ward J.D., "Diabetic Neuropathy," British Medical Bulletin, Jan. 1989, vol. 45 (1), pp. 111-126.

Watson G.S., et al., "Insulin increases CSF Abeta42 Levels in Normal Older Adults," Neurology, 2003, vol. 60 (12), pp. 1899-1903.

(56) References Cited

OTHER PUBLICATIONS

Weiss M.A., et al., "Activities of Monomeric Insulin Analogs at Position A8 are Uncorrelated with their thermodynamic Stabilities," The Journal of Biological Chemistry, 2001, vol. 276 (43), pp. 40018-40024.

Werner et al., "Abstract, Insulin Glargine U-100 Has a Favourable Time-Action Profile Compared to U-40 or NPH Insulin in Healthy, Normoglycaemic Dogs", Poster 37th Annual Meeting of Endocrine Society of India, Tirupati, A.P., India, ESICON, 2007, p. 2, (2 Pages Including Abstract and Poster).

Werner U., et al., "Pharmacological Profile of Lixisenatide: A New GLP-1 Receptor Agonist for the Treatment of Type 2 Diabetes," Regulatory Peptides, Epub Jun. 2, 2010, vol. 164 (2-3), pp. 58-64.

Weyer C., et al., "Long-Term Changes in Insulin Action and Insulin Secretion Associated with Gain, Loss, Regain and Maintenance of Body Weight," Diabetologia, Jan. 2000, vol. 43 (1), pp. 36-46.

White I.R., et al., "Randomized Clinical Trials with Added Rescue Medication: Some Approaches to their Analysis and interpretation," Statistics in medicine, 2001, vol. 20 (20), pp. 2995-3008.

Whittingham J.L., et al., "Insulin at pH 2: Structural Analysis of the Conditions Promoting Insulin Fibre formation," Journal of Molecular Biology, 2002, vol. 318 (2), pp. 479-490.

WHO BMI classification, accessed at URL apps.who.int/bmi/index.jsp?introPage=itrol_3.html, Sep. 9, 2013, one page.

WHO Drug Information vol. 22(2), list 99, p. 142 (lixisenatide) (Jul. 2008).

WHO Rational Use of Medicines, http://www.who.int/medicines/areas/rational_use/en/downloaded Dec. 18, 2014 (2012).

Widjaja A., et al., "UKPDS 20: Plasma Leptin, Obesity, and Plasma Insulin in Type 2 Diabetic Subjects," The Journal of Clinical Endocrinology and Metabolism, 1997, vol. 82 (2), pp. 654-657.

Wiernsperger N.F., et al., "The Antihyperglycaemic Effect of Metformin: Therapeutic and Cellular Mechanisms," Drugs, Sep. 1999, vol. 58 (Suppl 1), pp. 31-39.

Wirths O., et al., "Intraneuronal Abeta Accumulation Precedes Plaque formation in beta-Amyloid Precursor Protein and Presenilin-1 Double-Transgenic Mice," Neuroscience Letters, 2001, vol. 306 (1-2), pp. 116-120.

Wirths O., et al., "Intraneuronal APP/A Beta Trafficking and Plaque formation in Beta-Amyloid Precursor Protein and Presenilin-1 Transgenic Mice," Brain Pathology, 2002, vol. 12 (3), pp. 275-286.

Wirths O., et al., "Reelin in Plaques of Beta-Amyloid Precursor Protein and Presenilin-1 Double-Transgenic Mice," Neuroscience Letters, 2001, vol. 316 (3), pp. 145-148.

Wollen K.A., "Alzheimer's Disease: the Pros and Cons of Pharmaceutical, Nutritional, Botanical, and Stimulatory therapies, with a Discussion of Treatment Strategies from the Perspective of Patients and Practitioners," Alternative Medicine Review, 2010, vol. 15 (3), pp. 223-244.

Written Opinion of the ISA for International Application No. PCT/EP2011/058079, dated Mar. 22, 2012, pp. 1-8.

Xie H., et al., "Characterization of Protein Impurities and Site-Specific Modifications Using Peptide Mapping with Liquid Chromatography and Data Independent Acquisition Mass Spectrometry," Analytical Chemistry, Jul. 2009, vol. 81 (14), pp. 5699-5708.

Yki-Jarvinen H., et al., "Insulin Glargine or Nph Combined with Metformin in Type 2 Diabetes: The Lanmet Study," Diabetologia, Mar. 2006, vol. 49 (3), pp. 442-451.

Yki-Jarvinen H., "Thiazolidinediones," The New England Journal of Medicine, Sep. 2004, vol. 351 (11), pp. 1106-1118.

Yoon N.M., et al., "Exenatide Added to Insulin therapy: A Retrospective Review of Clinical Practice Over Two Years in an Academic Endocrinology Outpatient Setting," Clinical Therapeutics, 2009, vol. 31 (7), pp. 1511-1523.

Yu Z.P., et al., "Effect of Zinc Sulphate and Zinc Methionine on Growth, Plasma Growth Hormone Concentration, Growth Hormone Receptor and Insulin-Like Growth Factor-I Gene Expression in Mice," Clinical and Experimental Pharmacology & Physiology, 2005, vol. 32 (4), pp. 273-278, Abstract only.

Zealand Pharma Press Release entitled "Sanofi-Aventis finalize phase IIa clinical study with GLP-1 agonist for type 2 diabetes licensed from Zealand Pharma" dated Mar. 3, 2005, one page.

Ziemer D.C., et al., "Clinical Inertia Contributes to Poor Diabetes Control in a Primary Care Setting," The Diabetes Educator, 2005, vol. 31 (4), pp. 564-571.

Ziessman H.A., et al., "Sincalide-Stimulated Cholescintigraphy: A Multicenter Investigation to Determine Optimal Infusion Methodology and Gallbladder Ejection Fraction Normal Values," Journal of Nuclear Medicine, Feb. 2010, vol. 51 (2), pp. 277-281.

Zimmet P., et al., "Clinical Efficacy of Metformin Against Insulin Resistance Parameters: Sinking the Iceberg," Review Article, Drugs, Sep. 1999, vol. 58 (Suppl 1), pp. 21-28.

Zinman B., et al., "Efficacy and Safety of the Human Glucagon-Like Peptide-1 Analog Liraglutide in Combination with Metformin and Thiazolidinedione in Patients with Type 2 Diabetes (LEAD-4 Met+TZD)," Diabetes Care, Jul. 2009, vol. 32 (7), pp. 1224-1230.

Zinman B., "The Physiologic Replacement of Insulin an Elusive Goal," The New England Journal of Medicine, Aug. 1989, vol. 321 (6), pp. 363-370.

U.S. Appl. No. 13/382,772, filed May 29, 2012, Schoettle.
U.S. Appl. No. 13/382,442, filed Feb. 21, 2012, Schoettle.
U.S. Appl. No. 13/509,507, filed Jul. 30, 2014, Brunner-Schwarz et al.
U.S. Appl. No. 13/509,542, filed Aug. 2, 2012, Hagendorf et al.
U.S. Appl. No. 14/172,151, filed Feb. 4, 2014, Bley et al.
U.S. Appl. No. 12/617,805, filed Nov. 13, 2009, Silvestre et al.
U.S. Appl. No. 12/617,811, filed Nov. 13, 2009, Silvestre et al.
U.S. Appl. No. 14/220,562, filed Mar. 20, 2014, Becker et al.
U.S. Appl. No. 13/700,631, filed Nov. 11, 2012, Becker et al.
U.S. Appl. No. 13/819,114, filed Apr. 29, 2013, Boka et al.
U.S. Appl. No. 13/363,956, filed Feb. 1, 2012, Silvestre et al.
U.S. Appl. No. 13/432,811, filed Mar. 28, 2012, Boka et al.
U.S. Appl. No. 13/469,633, filed May 11, 2012, Ruus et al.
U.S. Appl. No. 13/467,707, filed May 9, 2012, Niemoller et al.
U.S. Appl. No. 13/468,422, filed May 10, 2012, Silvestre et al.
U.S. Appl. No. 13/467,757, filed May 9, 2012, Silvestre et al.
U.S. Appl. No. 13/595,590, filed Aug. 27, 2012, Niemoller et al.
U.S. Appl. No. 13/602,913, filed Sep. 4, 2012, Hess et al.
U.S. Appl. No. 13/633,563, filed Oct. 2, 2012, Stechl et al.
U.S. Appl. No. 14/965,586, filed Dec. 10, 2015, Souhami et al.
U.S. Appl. No. 14/995,910, filed Jan. 14, 2016, Bergmann et al.
U.S. Appl. No. 15/068,286, filed Mar. 11, 2016, Roy et al.
U.S. Appl. No. 13/123,835, filed Sep. 30, 2011, Werner et al.
U.S. Appl. No. 13/633,496, filed Oct. 2, 2012, Stechl et al.
U.S. Appl. No. 13/661,476, filed Oct. 26, 2012, Silvestre et al.
U.S. Appl. No. 14/303,895, filed Jun. 13, 2014, Souhami et al.
U.S. Appl. No. 15/073,364, filed Mar. 17, 2016, Belder et al.

Jones et al., "Effect of metformin in pediatric patients with type 2 diabetes: a randomized controlled trial." Diabetes Care 25(1):89-94 (Jan. 2002).

Juniper et al., "Determining a minimal important change in a disease-specific quality of life questionnaire." J Clin Epidemiol 47(1):81-87 (Jan. 1994).

Kelly et al., "Systematic review: glucose control and cardiovascular disease in type 2 diabetes." Ann Intern Med 151 (6):394-403 (Sep. 2009; Epub Jul. 20, 2009).

Kendall et al., "Clinical Application of Incretin-Based Therapy: Therapeutic Potential, Patient Selection and Clinical Use." European Journal of Internal Medicine. 20(Suppl 2):S329-39 (Jul. 2009).

Khaw et al., "Glycated haemoglobin, diabetes, and mortality in men in Norfolk cohort of European Prospective Investigation of cancer and Nutrition (EPIC Norfolk)." BMJ 322(7277):15-18 (Jan. 2001).

Kim et al., "Retinopathy in Monkeys with Spontaneous Type 2 Diabetes" Investigative Opth & Visual Science, 45 (12):4543-53 (Dec. 2004).

King et al., Global burden of diabetes, 1995-2025. Prevalence, numerical estimates and projections. Diabetes Care 21(9)1414-31 (Sep. 1998).

Kolotkin et al., "Assessing impact of weight on quality of life." Obes Res. 3(1):49-56 (Jan. 1995).

(56) References Cited

OTHER PUBLICATIONS

Kolotkin et al., "Development of a brief measure to assess quality of life in obesity." Obes Res. 9(2):102-11 (Feb. 2001).

Кондратьев В.А. Методические указания, May 5, 2010,c. 5 (Kondrat'ev V.A. Methodical Guidelines, May 7, 2010, p. 5)] (in Russian only), found on Mar. 24, 2016, found from Internet: StudFields.ru>preview/4510743).

Korytkowski, "When oral agents fail: practical barriers to starting insulin." Int J Obes Relat Metab Disord. 26 Suppl 3:S18-24 (Sep. 2002).

Lovshin & Drucker, "Incretin-based therapy for type 2 diabetes mellitus." Nat. Rev. Endocrinol. 5(5):262-69 (May 2009).

Madsbad, "Impact of postprandial glucose control on diabetes-related complications: How is the evidence evolving?" Journal of Diabetes and Its Complications, 30:374-85 (2016; available online Oct. 9, 2015).

McFarlane, "Insulin therapy and type 2 diabetes: management of weight gain," J Clin Hypertens (Greenwich). 11 (10):601-7 (Oct. 2009).

Meadows et al, "The diabetes health profile (DHP): a new instrument for assessing the psychosocial profile of insulin equiring patients: development and psychometric evaluation," Qual. Life Res. 5(2):242-54 (Apr. 1996).

Meadows et al., "Adaptation of the diabetes health profile (DHP-1) for use with patients with Type 2 diabetes mellitus: psychometric evaluation and cross-cultural comparison," Diabet. Med. 17(8):572-80 (Aug. 2000).

Meier et al., "Effect of lixisenatide vs liraglutide on glycaemic control, gastric emptying and safety parameters in optimised insuline glargine type 2 diabetes mellitus +/− metformin" Poster and Abstract 926, 50th EASD Annual Meeting, Vienna, Austria Sep. 15-19, 2014, pp. 1-3.

Meier et al., "Contrasting Effects of Lixisenatide and Liraglutide on Postprandial Glycemic Control, Gastric Emptying, and Safety Parameters in Patients With Type 2 Diabetes on Optimized Insulin Glargine With or Without Metformin: A Randomized, Open-Label Trial" Diabetes Care 38(7):1263-73 (Jul. 2015).

Merck Index, "Metformin", The Merck Index, 15th Edition (2013), RSC Publishing, 4 pages submitted, p. 1102.

Miyazaki et al., "Improved glycemic control and enhanced insulin sensitivity in type 2 diabetic subjects treated with pioglitazone", Diabetes Care, 24(4):710-19 (Apr. 2001).

Monnier et al., "Postprandial and Basal Glucose in Type 2 Diabetes: Assessment and Respective Impacts" Diabetes Technology & Therapeutics, 13(Supplement 1):S25-S32 (2011).

Monnier & Colette, "Addition of rapid-acting insulin to basal insulin therapy in type 2 diabetes: indications and modalities." Diabetes Metab 32(1):7-13 (Feb. 2006).

Nathan et al., "Medical Management of Hyperglycemia in Type 2 Diabetes: A Consensus Algorithm for the Initiation and Adjustment of Therapy" Diabetes Care 32(1):193-203 (Jan. 2009).

Nathan et al., "Modern-day clinical course of type 1 diabetes mellitus after 30 years' duration: the diabetes control and complications trial/epidemiology of diabetes interventions and complications and Pittsburgh epidemiology of diabetes complications experience (1983-2005)." Arch Intern Med. 169(14):1307-16 (Jul. 2009).

NCT00866658 ClinicalTrials.gov, "GLP-1 agonist AVE0010 in patients with type 2 diabetes for glycemic control and safety evaluation, on top of basil insulin +/− sulfonylurea" p. 1-3, accessed Mar. 16, 2016 (updated Jan. 19, 2010).

NCT01169779, Clinical Trials.gov, "Efficacy and Safety of Lixisenatide in Patients with Type 2 diabetes mellitus insufficiently controlled by metformin," pp. 1-3, accessed Mar. 16, 2016 (updated Mar. 28, 2011).

NCT00713830, Clinical Trials.gov "GLP-1 Agonist in Patients with Type 2 Diabetes for Glycemic Control and Safety Evaluation, on Top of Sulfonylurea" pp. 1-3, accessed Mar. 16, 2016 (updated Jul. 13, 2008).

Nice, National Institute for Health and Care Excellence, "Evidence summary: new medicine, ESNM26: Type 2 diabetes: lixisenatide; Key points from the evidence" pp. 1-26 (Sep. 24, 2013).

NIH, National Institute of Diabetes and Digestive and Kidney Disease, "Hypoglycimia" pp. 1-8, accessed Mar. 16, 2016.

Nihonn-Iyakuhin-shu Iryoyaku "Pioglitazone hydrochloride, Insulin sensitizing hypoglycemic agent" 2009 Edition, Jiho Inc. p. 1901 (2009).

Nilsson et al., "Effects of GI vs content of cereal fibre of the evening meal on glucose tolerance at a subsequent standardized breakfast." Eur. J Clin Nutr. 62:712-20 (2008; epub May 23, 2007).

Nowels et al., "Validation of the EQ-50 quality of life instrument in patients after myocardial infarction." Qual Life Res 14(1):95-105 (Feb. 2005).

Olansky "Do incretin-based therapies cause acute pancreatitis?" J Diabetes Technol. 4(1):228-29 (Jan. 2010).

Park et al., "Long-term treatment of glucagon-like peptide-1 analog exendin-4 ameliorates diabetic nephropathy through improving metabolic anomalies in db/db mice." J Am Soc Nephrol, 18(4):1227-38 (Apr. 2007; Epub Mar. 14, 2007).

Pinhas-Hamiel & Zeitler, "Clinical presentation and treatment of type 2 diabetes in children." Pediatric Diabetes 8(9)16-27 (Dec. 2007).

Pi-Sunyer, "The Impact of Weight Gain on Motivation, Compliance, and Metabolic Control in Patients with Type 2 Diabetes Mellitus." Postgrad Med. 121(5):94-107 (Sep. 2009).

Ratner et al., "Efficacy and safety of lixisenatide once-daily versus placebo in patients with type 2 diabetes mellitus insufficiently controlled on sulfonylurea +/− metformin (GetGoal-S)" Presentation Abstract for Presentation No. 785. 47th EASD Annual Meeting, Lisbon, Sep. 12-16, 2011, pp. 1-3.

Ray et al., "Effect of intensive control of glucose on cardiovascular outcomes and death in patients with diabetes mellitus: a meta-analysis of randomized controlled trials." Lancet 373(9677):1765-72 (May 2009).

Register of medicaments (RM), 2003, issue 10, p. 517.

Remington: The Science and Practice of Pharmacy, Twentieth Edition, Lippincott Williams & Wilkins, USA, "Pancreatic Disorders" pp. 1081-1082 and "Metformin Hydrochloride" p. 1375; 2000.

Remington: The Science and Practice of Pharmacy, Twentieth Edition, Lippincott Williams & Wilkins, USA, "Oral Hypoglycemic and Hyperglycemic Drugs" pp. 1373 and 1375; 2000.

Rosenstock J et al., Advancing Basal Insulin Glargine with Prandial Lixisenatide QD vs. Insulin Glulisine QD or TID in T2DM: The GetGoalDuo2 Evidence-Based Trial (NCT01768559). Poster 107-LB, Presented on Sunday, Jun. 7, 2015, 75th Scientific Sessions of the American Diabetes Association, Boston, Massachusetts Jun. 5-9, 2015.

Russell-Jones & Khan, Insulin-associated weight gain in diabetes: causes, effects and coping strategies. Diabetes Obes Metab. 9(6):799-812 (Nov. 2007).

Sanofi-aventis Press Release, "A promising R&D portfolio, well positioned to deliver future growth" (dated Sep. 17, 2007) pp. 1-11.

Schernthaner et al., "Is the ADA/EASD algorithm for the management of type 2 diabetes (Jan. 2009) based on evidence or opinion? A critical analysis." Diabetologia.53(7):1258-69 (Jul. 2010; Epub Mar. 31, 2010).

Schwartz et al., "New Equations to Estimate GFR in Children with CKD." J Am Soc Nephrol. 20(3):629-37 (Mar. 2009; epub Jan. 21, 2009).

Seino et al., "Lixisenatide significantly improves glycemic control in Asian patients with T2DM insufficiently controlled on basal insulin ± SU." Diabetes, Abstract book for 71st Scientific Session. p. A76; Abstract 278-OR (2011).

Shaw et al., "US valuation of the EQ-5D health states: development and testing of the D1 valuation model." Med Care 43(3):203-20 (Mar. 2005).

Spertus et al., "Monitoring the quality of life in patients with coronary heart disease." Am J Cardiol. 74(12):1240-44 (Dec. 1994).

Spertus et al., "Development and evaluation of the Seattle Anginal Questionnaire: a new functional status measure for coronary artery disease." J Am Coli Cardiol. 25(2):333-41 (Feb. 1995).

(56) References Cited

OTHER PUBLICATIONS

Abraira et al., "Glycaemic separation and risk factor control in the Veterans Affairs Diabetes Trial: an interim report." Diabetes Obes Metab 11(2)150-56. (2009; Epub Jul. 29, 2008).

American Diabetes Association, "Type 2 diabetes in children and adolescents." Diabetes Care 23(3):381-89 (Mar. 2000).

American Diabetes Association, "Standards of Medical Care in Diabetes—2011", Diabetes Care, 34 (Supplement 1): S11-S61 (Jan. 2011).

Ahualli "The Double Duct Sign" Radiology 244(1):314-5 (Jul. 2007).

Ampudia-Blasco et al., "Basal Plus Basal-Bolus approach in type 2 diabetes." Diabetes Technol Ther. 13 Suppl 1: 575-83 (Jun. 2011).

Aquiliante, "Sulfonylurea pharmacogenomics in type 2 diabetes: the influence of drug target and diabetes risk polymorphisms" Expert Rev Cardiovasc Ther. 8(3):359-72 (Mar. 2010).

Atkinson et al., "Validation of a general measure of treatment satisfaction, the Treatment Satisfaction Questionnaire for Medication (TSQM), using a national panel study of chronic disease." Health Qual Life Outcomes. 2:12, pp. 1-13 (Feb. 2004).

Beckman et al., "Diabetes and atherosclerosis: epidemiology, pathophysiology, and management." JAMA 287 (19):2570-81 (May 2002).

Brazier et al., "Testing the validity of the Euroqol and comparing it with the SF-36 health survey questionnaire." Qual Life Res 2(3):169-80 (Jun. 1993).

Byetta® Summary of product characteristics. ANNEX I, pp. 1-71, (2011).

Byetta® Product information. EMA pp. 1-2, accessed Jun. 10, 2016.

Canadian Cardiovascular Society Grading of Angina Pectoris. From http://www.sscts.org/pages/classificationanginaccs.aspx. Accessed May 27, 2016, one page.

Canadian Diabetes Association. Clinical Practice Guidelines Expert Committee. Canadian Diabetes Association 2008. Clinical Practice Guidelines for the Prevention and Management of Diabetes in Canada. Canadian Journal of Diabetes S162-S167 (2008).

Cannon et al. For the Pravastatin or Atorvastatin Evaluation and Infection Therapy—Thrombolysis in Myocardial Infarction Investigators. "Intensive versus Moderate Lipid Lowering with Statins after Acute Coronary Syndromes." N Engl J Med 350(15):1495-504 (Apr. 2004; Epub Mar. 8, 2004).

Centers for Disease Control and Prevention. National diabetes fact sheet: general information and national estimates on diabetes in the United States, 2003. Rev ed. Atlanta, GA: U.S. Department of Health and Human Services, Centers for Disease Control and Prevention, pp. 1-8, 2004.

Chi et al., "Excipients and their Effects on the Quality of Biologics" pp. 1-9, (May 2012).

Classification of Functional Capacity and Objective Assessment, My.AmericanHeart, 1994—last accessed Oct. 23, 2015, pp. 1-2.

Clinical Trials History for Trial No. NCT00688701 last updated Mar. 25, 2014. Accessed at https://clinicaltrials.gov/archive/NCT00688701 Accessed on Jun. 2, 2016, pp. 1-2 submitted.

Clinical Trials Archive for Trial No. NCT00688701 updated Sep. 30, 2012. Accessed at: https://clinicaltrials.gov/archive/NCT00688701/2012_09_30/changes Accessed on Jun. 2, 2016, pp. 1-5 submitted.

D'Alessio et al., "The role of dysregulated glucagon secretion in type 2 diabetes" Diabetes, Obesity and Metabolism, 13(Suppp1.1):126-132 (Oct. 2011).

Das et al., "The British Cardiac Society Working group definition of myocardial infarction: implications for practice." Heart 92(1):21-6 (Jan. 2006; Epub Apr. 14, 2005).

DCCT, Diabetes Control and Complications Trial/ Epidemiology of Diabetes Interventions and Complications Research Group: Intensive diabetes therapy and carotid intima-media thickness in type 1 diabetes. N Engl J Med 348 (23):2294-303 (Jun. 2003).

DCCT, Diabetes Control and Complications Trial/ Epidemiology of Diabetes Interventions and Complications Research Group: Intensive diabetes treatment and cardiovascular disease in patients with type 1 diabetes. N Engl J Med. 353 (25):2643-59 (Dec. 2005).

Definition of Phase, Clinical Trials.gov NIH, accessed Mar. 16, 2016, one page.

Definition of "Combination", Concise Oxford English Dictionary, edited by A. Stevenson and M. Waite, Oxford University press, 12th Edition, Aug. 2011, 4 pages submitted, see p. 285.

De Lemos et al., "Early intensive vs. a delayed conservative simvastatin strategy in patients with acute coronary syndromes: phase Z of the A to Z trial." JAMA 292(11):1307-16 (Sep. 2004; Epub Aug. 30, 2004).

Del Prato & Tiengo, "The importance of first-phase insulin secretion: implications for the therapy of type 2 Diabetes mellitus." Diabetes Metab Res Rev. 17(3):164-74 (May-Jun. 2001).

Del Prato et al., "Global Partnership for Effective Diabetes Management. Tailoring treatment to the individual in type 2 diabetes practical guidance from the Global partnership for effective diabetes managment." Int J Clin Pract. 64 (3):295-304 (Feb. 2010).

DeWitt & Hirsch, "Outpatient insulin therapy in type 1 and type 2 diabetes mellitus: scientific review." JAMA 289 (17):2254-64 (May 2003).

Dinneen & Gerstein, "The association of microalbuminuria and mortality in non-insulin dependent diabetes mellitus. A systematic overview of the literature." Arch Intern Med 157(13):1413-8 (Jul. 1997.

Dolan, "Modeling valuations for EuroQol health states." Med Care 35(11):1095-1108 (Nov. 1997).

Druet et al., "Characterization of insulin secretion and resistance in type 2 diabetes of adolescents." J Clin Endocrinol Metab 91(2):401-404 (Feb. 2006; epub Nov. 15, 2005).

Dunning & Gerich, "The Role of alpha-cell Dysregulation in Fasting and Postprandial Hyperglycemia in Type 2 Diabetes and Therapeutic Implications" Endocrine Reviews 28(3):253-83 (Apr. 2007).

Encyclopedia of Drugs, "Metformin" Moscow, Drug Register of 2001, p. 549, English translation provided pp. 1-2.

European Medicines Agency, "Toujeo (previously Optisulin) insulin glargine," <http://www.ema.europa.eu/ema/index.jsp?curl=pages/medicines/human/medicines/000309/human_med_000955.jsp&mid=WCOb01ac058001d124>, last updated Jan. 25, 2016, visited Feb. 3, 2016, pp. 1-6—screenshot of "About" tab of webpage and printouts of "About" tab of webpage with listed items collapsed and expanded.

European Medicines Agency, Committee for Medicinal Products for Human Use (CHMP), "Assessment report—Lyxumia", pp. 1-81 (Nov. 28, 2012).

EMA—European Medicines Agency, "Note for guidance on non-clinical safety studies for the conduct of human clinical trials and marketing authorization for pharmaceuticals" pp. 1-22 (Jul. 2008).

EuroQol Group, "EuroQol—a new facility for the measurement of health-related quality of life." Health policy (Amsterdam, Netherlands) 16(3):199-208 (Dec. 1990).

FDA, Food and Drug Administration. Guidance for Industry—Diabetes Mellitus: Developing Drugs and Therapeutic Biologics for Treatment and Prevention. pp. 1-34 (Feb. 2008).

FDA—Food and Drug Administration, CFR—Code of Federal Regulations Title 21, Chapter 1, Subchapter D, Part 312.21, "Phases of an investigation" pp. 1-2, Apr. 1, 2015.

Forman et al., "Higher levels of albuminuria within the normal range predict incident hypertension." J Am Soc Nephrol 19(10):1983-88 (Oct. 2008).

Gerstein et al., "Albuminuria and risk of cardiovascular events, death, and heart failure in diabetic and nondiabetic ndividuals." JAMA 286(4):421-6 (Jul. 2001).

Gromada et al., "Alpha-Cells of the Endocrine Pancreas: 35 Years of Research but the Enigma Remains" Endocrine Reviews 28(1):84-116 (Jan. 2007).

Harkavyi & Whitton, "Glucagon-like peptide 1 receptor stimulation as a means of neuroprotection" British Journal of Pharmacology 159(3):495-501 (2010; Epub Jan. 29, 2010).

Hinnen, "Therapeutic Options for the Management of Postprandial Glucose in Patients With Type 2 Diabetes on Basal Insulin" Clinical Diabetes 33(4):175-80 (2015).

(56) References Cited

OTHER PUBLICATIONS

Holman et al., "Three-year efficacy of complex insulin regimens in type 2 diabetes." N Engl J Med. 361(18):1736-47 (Oct. 2009; Epub Oct. 22, 2009).
IDF Clinical Guidelines Task Force. Global guideline for Type 2 diabetes. Brussels: International Diabetes Federation, pp. 1-82 (Aug. 2005).
IDF, International Diabetes Federation Guideline Development Group, "Guideline for management of postmeal glucose in diabetes" Diabetes Res Clin Pract, pp. 1-13, (2012).
Inzucchi et al., "Management of hyperglycaemia in type 2 diabetes: a patient-centered approach. Position statement of the American Diabetes Association (ADA) and the European Association for the Study of Diabeters (EASD)." Diabetologia. 55(6):1577-96 (Jun. 2012; Epub Apr. 20, 2012).
Johnson et al., "Diabetes, Insulin Resistance, and Metabolic Syndrome in Horses" Journal of Diabetes Science and Technology, 6(3):534-40 (May 2012).
Spertus et al., "Health status predicts long-term outcome in outpatients with coronary disease." Circulation. 106 (1):43-49 (Jul. 2002).
Srinivasan & Ramarao, "Animal models in type 2 diabetes research: An overview." Indian J Med Res. 125:451-472 (Mar. 2007).
Standardized Definitions for Cardiovascular Outcomes Trials: Draft Recommendations. Division of Metabolism and Endocrinology Products. Center for Drug Evaluation and Research (CDER). pp. 1-34, Mar. 24, 2010.
Tanner et al., "Standards from birth to maturity for height, weight, height velocity, and weight velocity: British children, Part II." Arch Dis Child. 41(220):613-35 (1966).
The ADVANCE Collaborative Group, "Intensive blood glucose control and vascular outcomes in patients with type 2 diabetes." N Engl J Med 358(24):2560-72 (Jun. 2008).
The Criteria Committee of the New York Heart Association, "Nomenclature and Criteria for Diagnosis of Diseases of the Heart and Great Vessels." 9th edition. Boston, Mass: Little, Brown & Co; pp. 253-256 (1994).
UK Prospective Diabetes Study (UKPDS) Group, "Tight blood pressure control and risk of macrovascular and microvascular complications in type 2 diabetes (UKPDS 38)." BMJ 317:703-13 (Sep. 1998).
Weir "Glucagon-like peptide-1 (7-37) actions on endocrine pancreas." Diabetes 38(3):338-42 (Mar. 1989).
Werner et al., "The GLP-1 Receptor Agonist AVE0010 Abolishes OGTT-Induced Blood Glucose Excursion in Healthy, Normoglycemic Dog Without Risk of Hypoglycemia" Diabetes 56(Supplement 1):A129 (Jun. 2007). Abstract submitted.
WHO, World Health Organization Media Center. Obesity and overweight, Fact Sheet No. 311. Updated Jan. 2015, pp. 1-5.
WHO, World Health Organization Media Center. Diabetes Fact Sheet. Available from: http://www.who.int/mediacentre/factsheets/fs312/en/index.html. Accessed Jun. 13, 2016, pp. 1-6.
Wikipedia® entry for "Lixisenatide" Retrieved from the Internet: https://en.wikipedia.org/wiki/Lixisenatide pp. 1-2, last updated Dec. 2015.
Wikipedia® entry for "Pioglitazone" Retrieved from the Internet: https://en.wikipedia.org/wiki/Pioglitazone pp. 1-3, retrieved Apr. 11, 2016.
Wikipedia® entry for "Metformin" Retrieved from the Internet: https://en.wikipedia.org/wiki/Mefformin pp. 1-21, retrieved Apr. 11, 2016.
Wikipedia® entry for "Body mass index" Retrieved from the Internet: https://en.wikipedia.org/wiki/Body mass_index pp. 1-14, retrieved Feb. 26, 2016.
World Health Organization, "Definition, Diagnosis and Classification of Diabetes Mellitus and its Complications. Part 1: Diagnosis and Classification of Diabetes Mellitus." WHO/NCD/NCS/99.2. Geneva; pp. 1-66, (1999).
World Health Organisation report on "Definition and diagnosis of diabetes mellitus and intermediate hyperglycemia: report of a WHO/IDF consultation" pp. 1-50 (2006).
Wild et al., "Global prevalence of diabetes: estimates for the year 2000 and projections for 2030." Diabetes Care 27 (5):1047-53 (May 2004).
Williams et al., "Macrovascular disease in Diabetes." In handbook of Diabetes. 2nd ed. Williams G, Pickup JC, Eds. Oxford, UK, Blackwell Science pp. 151-158 (1999).
Wiviott et al., "Greater Clinical Benefit of More Intensive Oral Antiplatelet Therapy With Prasugrel in Patients With Diabetes Mellitus in the Trial to Assess Improvement in Therapeutic Outcomes by Optimizing Platelet Inhibition With Prasugrel-Thrombolysis in Myocardial Infarction 38." Circulation 118(16):1626-36 (Oct. 2008; Epub Aug. 31, 2008).
Wright et al., U.K. Prospective Diabetes Study Group. "Sulfonylurea inadequacy: efficacy of addition of insulin over 6 years in patients with type 2 diabetes in the UK. Prospective Diabetes Study (UKPDS 57)." Diabetes Care 25 (2):330-36 (Feb. 2002).
Yusuf et al., "Effects of clopidogrel in addition to aspirin in patients with acute coronary syndromes without ST-segment elevation." N Engl J Med 345(7):494-502 (Aug. 2001).
Zimmet et al., "Global and societal implications of the diabetes epidemic." Nature 414(6865):782-87 (Dec. 2001).
Zoungas et al, "Combined Effects of Routine Blood Pressure Lowering and Intensive Glucose Control on Macrovascular and Microvascular Outcomes in Patients With Type 2 Diabetes. New results from the ADVANCE trial." Diabetes Care 32(11):2068-74 (Nov. 2009; Epub Aug. 3, 2009).
Final Rejection issued in U.S. Appl. No. 13/382,442; dated Aug. 11, 2015, pp. 1-35.
Final Rejection issued in U.S. Appl. No. 13/382,772; dated Feb. 24, 2016, pp. 1-36.
Final Office Action from U.S. Appl. No. 12/617,805; dated May 25, 2016, pp. 1-9.
Final Rejection issued in U.S. Appl. No. 13/509,507; dated May 13, 2016, pp. 1-11.
Non-Final Rejection issued in U.S. Appl. No. 13/467,707; dated Jun. 30, 2016, pp. 1-9.
Final Rejection in U.S. Appl. No. 13/633,563; dated Apr. 8, 2016, pp. 1-12.
Final Rejection in U.S. Appl. No. 13/633,496; dated Aug. 26, 2015, pp. 1-16.
Non-Final Rejection in U.S. Appl. No. 13/633,496; dated Apr. 21, 2016, pp. 1-12.
Final Office Action issued in U.S. Appl. No. 13/602,913; dated on Apr. 2, 2015, pp. 1-7.
Non-Final Office Action issued in U.S. Appl. No. 13/602,913; dated Dec. 2, 2014, pp. 1-12.
Final Office Action issued in U.S. Appl. No. 13/602,913; dated Jun. 20, 2014, pp. 1-27.
Non-Final Office Action issued in U.S. Appl. No. 13/602,913; dated Jan. 13, 2014, pp. 1-53.
Final Office Action issued in U.S. Appl. No. 13/602,913; dated Sep. 13, 2013, pp. 1-11.
Non-Final Office Action issued in U.S. Appl. No. 13/602,913; dated May 17, 2013, pp. 1-7.
Non-Final Rejection issued in U.S. Appl. No. 13/469,633; dated Mar. 27, 2013, pp. 1-39.
Final Rejection issued in U.S. Appl. No. 14/303,895; dated Apr. 27, 2015, pp. 1-10.
English Translation of TIPO Search Report for ROC Patent Application No. 101130936, dated Dec. 1, 2015, one page.
Extended European Search Report for European Application No. 15 15 9064.3; dated Oct. 19, 2015, pp. 1-4.
U.S. Appl. No. 15/340,969, dated Nov. 1, 2016, Werner et al.
U.S. Appl. No. 15/595,929, dated May 15, 2017, Brunner-Schwarz et al.
U.S. Appl. No. 15/275,867, dated Sep. 26, 2016, Silvestre et al.
U.S. Appl. No. 15/237,285, dated Aug. 15, 2016, Boka et al.
U.S. Appl. No. 15/144,270, dated May 2, 2016, Silvestre et al.
U.S. Appl. No. 15/197,378, dated Jun. 29, 2016, Niemoller.

(56) References Cited

OTHER PUBLICATIONS

U.S. Appl. No. 15/657,683, dated Jul. 24, 2017, Souhami et al.
U.S. Appl. No. 15/646,760, dated Jul. 11, 2017, Roy et al.
Januvia—EPAR Summary for the Public, pp. 1-3 (Aug. 2012).
Karasik et al., "Sitagliptin, a DPP-4 inhibitor for the treatment of patients with type 2 diabetes: a review of recent clinical trials," Current Medical Research and Opinion 24(2):489-96 (Jan. 2008).
Katz et al., "The clinical burden of type 2 diabetes in patients with acute coronary syndromes: Prognosis implications for short- and long-term management" Diabetes and Vascular Disease Research, 11(6):395-409 (Nov. 2014).
Lantus® Drug Description, downloaded Nov. 12, 2015, one page.
Lepore et al., "Pharmacokinetics and pharmacodynamics of subcutaneous injection of long-acting human insulin analog glargine, NPH insulin, and ultralente human insulin and continuous subcutaneous infusion of insulin lispro." Diabetes 49(12):2142-48 (Dec. 2000).
Mac Conell et al., "Exenatide resulted in significantly greater improvements in postprandial glycaemic control compared to sitagliptin," Diabetologia 51(Supplement 1) p. S348, Abstract 872, one page (2008).
Mainous et al., "Impact of the population at risk of diabetes on projections of diabetes burden in the United States: epidemic on the way." Diabetologia 50(5):934-40 (May 2007; Epub Nov. 21, 2006).
Matthews et al., "Homeostasis model assessment: insulin resistance and β-cell function from fasting plasma glucose and insulin concentrations in man." Diabetologia 28(7):412-419 (Jul. 1985).
Meigs et al., "Body Mass Index, Metabolic Syndrome, and Risk of Type 2 Diabetes or Cardiovascular Disease" Journal of Clinical Endocrinology & Metabolism, 91(8):2906-12 (Aug. 2006).
Miller et al., "Type 2 diabetes in the child and adolescent", In: Lifshitz F (ed) Pediatric Endocrinology: 5th edition, vol. 1, New York, Marcel Dekker, pp. 169-188 (2007).
Mokdad et al., "The association of body mass index with the risk of type 2 diabetes: a case—control study nested in an electronic health records system in the United States." JAMA, 289(1):76-79 (Jan. 2003).
Monnier et al., "Contribution of fasting and postprandial plasma glucose increments to the overall diurnal iyperglycemia of type 2 diabetic patients: variations with increasing levels of HbA1c." Diabetes Care 26(3):881-85 (Mar. 2003).
Mudaliar & Edelman, "Insulin therapy in type 2 diabetes." Endocrinol Metab Clin North Am. 30(4):935-82 (Dec. 2001).
Nathan et al., "Medical Management of Hyperglycemia in Type 2 Diabetes: A Consensus Algorithm for the Initiation and Adjustment of Therapy. A Consensus statement of the American Diabetes Association and the European Association for the Study of Diabetes." Diabetes Care 31(1):173-75 (Jan. 2008).
Nathan et al., "Translating the A1c Assay Into Estimated Average Glucose values." Diabetes Care 31(8):1473-78 (Aug. 2008; Epub Jun. 7, 2008).
Nauck et al., "Effects of Glucagon-Like Peptide 1 on Counterregulatory Hormone Responses, Cognitive Functions, and Insulin Secretion during Hyperinsulinemic, Stepped Hypoglycemic Clamp Experiments in Healthy Volunteers." Journal of Clin. Endocrinol.& Metab. 87(3):1239-46 (Mar. 2002).
Nauck et al., "Efficacy and safety of the dipeptidyl peptidase-4 inhibitor, sitagliptin, compared with the sulfonylurea, glipizide, in patients with type 2 diabetes inadequately controlled on metformin alone: a randomized, double-blind, non-inferiority trial," Diabetes, Obesity and Metabolism, 9(2):194-205 (Mar. 2007).
NCT00976937, ClinicalTrials.gov, "24-week Study Comparing Lixisenatide (AVE0010) to Sitagliptin as add-on to Metformin in Obese Type 2 Diabetic Patients Younger Than 50," last updated Mar. 10, 2014, Retrieved Aug. 31, 2016, pp. 1-5.
Ohkubo et al., "Intensive insulin therapy prevents the progression of diabetic microvascular complications in Japanese patients with non-insulin-dependent diabetes mellitus: a randomized prospective 6-year study." Diabetes Res Clin Pract 28(2):103-17 (May 1995).
Osterbye et al., "Sulfatide promotes the folding of proinsulin, preserves insulin crystals, and mediates its monomerization." Glycobiology 11(6):473-79 (Jun. 2001).
Paniker et al., "Beneficial effects of triple drug combination of pioglitazone with glibenclamide and metformin in type 2 diabetes mellitus patients on insulin therapy," J Assoc Physicians India, 51:1061-64 (Nov. 2003).
Patel et al., "Stability Considerations for Biopharmaceuticals: Overview of Protein and Peptide Degradation Pathways" Available online at: http://www.bioprocessint.com/manufacturing/formulation/biopharmaceutical-product-stability-considerations-part-1/, 23 pages (Jan. 2011).
Petersen & Christensen et al., "Clinical potential of lixisenatide once daily treatment for type 2 diabetes mellitus" Diabetes, Metabolic Syndrome and Obesity: Targets and Therapy, 6:217-31 (Jun. 2013).
Petrie, "The cardiovascular safety of incretin-based therapies: a review of the evidence" Cardiovascular Diabetology, 12(1):130, 12 pages (Sep. 2013).
Pinget et al., "Efficacy and safety of lixisenatide once daily versus placebo in type 2 diabetes insufficiently controlled on pioglitazone (GetGoal-P)," Diabetes, Obesity and Metabolism, 15(11):1000-1007 (Nov. 2013; Epub May 26, 2013).
Raman & Heptulla, "New potential adjuncts to treatment of children with type 1 diabetes mellitus" Pediatric Research, 65(4):370-74 (Apr. 2009).
Riddle et al., "The treat-to-target trial: randomized addition of glargine or human NPH insulin to oral therapy of type 2 diabetes patients." Diabetes Care 26(11):3080-86 (Nov. 2003).
Riddle, "Combined Therapy With Insulin Plus Oral Agents: Is There Any Advantage?" Diabetes Care 31(Supplement 2):S125-S130 (Feb. 2008).
Riddle, "Timely initiation of basal insulin." Am J Med 116(Suppl 3A):3S-9S (Feb. 2004).
Rothstein et al., "Anticandida activity is retained in P-113, a 12-amino-acid fragment of histatin 5." Antimicrob Agents Chemother. 45(5):1367-73 (May 2001).
RPMI-1640 Media Formulation, Sigma Aldrich, accessed on Jul. 10, 2016, pp. 1-5.
Ruetten et al., "Protective effects of the GLP-1 receptor agonist lixisenatide on ischaemia-reperfusion-induced myocardial infarction in an isolated rat heart model" Diabetologia, Abstract 810, 54(Supplement 1):S329 (Sep. 2011).
Russell-Jones, "Current developments in the treatment of diabetes: the incretin therapies" Br J Diabetes Vasc Dis. 10:21-30 (Feb. 2010).
Sacks et al., "Guidelines and Recommendations for Laboratory Analysis in the Diagnosis and Management of Diabetes Mellitus." Clinical Chemistry 48(3):436-72 (Mar. 2002).
Sanofi, "A randomized, double- blind, placebo controlled trial to assess safety, tolerability, pharmacokinetics and pharmacodynamics of lixisentatide in pediatric (10-17 years old) and adult patients with type 2 diabetes", Sanofi, pp. 1-12 (2015). retrieved from the internet: http://en.sanofi.com/img/content/study/PKD11475_summary.pdf (retrieved on Jun. 16, 2015).
Sanofi Press Release entitled "Sanofi Announces Top-Line Results for Cardiovascular Outcomes Study of Lyxumia® (lixisenatide).", dated Mar. 19, 2015, Paris, France, pp. 1-2.
Shehadeh et al., "Can GLP-1 preparations be used in children and adolescents with diabetes mellitus?" Pediatric Endocrinology Reviews, 11(3):324-27 (Mar. 2014).
Sillars et al., "Sulphonylurea-metformin combination therapy, cardiovascular disease and all-cause mortality: the Fremantle Diabetes Study." Diabetes Obes Metab. 12(9):757-65 (Sep. 2010).
Sloop et al., "Glucagon as a target for the treatment of Type 2 diabetes." Expert Opin Ther Targets. 9(3):593-600 (Jun. 2005).
Spasov & Chepurnova, "Scientific Approaches to Combination Therapy for Type 2 Diabetes Mellitus," Bulletin of Volgograd State Medical University,1(37):8-10 (2011). See English Abstract.
Stumvoll et al., "Type 2 diabetes: Principles of pathogenesis and therapy." Lancet 365(9467):1333-46 (Apr. 2005).
Tanner & Davies, "Clinical longitudinal standards for height and height velocity for North American children." J Pediatr. 107(3):317-29 (Sep. 1985).

(56) References Cited

OTHER PUBLICATIONS

Tirosh et al., "Normal Fasting Plasma Glucose Levels and Type 2 Diabetes in Young Men" New England Journal of Medicine, 353(14):1454-62 (Oct. 2005).
UK Prospective Diabetes Study (UKPDS) Group 28: A randomized trial of efficacy of early addition of metformin in sulfonylurea-treated type 2 diabetes. Diabetes Care, 21(1):87-92 (Jan. 1998).
van Gaal et al., "Exploiting the antidiabetic properties of incretins to treat type 2 diabetes mellitus: glucagon-like peptide 1 receptor agonists or insulin for patients with inadequate glycemic control," European Journal of Endocrinology 158(6):773-84 (Jun. 2008).
van Gaal & De Leeuw, "Rationale and options for combination treatment of type 2 diabetes." Diabletologia 46 (Supplement 1):M44-M50 (Mar. 2003).
Vilsboll et al., "Liraglutide, a long-acting human glucagon-like peptide-1 analog, given as monotherapy significantly improves glycemic control and lowers body weight without risk of hypoglycemia in patients with type 2 diabetes." Diabetes Care 30(6):1608-10 (Jun. 2007; Epub Mar. 19, 2007).
Wahlin-Boll et al., "Impaired effect of sulfonylurea following increased dosage." Eur J Clin Pharmacol 22(1):21-25 (1982).
Werner, "Preclinical pharmacology of the new GLP-1 receptor agonist AVE0010", Ann. Endocrinol. (Paris), 69 (2):164-65 (Apr. 2008).
Wikipedia® entry for "Stratified sampling" Retrieved on Mar. 28, 2017, pp. 1-4.
Aguilar, "Heart failure and diabetes: Time to pay attention" American Heart Journal, 162(5):795-97 (Nov. 2011).
Ahmad & Swann, and Bloomgren "Exenatide and rare adverse events." N Engl J Med 358(18):1969-72 (May 2008).
Albert-Ludwigs University Freiburg, Institute fur Medizinische Biometrie and Statistik "Non-Inferiority Trials" dated Mar. 29, 2017, one page.
American Diabetes Association, "Diagnosis and Classification of Diabetes Mellitus", Diabetes Care, 37 (Supplement 1):S81-S90 (Jan. 2014).
American Diabetes Association Annual Scientific Sessions, "New Diabetes Compound AVE0010 Showed Clear Dose Response Results With Once-A-Day Injection in Phase IIb Study", published Jun. 9 2008, two pages.
American Diabetes Association, "Standards of Medical Care in Diabetes." Diabetes Care 28(Supplement 1): S4-S36 (Jan. 2005).
American Diabetes Association, "Standards of Medical Care in Diabetes 2008." Diabetes Care 31(Supplement 1):S12-S54_.
Athauda et al., "Exenatide once weekly versus placebo in Parkinson's disease: a randomised, double-blind, placebo-controlled trial." Lancet S0140-6736(17)31585-4 (Aug. 2017).
Bastyr et al., "Therapy focused on lowering postprandial glucose, not fasting glucose, may be superior for lowering HbA1c. IOEZ Study Group." Diabetes Care 23(9):1236-41 (Sep. 2000).
Bell et al., "Sequence of the human insulin gene." 284(5751):26-32 (Mar. 1980).
Bennett, "Impact of the new WHO classification and diagnostic criteria." Diabetes Obes Metab 1(Supplement 2):S1-S6 (1999).
Bentley-Lewis et al., "Rationale, design, and baseline characteristics in Evaluation of LIXisenatide in Acute coronary Syndrome, a long-term cardiovascular end point trial of lixisenatide versus placebo" American Heart Journal, 169(5):631-38 (May 2015; Epub Feb. 11, 2015).
Buse et al., "Effects of exenatide (Exendin-4) on glycemic control over 30 weeks in sulfonylurea-treated patients with type 2 diabetes." Diabetes Care 27(11):2628-35 (Nov. 2004).
Byetta® Labeling Revision, pp. 1-24 (Jan. 11, 2008).
Byetta® European Public Assessment Report (EPAR), pp. 1-36 (Feb. 16, 2012).
Byetta® Prescribing Information, pp. 1-34 (Revised Oct. 2009).
Charbonnel et al., "Efficacy and safety of the dipeptidyl peptidase-4 inhibitor sitagliptin added to ongoing metformin therapy in patients with type 2 diabetes inadequately controlled with metformin alone." Diabetes Care 29(12):2638-43 (Dec. 2006).
Coutinho et al., "The relationship between glucose and incident cardiovascular events. A metaregression analysis of published data from 20 studies of 95,783 individuals followed for 12.4 years." Diabetes Care 22(2):233-40 (Feb. 1999).
Definition of "prevent" Dictionary.com; last accessed Sep. 29, 2016, pp. 1-6.
Definition of "induce" Dictionary.com; last accessed Sep. 29, 2016, pp. 1-6.
Degn et al., "Effect of Intravenous Infusion of Exenatide (Synthetic Exendin-4) on Glucose-Dependent Insulin Secretion and Counter-regulation During Hypoglycemia." Diabetes 53(9):2397-2403 (Sep. 2004).
de la Loge et al., "Cross-cultural development and validation of a patient self-administered questionnaire to assess duality of life in upper gastrointestinal disorders: The PAGI-QOL." Quality of Life Research 13(10):1751-62 (Dec. 2004).
Denker et al., "Exenatide (Exendin-4)-Induced Pancreatitis: A case report" Diabetes Care 29(2):471 (Feb. 2006).
De Venciana et al., "Postprandial versus preprandial blood glucose monitoring in women with gestational diabetes mellitus requiring insulin therapy." N Engl J Med 333(19):1237-41 (Nov. 1995).
Dombrowsky & Barrett, "Type II diabetes mellitus in children: Analysis of prevalence based on the pediatric heath information system (PHIS) database" American College of Clinical Pharmacology Annual Meeting, Bethesda, Maryland (Sep. 22nd-24th 2013).
Donahue et al., "Postchallenge glucose concentration and coronary heart disease in men of Japanese ancestry. Honolulu Heart Program." Diabetes 36(6):689-92 (Jun. 1987).
Eckert et al., "Assessing the progression of Parkinson's disease: A metabolic network approach," Lancet Neural. 6 (10):926-32 (Oct. 2007).
European Medicines Agency, "Guideline on clinical investigation of medicinal products in the treatment of hypertension" (EMA/238/1995 Rev 3) pp. 1-18 (Nov. 18, 2010).
European Diabetes Policy Group, "A desktop guide to Type 2 diabetes mellitus." Diabetic Medicine 16 (9):716-730 (1999).
Faichney, "Metformin in Type 1 diabetes: Is This a Good or Bad Idea?" Diabetes Care 26(5):1655 (May 2003).
Forlenza et al., "Diagnosis and biomarkers of predementia in Alzheimer's disease," BMC Medicine 8:89 pp. 1-14 (Dec. 2010).
Game "Novel hypoglycaemic agents: Considerations in patients with chronic kidney disease" Nephron Clin Pract. 126 (1):14-18 (Jan. 11, 2014).
Ganz et al., "The association of body mass index with the risk of type 2 diabetes: a case—control study nested in an electronic health records system in the United States." Diabetology & Metabolic Syndrome, 6:50, pp. 1-8 (Apr. 2014).
GenBank: AAP20099.1 "Interferon Alpha 2B [Homo sapiens]" dated Apr. 30, 2003; accessed Jan. 18, 2017, one page.
GenBank: AAA59149.1 "Interleukin 4 [Homo sapiens]" dated Jan. 6, 1995; accessed Jan. 18, 2017, one page.
GenBank: AAA52578.1 "GM-CSF [Homo sapiens]" dated Nov. 8, 1994; accessed Jan. 18, 2017, one page.
Gerich, "Insulin glargine: long-acting basal insulin analog for improved metabolic control." Curr Med Res Opin. 20 (1):31-37 (Jan. 2004).
Giacometti et al., "In vitro activity of the histatin derivative P-113 against multidrug-resistant pathogens responsible for pneumonia in immunocompromised patients." 49(3):1249-52 (Mar. 2005).
Giorda et al., "Pharmacokinetics, safety, and efficacy of Dpp-4 inhibitors and GLP-1 receptor agonists in patients with type 2 diabetes mellitus and renal or hepatic impairment. A systematic review of the literature." ENDOCRINE 46 (3):406-19 (Aug. 2014; epub Feb. 8, 2014).
Glucophage XR, Product Information, Bristol-Meyers Squibb Company (Jan. 2009).
Group et al., "Dose-dependent effects on glyburide on insulin secretion and glucose uptake in humans." Diabetes Care 14(8):724-27 (Aug. 1991).
Group, "Sulfonylureas in NIDDM." Diabetes Care 15(6):737-54 (Jun. 1992).

(56) References Cited

OTHER PUBLICATIONS

Halimi' "DPP-4 inhibitors and GLP-1 analogues: for whom? Which place for incretins in the management of type 2 diabetic patients?", Diabetes & Metabolism 34(Supplement 2):591-895 (Feb. 2008).
Hasslacher et al., "Diabetic kidney disease" Exp and Clin Endocrinol Diabetes 122(7):391-94 (Jul. 2014).
Heine & Dekker, "Beyond postprandial hyperglycemia: metabolic factors associated with cardiovascular disease." Diabetologia 45(4):461-75 (Apr. 2002).
Heine et al., "Exenatide versus insulin glargine in patients with suboptimally controlled type 2 diabetes." Ann Intern Med. 143(8):559-69 (Oct. 2005).
Hillier & Pedula, "Characteristics of an adult population with newly diagnosed Type 2 Diabetes. The relation of obesity and age of onset." Diabetes Care 24(9):1522-27 (Sep. 2001).
Hollander & Kushner, "Type 2 Diabetes Comorbidities and Treatment Challenges: Rationale for DPP4-Inhibitors" Postgraduate Medicine, 122(3):71-80 (May 2010).
Hubschle et al., "Anti-atherosclerotic activity of lixisenatide in ApoE knockout mice" Abstract 809, Diabetologia, 55 (Supplement 1):S334 (Oct. 2012).
Janka et al., "Comparison of basal insulin added to oral agents versus twice-daily premixed insulin as initial insulin herapy for type 2 diabetes." Diabetes Care 28(2):254-59 (Feb. 2005).
Williams & Pickup, "Macrovascular disease in Diabetes." In handbook of Diabetes. 2nd ed. Williams G, Pickup JC, Eds. Oxford, UK, Blackwell Science Chapter 21; pp. 151-58 (1999).
Wohlfart et al., "Cardioprotective effects of lixisenatide in rat myocardial ischemia-reperfusion injury studies" Journal of Translational Medicine, 11(1):84, 12 pages (Mar. 2013).
Wolever et al., "Second-meal effect: low-glycemic-index foods eaten at dinner improve subsequent breakfast glycemic response." Am J Clin Nutr 48(4):1041-47 (Oct. 1988).
Yki-Järvinen, "Combination Therapies with insulin in type 2 diabetes." Diabetes Care 24(4):758-67 (Apr. 2001).
Yki-Järvinen, "Comparison of Bedtime insulin regimes in patients with type 2 diabetes mellitus." Annals of Internal Medicine 130(5):389-96 (Mar. 1999).
Zeitler et al., "ISPAD Clinical Practice Consensus Guidelines 2014. Type 2 diabetes in the child and adolescent." Pediatr Diabets 15(Suppl 20)26-46 (Sep. 2014).
Zimmet et al., "The metabolic syndrome in children and adolescents." Lancet 369(9579)2059-61 (Jun. 2007).
Zinman et al., "The Effect of Adding Exenatide to a Thiazolidinedione in Suboptimally Controlled Type 2 Diabetes" Annals of Internal Medicine, 146(7):477-85 (Apr. 2007).
Final Office Action issued in U.S. Appl. No. 13/123,835; dated Nov. 18, 2015, pp. 1-16.
Non-Final Office Action issued in U.S. Appl. No. 15/340,969; dated Jul. 24, 2017, pp. 1-6.
Final Rejection issued in U.S. Appl. No. 13/382,442; dated Sep. 21, 2016, pp. 1-32.
Non-Final Office Action issued in U.S. Appl. No. 15/275,867; dated Jun. 1, 2017; pp. 1-11.
Non-Final Rejection issued in U.S. Appl. No. 13/509,507; dated Sep. 21, 2016, pp. 1-7.
Non-Final Rejection issued in U.S. Appl. No. 13/509,542; dated Nov. 13, 2016, pp. 1-34.
Non-Final Rejection issued in U.S. Appl. No. 14/172,151; dated Jan. 19, 2017, pp. 1-20.
Final Rejection issued in U.S. Appl. No. 14/172,151; dated Jan. 4, 2016, pp. 1-20.
Non-Final Rejection issued in U.S. Appl. No. 13/467,707; dated Nov. 7, 2016, pp. 1-17.
Non-Final Rejection issued in U.S. Appl. No. 15/197,378; dated Jun. 15, 2017, pp. 1-13.
Non-Final Rejection in U.S. Appl. No. 13/633,563; dated Oct. 5, 2016, pp. 1-12.
Final Rejection in U.S. Appl. No. 13/633,496; dated Oct. 13, 2016, pp. 1-10.
Non-Final Rejection in U.S. Appl. No. 13/633,496; dated May 25, 2017, pp. 1-10.
Non-Final Rejection issued in U.S. Appl. No. 14/303,895; dated Mar. 24, 2017, pp. 1-17.
Non-Final Rejection issued in U.S. Appl. No. 14/965,586; dated Mar. 22, 2017, pp. 1-17.
Non-Final Rejection issued in U.S. Appl. No. 15/068,286; dated Apr. 11, 2017, pp. 1-12.
International Search pp. 1-8. Report by the ISA for International Application No. PCT/EP2009/000018; dated Jun. 30, 2009,.
International Search pp. 1-4. Report by the ISA for International Application No. PCT/EP2016/050804; dated Mar. 4, 2016,.
International Search pp. 1-7. Report by the ISA for International Application No. PCT/EP2016/055267; dated May 20, 2016,.
International Search pp. 1-8. Report by the ISA for International Application No. PCT/EP2016/055267; dated Jun. 7, 2016,.
Partial International 2016, pp. 1-6. Search Report by the ISA for International Application No. PCT/EP2016/055954; dated Jun. 21, 2016, pp. 1-6.
International Search 2016, pp. 1-12. Report by the ISA for International Application No. PCT/EP2016/055954; dated Sep. 9, 2016, pp. 1-12.
Extended European Search Report for European Application No. 14 19 7685; dated Aug. 10, 2015, pp. 1-4.
Extended European Search Report for European Application No. 14 19 7685; dated Oct. 6, 2015, pp. 1-4.
Extended European Search Report for European Application No. 15 15 1488.2; dated Jul. 7, 2015, pp. 1-8.
Ahren, "GLP-1 for type 2 diabetes", Experimental Cell Research, 317(9):1239-45 (Jan. 2011).
American Diabetes Association, "Standards of Medical Care in Diabetes—2017" Diabetes Care 40(Supplement 1):S1- 3142 (Jan. 2017).
Berard et al., "Canadian Diabetes Association 2008 Clinical Practice Guidelines for the Prevention and Management of Diabetes in Canada." Canadian Journal of Diabetes 32(Supplement 1):1-215 (Sep. 2008).
Bergenstal et al., "Type 2 Diabetes: Assessing the Relative Risks and Benefits of Glucose-lowering Medications"The American Journal of Medicine 123(4):e9-e18 (Apr. 2010).
Bucceri et al., "Gallbladder and gastric emptying: relationship to cholecystokininemia in diabetics." Eur. J. Intern. Med. 13(2):123-28 (Mar. 2002).
Byetta® Summary of Product Characteristics, updated Jul. 22, 2016, last accessed Jul. 31, 2017, pp. 1-13.
Clinical Trials Archive for Trial No. NCT00763815 updated Feb. 21, 2014. Accessed at https://clinicaltrials.gov/archive/NCT00763815/2014_02_21/changes Accessed on Nov. 13, 2017. pp. 1-13.
Definition of "reduce" Dictionary.com; last accessed Aug. 13, 2017, pp. 1-4.
Godoy-Matos, "The role of glucagon on type 2 diabetes at a glance," Diabetology & Metabolic Syndrome 6:91, pp. 1-5 (Aug. 2014).
Home et al., "Management of type 2 diabetes: updated NICE guidance" BMJ 336: 1306-1308 (Jun. 2008).
Ismail-Beigi et al., "Individualizing Glycemic Targets in Type 2 Diabetes Mellitus: Implications of Recent Clinical Trials" Annals of Internal Medicine 154(8):554-559 (Apr. 2011).
Lawson et al., "Coordination of gastric and gallbladder emptying after ingestion of a regular meal." Gastroenterology. 85(4):866-70 (Oct. 1983).
Lee et al., "Goals of Glycemic Control in Frail Older Patients with Diabetes" JAMA 305(13):1350-51 (Apr. 2011).
Nathan et al., "Medical Management of Hyperglycemia in Type 2 Diabetes: a Consensus Algorithm for the Initiation and Adjustment of Therapy" Diabetologia 52:17-30 (2009: Epub Oct. 22, 2008).
NCT00715624 Clinical Trials.gov "GLP-1 Agonist AVE0010 in Patients With Type 2 Diabetes for Glycemic Control and Safety Evaluation, on Top of Basal Insulin" (updated Mar. 2, 2011), p. 1-3.
NCT00866658 ClinicalTrials.gov, "GLP-1 agonist AVE0010 in patients with type 2 diabetes for glycemic control and safety

(56) References Cited

OTHER PUBLICATIONS evaluation, on top of basal insulin +/− sulfonylurea" p. 1-3, accessed Mar. 16, 2016 (updated Aug. 3, 2010).
NICE, National Institute for Health and Care Excellence, "Type 2 diabetes in adults: management" pp. 1-45 (Dec. 2, 2015).
Rodbard et al., "Statement by an American Association of Clinical Endocrinologists/American College of Endocrinology Consensus Panel on Type 2 Diabetes Mellitus: An Algorithm for Glycemic Contra" Endocrine Practice 15(6):540-59 (Sep./Oct. 2009).
Sanofi-aventis Press Release, "Once Daily Lixisenatide in Combination with Basal Insulin Demonstrates Significant Improvement in Glucose Contra" Paris, France (Sep. 30, 2010) pp. 1-3.
Sutter Medical Foundation, "Type 2 Diabetes Adult Outpatient Insulin Guidelines" Feb. 2011, pp. 1-6.
Non-Final Rejection issued in U.S. Appl. No. 13/382,442; dated Sep. 20, 2017, pp. 1-28.
Non-Final Rejection issued in U.S. Appl. No. 15/073,364; dated Nov. 9, 2017, pp. 1-8.
Gillies et al, "Insulin Glargine" Drugs 59(2)L253-60 (Feb. 2000).
Sualandi-Signorini & Giorgi, "Insulin formulations—a review" European Review for Medical and Pharmacological Sciences 5:73-83 (2001).
Lantus® 100U/ml solution for injection (insulin glargine); published in vol. 24 No. 9 of Pract. Diab. Int. Nov./Dec. 2007, p. 472.
NCT01195454, NIH Clinical Trials, "Euglycemic clamp dose-response study comparing insulin glargine U300 with Lantus U100" last updated Sep. 3, 2010, pp. 1-3.
Profile of Lantus® (insulin glargine injection) 100 units/ml vs. NPH in patients with type 1 diabetes; https://www.lantus.com/hcp/aboutlantus/vs-nph, pp. 1-4, last accessed Feb. 19, 2016.
Rosenstock et al., "Reduced Hypoglycemia Risk with Insulin Glargine: A meta-analysis comparing insulin glargine with human Nph insulin in type 2 diabetes" Diabetes Care 28(4):950-55 (Apr. 2005).
Shi, "The Newest Handbook of Clinical Drugs" Military Medical Science Press, p. 809, (Jan. 2008). English translation submitted.
Tang, "Biotech Drugs—Introduction and Practice Handbook" Chemical Industry Press, pp. 635-36, (Jan. 2008). English translation submitted.
Wikipedia® entry for "Standard deviation" Retrieved on Oct. 10, 2017, pp. 1-3.
Non-Final Rejection issued is U.S. Appl. No. 15/595,929; dated Sep. 20, 2017, pp. 1-9.
Non-Final Rejection issued in U.S. Appl. No. 15/237,285; dated Sep. 29, 2017, pp. 1-10.
Non-Final Rejection issued in U.S. Appl. No. 15/144,270; dated Dec. 13, 2017, pp. 1-25.
Non-Final Rejection issued in U.S. Appl. No. 14/220,562; dated Apr. 8, 2015, pp. 1-18.
Non-Final Rejection issued in U.S. Appl. No. 14/624,575; dated Mar. 26, 2015, pp. 1-14.
Non-Final Rejection issued in U.S. Appl. No. 15/162,563; dated Feb. 8, 2017, pp. 1-13.
Final Rejection issued in U.S. Appl. No. 15/162,563; dated Dec. 18, 2017, pp. 1-16.
Final Rejection in U.S. Appl. No. 13/633,563; dated Apr. 28, 2017, pp. 1-12.
Non-Final Rejection issued in U.S. Appl. No. 14/995,910; dated Dec. 11, 2017, pp. 1-7.
Extended European Search Report for European Application No. 16 19 0103.8; dated Jun. 23, 2017, pp. 1-5.
Extended European Search Report for European Application No. 17 20 2727.8; dated Dec. 20, 2017, pp. 1-9.
Search Report in Chinese Patent Application No. 201410818149.0; dated Jan. 10, 2017, pp. 1-3. English ranslation submitted.
U.S. Appl. No. 15/411,557, dated Jan. 20, 2017, Boka et al.
U.S. Appl. No. 15/803,589, dated Nov. 3, 2017, Hagendorf et al.
U.S. Appl. No. 15/730,033, dated Oct. 11, 2017, Niemoller el al.

\* cited by examiner

SEQUENCE LISTING

```
<160> NUMBER OF SEQ ID NOS: 5

<210> SEQ ID NO 1
<211> LENGTH: 44
<212> TYPE: PRT
<213> ORGANISM: Artificial
<220> FEATURE:
<223> OTHER INFORMATION: desPro36-Exendin-4(1-39)-Lys6-NH2

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 2
<211> LENGTH: 39
<212> TYPE: PRT
<213> ORGANISM: Heloderma suspectum

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
```

```
<211> LENGTH: 30
<212> TYPE: PRT
<213> ORGANISM: artificial
<220> FEATURE:
<223> OTHER INFORMATION: GLP-1(7-36)

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 4
<211> LENGTH: 20
<212> TYPE: DNA
<213> ORGANISM: artificial
<220> FEATURE:
<223> OTHER INFORMATION: forward primer

<400> SEQUENCE: 4
gaattccgac atgactcagg                                             20

<210> SEQ ID NO 5
<211> LENGTH: 20
<212> TYPE: DNA
<213> ORGANISM: artificial
<220> FEATURE:
<223> OTHER INFORMATION: reverse primer

<400> SEQUENCE: 5
gttctgctgc atcttggaca                                             20
```

PHARMACEUTICAL COMPOSITION FOR USE IN THE TREATMENT OF A NEURODEGENERATIVE DISEASE

CROSS-REFERENCE TO RELATED APPLICATIONS

This application is a continuation of U.S. patent application Ser. No. 13/602,913 filed on Sep. 4, 2012, which claims priority from U.S. Provisional Application No. 61/530,146, filed Sep. 1, 2011 and European Patent Application No. 11179784.1, filed Sep. 1, 2011, the disclosures of which are incorporated herein by reference in their entirety.

Subject of the present invention is a pharmaceutical composition for use in the prevention or/and treatment of a neurodegenerative disease, the composition comprising desPro$^{36}$Exendin-4(1-39)-Lys$_6$-NH$_2$ or/and a pharmaceutically acceptable salt thereof, and optionally a pharmaceutically acceptable carrier, adjuvant, or/and auxiliary substance.

Alzheimer's Disease

Alzheimer's disease (AD) is a neurodegenerative disorder that results in the loss of cortical neurons, especially in the associative neocortex and hippocampus which in turn leads to slow and progressive loss of cognitive functions, ultimately leading to dementia and death. Major hallmarks of the disease are aggregation and deposition of misfolded proteins (Bertram et al 2010; Mancuso et al 2010): (1) aggregated beta-amyloid (Aβ) peptide as extracellular senile or neuritic 'plaques', and (2) hyperphosphorlylated tau protein as intracellular neurofibrillary 'tangles' (NFTs).

Genetically, AD is divided into two forms: (1) early-onset familial AD (<60 years), and (2) late-onset sporadic AD (>60 years). Rare, disease causing mutations in Amyloid precursor protein (APP), Presenilin 1 (PSEN1), and Presenilin 2 (PSEN2) genes are known to result in early-onset familial AD while, APOE (allele 4) is the single most important risk factor for late-onset AD (Bertram et al 2010).

Mitochondrial dysfunction and oxidative stress, demonstrated by protein oxidation and lipid peroxidation are characteristics of AD brain. An imbalance between production of reactive oxygen species (ROS) and breakdown of the chemically reactive species by antioxidants leads to oxidative stress. Aβ has direct oxidative effects but it can also disrupt mitochondrial redox activity resulting in an increase of free radicals. Neurons are less capable to defend against an increase in ROS as they have low levels of antioxidants relative to other mammalian cell types and thus are considered highly susceptible to oxidative stress. Addition of Aβ to primary neuronal cultures results in inhibition of ATPases, changes in cell potential, and Ca$^{2+}$ influx (Varadarajan et a 2000; Higginsa et at 2010).

There is no cure for this devastating disease at present and the few treatments approved by the US Food and Drug Administration (FDA) do not stop the progression of AD rather are only partially effective in improving the symptoms (Wollen 2010, Aderinwale et al 2010). Currently, licensed pharmaceutical therapies against AD are the acetylcholinesterase inhibitors such as Tacrine, Donepizil, Rivastigmine, Galantamine and the NMDA receptor antagonist memantine. The effect of these drugs is very limited, and the main action again is to reduce symptoms rather than prevent the development of the disease. Other drugs may be given 'off label', such as statins (cholesterol level reducing agents), antihypertensive drugs, anti-inflammatory drugs, or others. None of these drugs have been proven to reduce progression of AD (Kaduszkiewicz et al 2005; Hölscher, 2005). Other strategies for treating AD are under investigation. It has been found that Neuronal Growth Factor α (NGF) can decrease senile plaques and improve cognitive function (De Rosa et al 2005). Since insulin resistance is now known as one of the main problems in AD (Hölscher and Li, 2010), instead of insulin itself other growth factors such as the incretin hormone Glucagon-like peptide-1 (GLP-1) are showing good effects in pre-clinical studies. The GLP-1 incretin analogue liraglutide reduced the number of amyloid plaques, reduced beta-amyloid levels, prevented cognitive impairment and synaptic dysfunction, reduced the inflammation response and enhanced synapse growth and neurogenesis in the brains of a transgenic mouse model of AD (McClean et al 2011). The amyloid plaques and the associated inflammation response in the brain are key hallmarks of AD. Similar protective effects were found with another GLP-1 analogue receptor agonist in a transgenic mouse model of AD (Li et al 2010).

Parkinson's Disease

Parkinson's disease (PD) is a chronic neurodegenerative disorder of muscle movement commonly characterized by selective degeneration of nigrostriatal neurons, greatly reduced synthetic capacity for dopamine and a consequent failure to engage striatal dopamine receptors. (Gandhi et al 2005). Before the disease presents clinically, death of nigrostriatal neurons occurs in the substantia nigra pars compacta (SNc) silently, probably as a result of the occurrence of concurrent apoptotic, excitotoxic, free-radical mediated neuroinflammatory events. A therapeutic strategy offering cure for, or a means of arresting the pathology of PD remains elusive. Established drug therapies are essentially palliative and not effective in all patients. Since apoptotic cell death is one of the central components in selective nigrostriatal neuronal death (Schapira 2001) future therapeutic strategies could involve the targeted use of biomolecules with anti-apoptotic properties. Alternatively, a positive therapeutic effect could be produced by molecules with neurotrophic properties or the ability to stimulate neurogenesis of cells with a dopaminergic phenotype. It has recently be observed that the glucagon-like peptide-1 receptor (GLP-1) agonist exendin-4 shows neurotrophic (Perry et al 2002) and neuroprotective (Perry et al 2002) properties in cultures of PC12 cells subjected to excitotoxic stress. Recently, it was shown (Harkavyi et al 2008) that exendin-4 arrests progression of, or even reverse nigral lesions, once established in two PD mouse models. In addition, it has been shown that exendin-4 treatment protected dopaminergic neurons against degeneration, preserved dopamine levels, and improved motor function in the 1-methyl-4-phenyl-1,2,3,6-tetrahydropyridine (MPTP) mouse model of PD (Li et al 2009).

Huntington's Disease

Huntington's disease (HD) is an inherited neurodegenerative disorder typified by involuntary body movement, as well as psychiatric and cognitive abnormalities. The genetic defect underlying HD involves expansion of CAG trinucleotide repeats in exon 1 of the HD gene, resulting in polyglutamine expansion in the huntingtin (htt) protein. This leads to abnormal processing and deleterious intracellular aggregation. Recently it has been shown that exendin-4 treatment suppresses the development of mutant htt inclusions in the pancreas and brain ameliorates metabolic effects and motor dysfunction and extends survival of HD mice (Martin et al 2009).

Stroke

The pathophysiology of stroke includes death of cortical and striatal neurons via apoptosis (Mattson, 2007).

Recently it has been shown that administration of exendin-4 reduced brain damage and improved functional outcome in a transient middle cerebral artery occlusion stroke muse model (Li et al 2009). In a cerebral ischemia model in the gerbil, it was further shown that GLP-1 receptor stimulation with exendin-4 attenuated the ischemia-related neuronal death by interfering with microglial activation against transient cerebral ischemic damage. (Lee et al 2011). Teramoto et al (2011) showed that exendin-4 is effective in a cerebral ischemia-reperfusion injury mouse model. Exendin-4 treatment significantly reduced infarct volume and improved functional deficit.

Peripheral Sensory Neuropathy

About 60-70% of individuals with diabetes have some degree of neurological damage, specifically neuropathies that cause impaired sensation in the hands and/or feet, slowed gastric motility or carpal tunnel syndrome. There is currently no therapy proven to reverse the neurological damage caused by prolonged hyperglycaemia and the associated metabolic disturbances. GLP-1 expression has been identified in neurons in the nodose ganglion, suggesting a role of GLP-1 in peripheral neurotransmission (Nakagawa 2004). In a rodent model of pyridoxine-induced peripheral neuropathy in non-diabetic rodents, GLP-1 and s.c. exendin-4 were shown to partially protect against several pyridoxine-induced functional and morphological defects and to facilitate normalization of axonal size (Perry et al 2007).

Cognitive Function, Mood and Memory:

GLP-1 receptor agonists are able to enhance cognitive function in rodents, as measured in the Morris water maze; the GLP-1 receptor knock-out mouse has a phenotype characterized by a learning deficiency that is restored after hippocampal GLP-1 receptor gene transfer (During et al 2003). Recently, Isacson et al (2010) showed an effect of chronic exendin-4 treatment on hippocampus-associated cognitive and mood-related behaviour in adult rodents. In another study, the polyneuropathy found in the dorsal root ganglion of a mouse model of diabetes was reversed by exendin-4 (Himeno et al 2011). Another GLP-1 analogue, liraglutide has been shown to exert beneficial effects on cognitive function and hippocampal synaptic plasticity in mice with high fat dietary-induced obesity and insulin resistance (Porter et al 2010).

Glucagon-Like Peptide 1

Glucagon-like peptide 1, GLP-1 or GLP-1(7-36) is a 30-amino acid peptide hormone that is encoded in the proglucagon gene. It is mainly produced in enteroendocrine L cells of the gut and is secreted into the blood stream when food containing fat, protein hydrolysate, and/or glucose enters the duodenum. The most widely studied cell activated by GLP-1 is the insulin-secreting beta cell in the pancreas where its defining action is augmentation of glucose-induced insulin secretion. Upon GLP-1 receptor (GLP-1R) activation in the beta cells, adenylyl cyclase (AC) is activated and cAMP is generated, leading, in turn, to cAMP-dependent activation of second messenger pathways, such as the protein kinase A (PKA) and Epac pathways. As well as short-term effects of enhancing glucose-induced insulin secretion, continuous GLP-1R activation also increases insulin synthesis, beta cell proliferation and neogenesis (Doyle et a 2007). Furthermore, GLP-1 generally regulates the concentrations of glucagons, slows down gastric emptying, stimulates the biosynthesis of (Pro-)insulin, increases the sensitivity toward insulin, and stimulates the insulin-independent biosynthesis of glycogen (Hoist (1999); Curr. Med. Chem 6: 1005; Nauck et al (1997) Exp Clin Endocrinol Diabetes 105:187; Lopez-Delgado et al (1998) Endocrinology 139: 2811).

The particular effects of GLP-1 on insulin and glucagon secretion have generated a research activity over the past 20 years culminating in a naturally occurring GLP-1 receptor (GLP-1R) agonist, exendin 4, now being used to treat type 2 diabetes mellitus (T2DM) (Doyle at al 2007).

In tissues other than the pancreas (brain, kidney, lung, heart, and major blood vessels) GLP-1 can activate a specific guanine nucleotide-binding protein (G-protein) coupled receptor.

GLP-1 has shown growth factor-like as well as neuroprotective properties (McClean et al 2010). GLP-1 also reduces the induction of apoptosis of hippocampal neurons and improves spatial and associative learning (During et al 2003). Perry et al (2002) reported that GLP-1 could completely protect cultured rat hippocampal neurons against glutamate-induced apoptosis. The GLP-1 analogues (Val8) GLP-1 and N-acetyl-GLP-1 have shown prominent effects on long term potentiation of synaptic transmission (LTP) in the hippocampus (McClean et at 2010). The GLP-1 analogue liraglutide reduced the number of amyloid plaques, reduced beta-amyloid levels, prevented cognitive impairment and LTP depression, reduced the inflammation response and enhanced synapse growth and neurogenesis in the hippocampus of a transgenic mouse model of AD (McClean et a 2011).

GLP-1, liraglutide and exendin-4 have been shown to cross the blood brain barrier (BBB) (Kastin et al 2001; McClean et al 2011). Perry et al (2003) found that GLP-1 and exendin-4 reduced the levels of beta amyloid in the brain and amyloid precursor protein in neurons. Chronic treatment with exendin-4 or liraglutide affects cell proliferation and neuroblast differentiation in the adult mouse hippocampal dentate gyrus (Li et al 2010; Hamilton et al 2011).

Liraglutide is a GLP-1 analogue having the formula Arg$^{34}$,Lys$^{26}$(N$^{\varepsilon}$(γ-glutamyl(N$^{\alpha}$-hexadecanoyl)))GLP-1(7-37). Liraglutide is usually administered parenterally.

The compound desPro$^{36}$Exendin-4(1-39)-Lys$_6$-NH$_2$ (AVE0010, lixisenatide) is an analogue of exendin-4. Lixisenatide is disclosed as SEQ ID NO:93 in WO 01/04156:

SEQ ID NO: 1: Lixisenatide (44 AS)
H-G-E-G-T-F-T-S-D-L-S-K-Q-M-E-E-E-A-V-R-L-F-I-E-W-

L-K-N-G-G-P-S-S-G-A-P-P-S-K-K-K-K-K-K-NH$_2$

SEQ ID NO: 2: Exendin-4 (39 AS)
H-G-E-G-T-F-T-S-D-L-S-K-Q-M-E-E-E-A-V-R-L-F-I-E-W-

L-K-N-G-G-P-S-S-G-A-P-P-P-S-NH$_2$

SEQ ID NO: 3: GLP-1(7-36)(30 AS)
H-A-E-G-T-F-T-S-D-V-S-S-Y-L-E-G-Q-A-A-K-E-F-I-A-W-

L-V-K-G-R

Exendins are a group of peptides which can lower blood glucose concentration. Exendins have an amino acid sequence identity of only about 50% with GLP-1 (7-36). Therefore, exendins are generally not regarded as GLP-1 analogs.

Lixisenatide is characterised by C-terminal truncation of the native exendin-4 sequence. Lixisenatide comprises six C-terminal lysine residues not present in exendin-4. Up to now, lixisenatide has not been considered as a drug suitable for the treatment of CNS disorders, in particular neurodegenerative diseases, as the C-terminal lysine residues may prevent the drug to pass the blood-brain-barrier. At present, there is no indication that lixisenatide could be transported across the blood-brain-barrier by a specific or/and regulated mechanism.

In example 1 of the present invention, is has been demonstrated that lixisenatide has superior properties compared to the GLP-1 analogue liraglutide and to exendin-4, both of which are currently used as treatments for type 2 diabetes:

(a) Surprisingly, lixisenatide can cross the blood brain barrier. The data of the present invention indicate that the transport is regulated, as the transport rate at high concentrations is limited to a maximum level. Furthermore, lixisenatide is taken up into the brain at a lower parenteral dose as compared with liraglutide.

(b) Lixisenatide activates GLP-1 receptors in the brain and induces cAMP production. Surprisingly, lixisenatide produces higher levels of cAMP than liraglutide, demonstrating higher effectiveness at activating the GLP-1 receptor at the same dose.

(c) Lixisenatide can induce proliferation of progenitor cells in the dentate gyrus. Compared with exendin-4 or with liraglutide, lixisenatide provides enhanced effects when administered at the same dose. In neurodegenerative diseases, these effects can constitute a disease-modifying effect.

(d) Lixisenatide showed superior neuroprotective effects (against cellular stress) in the dentate gyrus when compared with liraglutide.

(e) surprisingly, a pre-treatment with a dose of 10 nM lixisenatide was sufficient in protecting SH-SY5Y neuroblastoma cells from 1200 µM Methyl Glyoxal stress. A dose of 200 nM liraglutide was necessary in protecting cells from 1200 µM Methyl Glyoxal stress, indicating that a lower dose of lixisenatide is sufficient to induce protection (see also data of Example 2 obtained by pretreatment with GLP-1 agonists).

Example 2 demonstrates that a post-treatment with lixisenatide was sufficient in protecting SH-SY5Y neuroblastoma cells from 2 mM Methyl Glyoxal stress or 1 mM $H_2O_2$ stress. In contrast, Liraglutide did not protect cells from the stress by MG or $H_2O_2$.

In Example 3, Lixisenatide exhibited significant neuroprotective effects in rotenone treated LUHMES cells against neurodegeneration. Lixisenatide provides advantages compared with other GLP-1 receptor (GLP-1R) agonists. In rotenone treated LUHMES cells, Lixisenatide is significantly active at 3-fold lower concentrations than Liraglutide, a result comforting the unexpected superior activity effect seen in the Methyl Glyoxal model of Example 1. Exenatide did not elicit a significant effect at concentrations of 0.3 and 1 µM. In contrast, Lixisenatide provides a dose-dependent improvement of viability at these concentrations.

In Example 4, it is demonstrated that lixisenatide treatment in vivo leads to a decrease of amyloid plaque load in the brain of transgenic mice, models of Alzheimer's disease. Therefore, in addition to its neuroprotective properties, lixisenatide can decrease cerebral pathological lesions such as amyloid plaques and represents therefore an attractive prevention or/and treatment for Alzheimer's Disease. Activity is observed at lower dose (10 nmol/kg) than previously described for liraglutide (25 nmolm/kg) by McLean et al (2011).

Therefore, lixisenatide is suitable for the treatment or/and prevention of a neurodegenerative disease, as described herein, for example Alzheimer's disease, Parkinson's disease or/and stroke.

A first aspect of the present invention is a pharmaceutical composition for use in the prevention or/and treatment of a neurodegenerative disease, the composition comprising desPro$_{36}$Exendin-4(1-39)-Lys$_6$-NH$_2$ or/and a pharmaceutically acceptable salt thereof, and optionally a pharmaceutically acceptable carrier, adjuvant, or/and auxiliary substance.

Another aspect of the present invention is a pharmaceutical composition for use in the treatment of a neurodegenerative disease, the composition comprising desPro$^{36}$Exendin-4(1-39)-Lys$_6$-NH$_2$ or/and a pharmaceutically acceptable salt thereof, and optionally a pharmaceutically acceptable carrier, adjuvant, or/and auxiliary substance.

The neurodegenerative disease may be any neurodegenerative disease, in particular a neurodegenerative disease which is associated with oxidative stress, loss of neurite integrity, apoptosis, neuronal loss or/and inflammation response.

In the present invention, loss of neurite integrity includes dendritic spine loss, loss of synaptic plasticity, or/and loss of new compensatory neurite sprouting.

The neurodegenerative disease may be associated with cognitive impairment.

In particular, the neurodegenerative disease is selected from the group consisting of Alzheimer's disease, Parkinson's disease, progressive supranuclear palsy (PSP), multiple system atrophy (MSA), Lewy body dementia, Parkinson's disease dementia, epilepsy, stroke, Huntington's Chorea, cerebral hypoxia, multiple sclerosis, and peripheral neuropathy. The peripheral neuropathy may be associated with diabetes mellitus.

It is preferred that the neurodegenerative disease is selected from the group consisting of Alzheimer's disease, Parkinson's disease, and stroke.

It is also preferred that the neurodegenerative disease is selected from the group consisting of progressive supranuclear palsy, multiple system atrophy, Lewy body dementia, Parkinson's disease, and Parkinson's disease dementia. Any one of these diseases may be associated with Parkinsonism.

Progressive supranuclear palsy and multiple system atrophy are collectively known as Parkinson-plus syndromes.

In the present invention, Parkinsonism is a neurological syndrome which is characterised by a combination of specific symptoms such as tremor, hypokinesia, rigidity, or/and postural instability.

In one embodiment, the neurodegenerative disease is Alzheimer's disease. Alzheimer's disease can be associated with oxidative stress and neuronal loss.

In another embodiment, the neurodegenerative disease is Parkinson's disease. Parkinson's disease may be associated with oxidative stress, inflammatory response, apoptosis, neuronal loss, in particular loss of dopaminergic neurons, for example neuronal loss in the substantia nigra resulting in a lack of dopamine.

Neuronal loss may be caused by apoptosis.

In another embodiment, the neurodegenerative disease is progressive supranuclear palsy. Progressive supranuclear palsy may be associated with neuronal loss, in particular loss of dopaminergic neurons.

In another embodiment, the neurodegenerative disease is multiple system atrophy. Multiple system atrophy may be associated neuronal loss, in particular loss of dopaminergic neurons.

In another embodiment, the neurodegenerative disease is Lewy body dementia. Lewy body dementia may be associated with neuronal loss, in particular loss of dopaminergic neurons. Lewy body dementia may be associated with Parkinson's disease.

In another embodiment, the neurodegenerative disease is Parkinson's disease dementia. Parkinson's disease dementia may be associated neuronal loss, in particular loss of dopaminergic neurons. In particular, Parkinson's disease dementia is associated with Parkinson's disease.

In yet another embodiment, the neurodegenerative disease is stroke. Stroke may be associated with neuronal loss caused by ischemia, wherein ischemia may be caused by blockage (such as thrombosis or arterial embolism) or haemorrhage.

In yet another embodiment, the neurodegenerative disease is multiple sclerosis, which may be associated with inflammatory processes in the CNS.

The data of the present invention demonstrate that (a) lixisenatide provides neuroprotective or/and neurogenerative effects, and (b) lixisenatide is superior compared with other GLP-1 agonists, such as exendin-4 or liraglutide. Thus lixisenatide can provide a disease-modifying effect in neurodegenerative diseases, such as Alzheimer's disease, Parkinson's disease, and stroke. In particular, administration of lixisenatide is suitable for the treatment in an early stage of a neurodegenerative disease, as neuroprotection and neurogeneration could slow down the progression of the disease and thereby improve quality of life.

Therefore, in one aspect of the present invention, the neurodegenerative disease is in an early stage. For example, the Alzheimer's disease may be an early-stage Alzheimer's disease. Early-stage Alzheimer's disease (AD) is also termed prodromal Alzheimer's disease or predementia Alzheimer's disease. (Dubois et al. 2010). Early stage Alzheimer's disease can be defined as: patients presenting objective memory complaint associated with supportive biomarker data or Alzheimer's disease pathology: in cerebrospinal fluid (CSF) low levels of β-amyloid 42 (Ab42) peptide over Tau protein ratio are found, or amylold plaque in the brain are detected by amyoid PET (positron emission tomography) agent such as AmyVid™ from E. Lilly (Avid).

In another example, the Parkinson's disease may be an early-stage Parkinson's disease. In yet another example, the progressive supranuclear palsy may be an early-stage progressive supranuclear palsy. In yet another example, the multiple system atrophy may be an early-stage multiple system atrophy. In another example, the Lewy body dementia may be an early-stage Lewy body dementia. In a further example, the Parkinson's disease dementia may be an early-stage Parkinson's disease dementia.

Furthermore, lixisenatide is suitable in the prevention of a neurodegenerative disease, in particular in those patients suspected of suffering from a neurodegenerative disease without having a clear diagnosis. In another aspect of the present invention, the pharmaceutical composition, as described herein, is for use in the prevention of a neurodegenerative disease.

In the context of the present invention, desPro$^{36}$Exendin-4(1-39)-Lys$_6$-NH$_2$ (lixisenatide) includes pharmaceutically acceptable salts thereof. The person skilled in the art knows pharmaceutically acceptable salts of lixisenatide. A preferred pharmaceutically acceptable salt of lixisenatide employed in the present invention is acetate.

In the present invention, desPro$^{36}$Exendin-4(1-39)-Lys$_6$-NH$_2$ or/and the pharmaceutically acceptable salt thereof may be administered to a patient in need thereof, in an amount sufficient to induce a therapeutic effect.

In the present invention, desPro$^{36}$Exendin-4(1-39)-Lys$_6$-NH$_2$ or/and the pharmaceutically acceptable salt thereof may be formulated with suitable pharmaceutically acceptable carriers, adjuvants, or/and auxiliary substances.

The pharmaceutical composition of the present invention provides a disease-modifying effect by its neuroprotective and neuroregenerative effects, as described herein, in a neurodegenerative disease, as described herein. In particular, a disease-modifying response can be obtained in the treatment of a neurodegenerative disease as described herein, for example in Alzheimer's disease, Parkinson's disease, progressive supranuclear palsy, multiple system atrophy, Lewy body dementia, Parkinson's disease dementia, epilepsy, stroke, Huntington's Chorea, cerebral hypoxia, multiple sclerosis, and peripheral neuropathy as described herein.

The pharmaceutical composition of the present invention may be administered parenterally, e.g. by injection (such as by intramuscular or by subcutaneous injection). Suitable injection devices, for instance the so-called "pens" comprising a cartridge comprising the active ingredient, and an injection needle, are known. The compound desPro$^{36}$Exendin-4(1-39)-Lys$_6$-NH$_2$ or/and a pharmaceutically acceptable salt thereof may be administered in a suitable amount, for instance in an amount in the range of 1 to 50 μg per dose, 5 to 40 μg per dose, 10 to 30 μg per dose, 10 to 15 μg per dose or 15 to 20 μg per dose.

In the present invention, the compound desPro$^{36}$Exendin-4(1-39)-Lys$_6$-NH$_2$ or/and a pharmaceutically acceptable salt thereof may be administered in a daily dose in the range of 1 to 50 μg, in the range of 5 to 40 μg, in the range of 10 to 30 μg, in the range of 10 to 20 μg, in the range of 10 to 15 μg, or in the range of 15 to 20 μg. The composition of the present invention may be administered by one injection per day.

In the present invention, the composition of the present invention may be provided as a liquid composition. The skilled person knows liquid compositions of lixisenatide suitable for parenteral administration. A liquid composition of the present invention may have an acidic or a physiologic pH. An acidic pH preferably is in the range of pH 1-6.8, pH 3.5-6.8, or pH 3.5-5. A physiologic pH preferably is in the range of pH 2.5-8.5, pH 4.0-8.5, or pH 6.0-8.5. The pH may be adjusted by a pharmaceutically acceptable diluted acid (typically HCl) or pharmaceutically acceptable diluted base (typically NaOH).

The liquid composition of the present invention may comprise a suitable preservative. A suitable preservative may be selected from phenol, m-cresol, benzyl alcohol and p-hydroxybenzoic acid ester. A preferred preservative is m-cresol.

The liquid composition of the present invention may comprise a tonicity agent. A suitable tonicity agent may be selected from glycerol, lactose, sorbitol, mannitol, glucose, NaCl, calcium or magnesium containing compounds such as CaCl$_2$. The concentration of glycerol, lactose, sorbitol, mannitol and glucose may be in the range of 100-250 mM. The concentration of NaCl may be up to 150 mM. A preferred tonicity agent is glycerol.

The liquid composition of the present invention may comprise methionine from 0.5 μg/mL to 20 μg/mL, preferably from 1 μg/ml to 5 μg/ml. Preferably, the liquid composition comprises L-methionine.

Yet another aspect of the present invention refers to a method for the prevention or/and treatment of a medical indication, as described herein. For example, the method may comprise the administration of the pharmaceutical composition as described herein. The method may be a method for the prevention or/and treatment of a neurodegenerative disease, as described herein.

In particular, the method, as described herein, elicits a disease-modifying response, for example by neuroprotection or/and neurogeneration.

In the method of the present invention, a disease-modifying therapy by its neuroprotective and neuroregenerative effects is provided by administration of the pharmaceutical composition, as described herein, in a neurodegenerative disease, as described herein. In particular, a disease-modifying response can be obtained in the treatment of a neurodegenerative disease as described herein, for example in Alzheimer's disease, Parkinson's disease, progressive supranuclear palsy, multiple system atrophy, Lewy body dementia, Parkinson's disease dementia, epilepsy, stroke, Huntington's Chorea, cerebral hypoxia, multiple sclerosis, and peripheral neuropathy, as described herein.

In the method of the present invention, a therapeutically effective amount of the pharmaceutical composition, as described herein, is administered.

Yet another aspect of the present invention refers to the use of the composition as described herein for the manufacture of a medicament for the treatment of a medical indication, as described herein. For example, the composition of the present invention can be used for the manufacture of a medicament for the prevention or/and treatment of a neurodegenerative disease, as described herein.

The invention is further illustrated by the following examples and figures.

EXAMPLE 1

Lixisenatide is a peptide drug whict1 typically is administered parenterally. To elicit an activity against neurodegenerative diseases, such as Alzheimer's disease, Parkinson's disease, progressive supranuclear palsy, multiple system atrophy, Lewy body dementia, Parkinson's disease dementia or stroke, lixisenatide must cross the blood-brain-barrier. Lixisenatide, in particular when administered parenterally, is suitable for the treatment or/and prevention of neurodegenerative diseases if lixisenatide provides one or more of the following features:
(a) lixisenatide can cross the blood brain barrier,
(b) lixisenatide activates GLP-1 receptors in the brain and induces physiological effects by receptor activation,
(c) lixisenatide provides disease-modifying effects in suitable models,
(d) lixisenatide is neuroprotective in suitable models, and
(e) lixisenatide provides advantages over other GLP-1 receptor agonists, such as liraglutide or exenatide.

Lixisenatide Uptake by the Brain

Figure 1A:
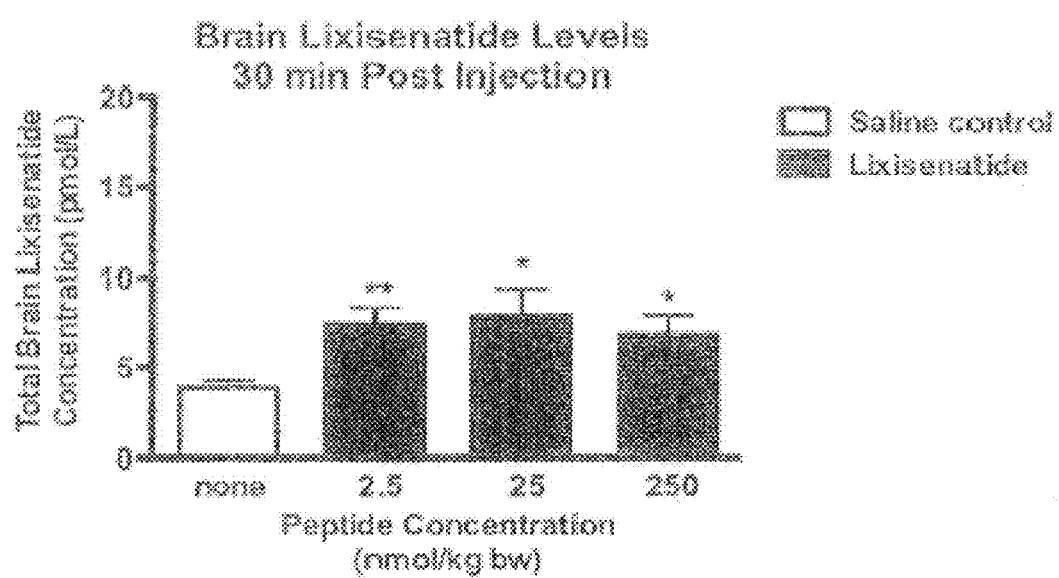
FIG. 1A shows total lixisenatide concentration (pmol/L) measured in the brains of wild type female mice (n=5, average age 24 weeks) at 30 min following i.p. saline vehicle (0.9% w.v NaCl) or i.p. lixisenatide (2.5, 25 or 250 nmol/kg body weight) injection. Values are the mean±S.E.M. *$p<0.05$, **$p<0.01$.
Figure 1B:
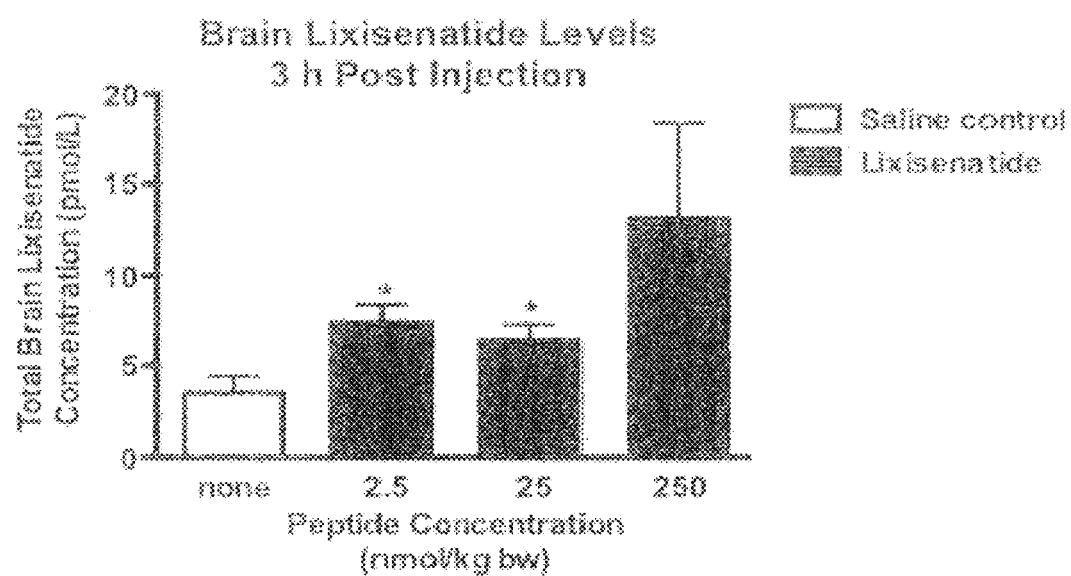
FIG. 1B shows total lixisenatide concentration (pmol/L) measured in the brains of wild type female mice (n=5, average age 24 weeks) at 3 h following i.p. saline vehicle (0.9% w.v NaCl) or i.p. lixisenatide (2.5, 25 or 250 nmol/kg body weight) injection. Values are the mean±S.E.M. *$p<0.05$.

In the present Example, it is described whether the GLP-1 receptor agonist lixisenatide crossed the blood-brain-barrier (BBB). 3 doses (2.5 nmol/kg bw, 25 nmol/kg bw and 250 nmol/kg bw, ip.) were tested, and the levels found in mouse brain tissue 30 min and 3 h post injection were examined. Lixisenatide levels were enhanced 30 min after delivery with all doses and were also detected with both the low (2.5 nmol/kg bw) and medium level (25 nmol/kg bw), but not the high dose of 250 nmol/kg bw of lixisenatide. This difference suggests that transport of lixisenatide into the brain is regulated, limiting the influx of high concentrations of lixisenatide tested here (FIG. 1).

Comparison of Lixisenatide Uptake with Liraglutide Uptake in the Brain

Figure 2A:
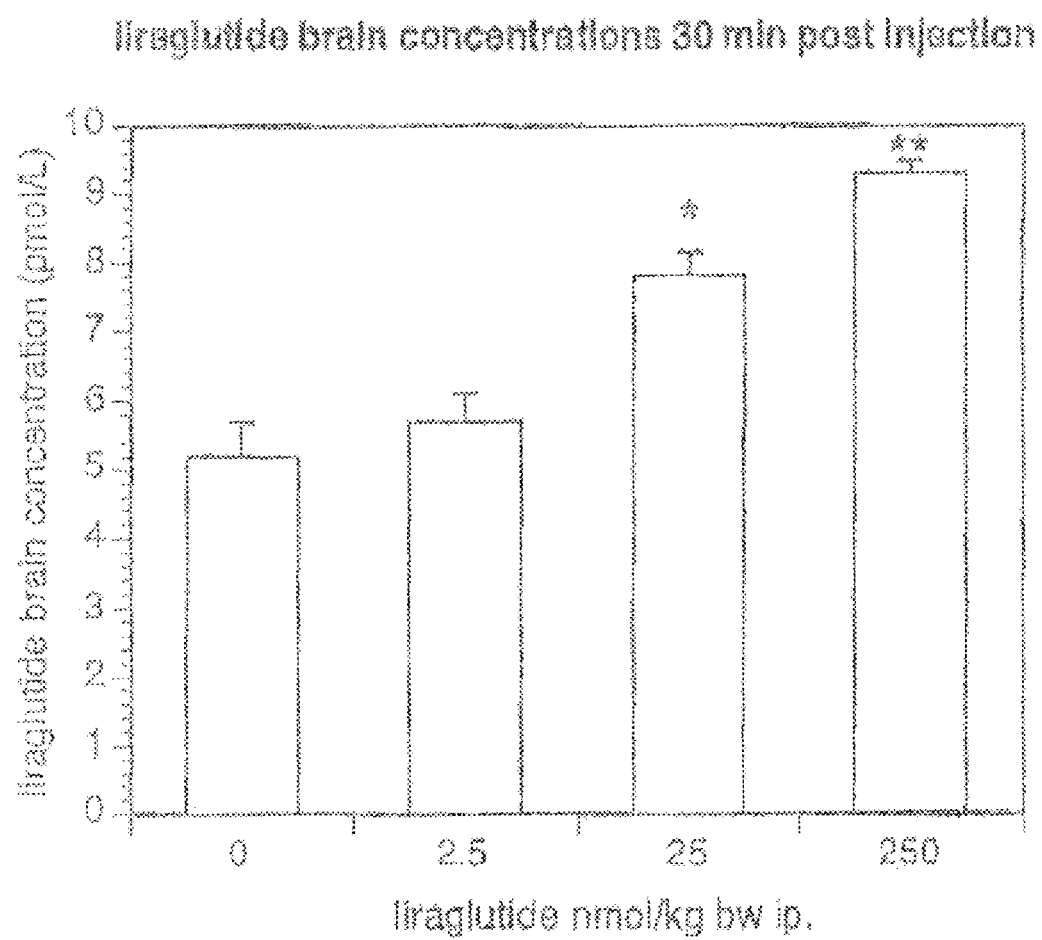
FIG. 2A shows total liraglutide concentration (pmol/L) measured in the brains of wild type female mice (n=5) at 30 min following i.p. saline vehicle (0.9% w.v NaCl) or i.p. liraglutide (2.5, 25 or 250 nmol/kg body weight) injection. Values are the mean±S.E.M. *$p<0.05$, **$p<0.01$.
Figure 2B:
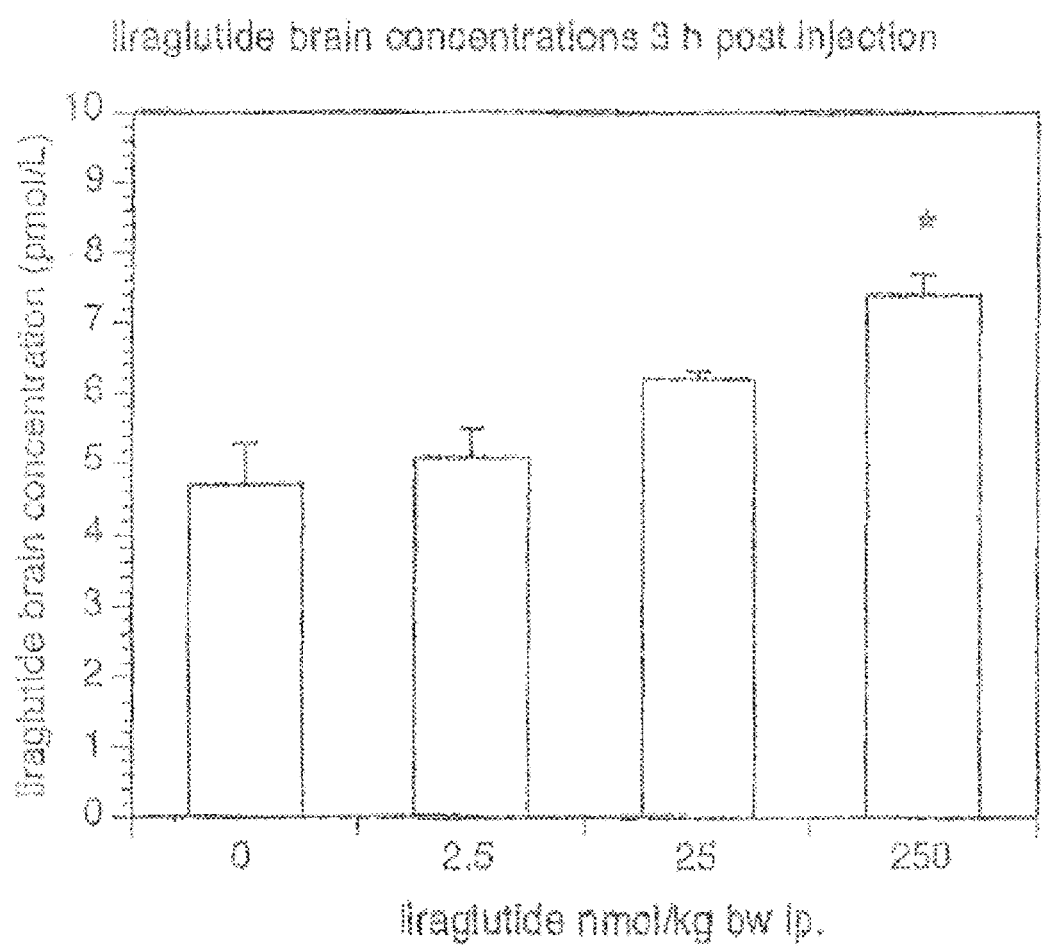
FIG. 2B shows total liraglutide concentration (pmol/L) measured in the brains of wild type female mice at 3 h following i.p. saline vehicle (0.9% w.v NaCl) or i.p. liraglutide (2.5, 25 or 250 nmol/kg body weight) injection. Values are the mean±S.E.M. *$p<0.05$.

The above results for lixisenatide were compared to those for the GLP-1 agonist, liraglutide (Victoza by Novo Nordisk). As discussed above and shown in FIGS. 1 and 2, lixisenatide levels showed significant increase in the brain at the lowest dose of 2.5 nmol/kg bw ip., whereas liraglutide did not show an increase at this dose (FIG. 2), suggesting that lixisenatide is taken up into the brain at lower concentrations than liraglutide.

From this finding it is concluded that lixisenatide requires a lower dose of lixisenatide to pass the blood-brain-barrier, compared with liraglutide, so that it can exert a therapeutic effect upon neurodegenerative diseases, as described herein, at a lower dose, compared with liraglutide.

GLP-1 Receptor Activation in the Brain/Production of cAMP

Preliminary studies have shown that lixisenatide activates the pancreas GLP-1 receptor that is linked to the enhancement of the cAMP levels (for review, see, for example, Doyle et al., 2007)

Figure 3A:
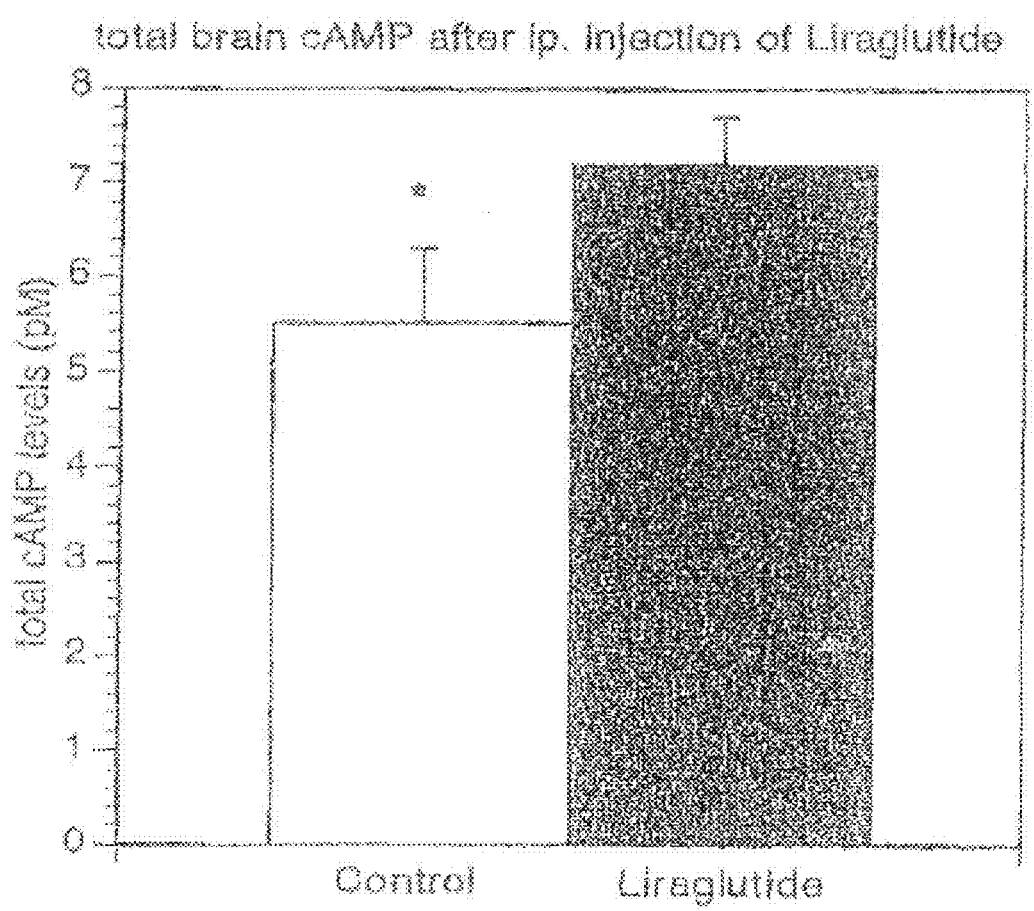
FIG. 3A shows injection of 25 nmol/kg bw liraglutide ip. 30 min before analysis showed a significant increase of cAMP in the brain compared to controls ($p<0.05$; t-test).
Figure 3B:
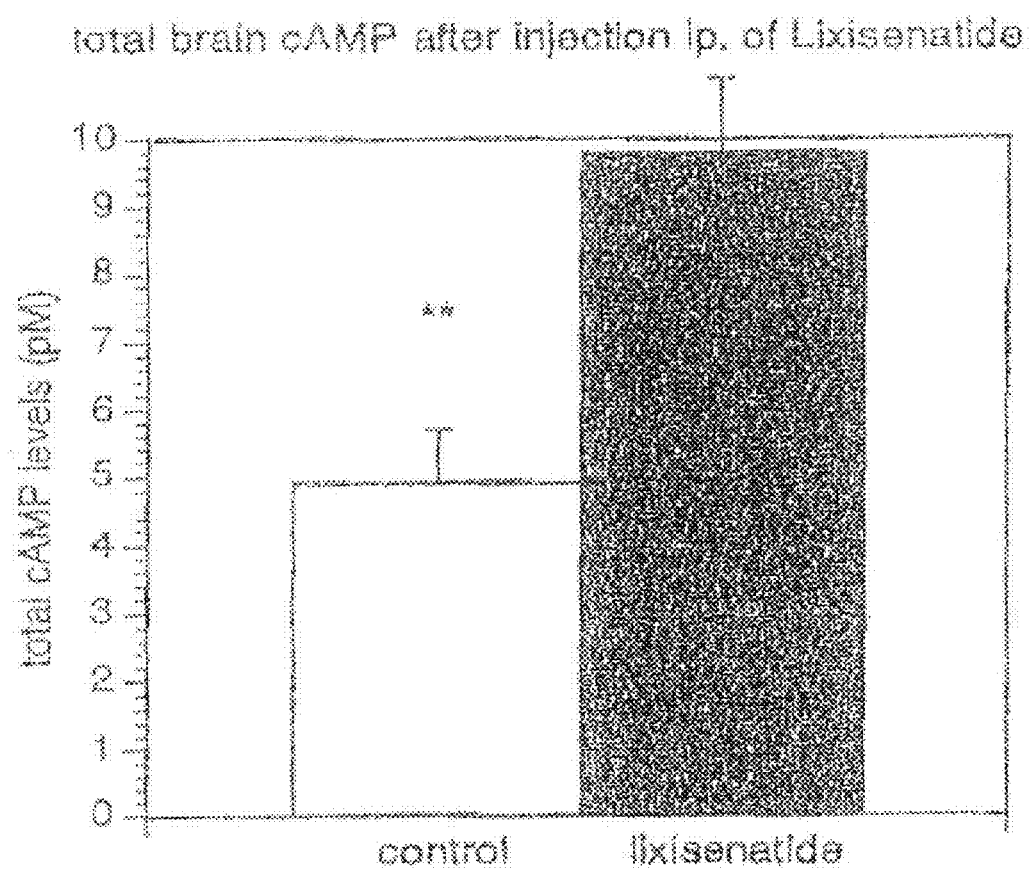
FIG. 3B shows injection of 25 nmol/kg bw lixisenatide ip, 30 min before analysis showed a significant increase of cAMP in the brain compared to controls ($p<0.01$; t-test).
Figure 3C:
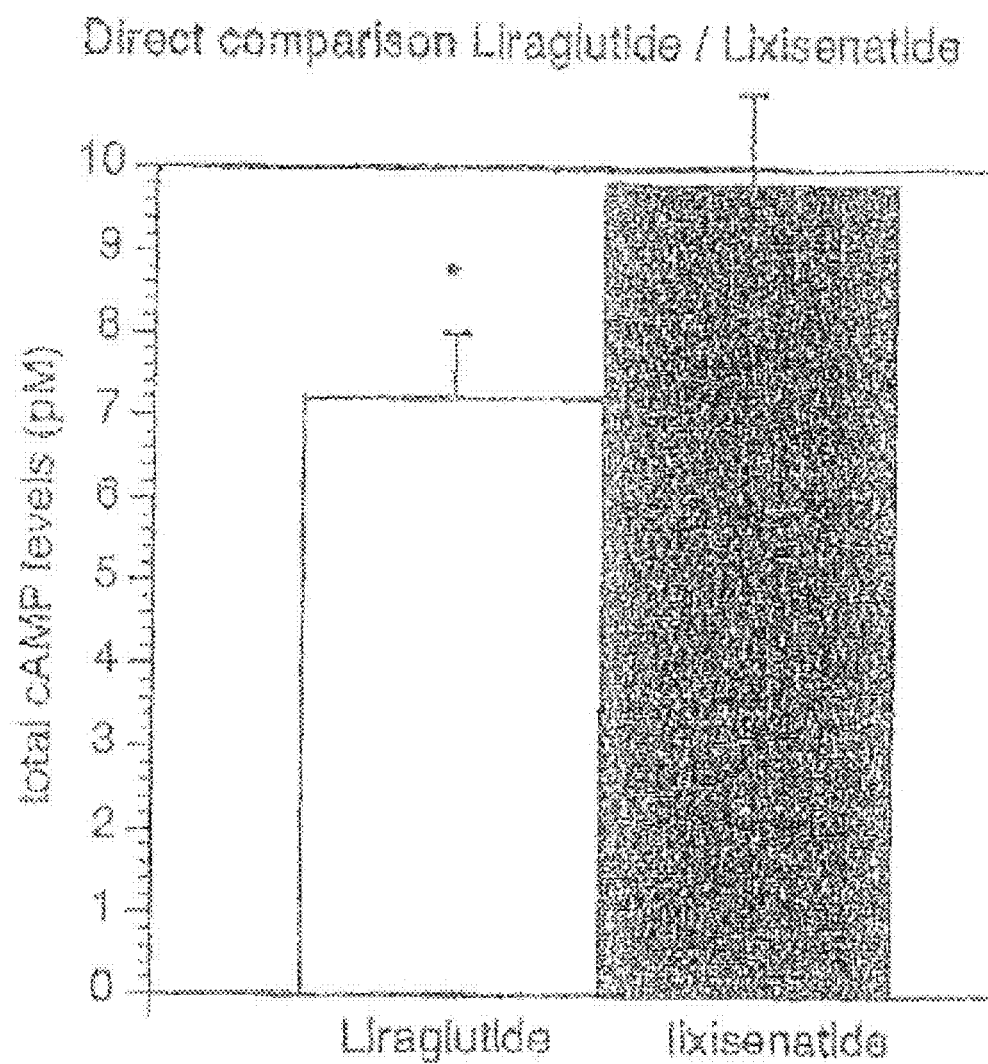
FIG. 3C shows when directly comparing the effects of liraglutide with lixisenatide, a significant difference between drugs is found ($p<0.05$; t-test).

In the present example, it has been shown for the first time that injecting lixisenatide i.p. increased the amount of cAMP in the brain, indicating that the lixisenatide activates GLP-1 receptors in the brain (FIG. 3b). A direct comparison of the effects of lixisenatide (25 nmol/kg bw i.p.) and liraglutide (25 nmol/kg bw i.p., for results, see FIG. 3a) on GLP-1 receptor is shown in FIG. 3c. Lixisenatide produces significantly higher levels of cAMP than liraglutide (*=p<0.05) at the same dose, demonstrating a higher effectiveness of lixisenatide.

Neurogenerative Effects/Disease-Modifying Effects of Lixisenatide in the Brain

Figure 4:
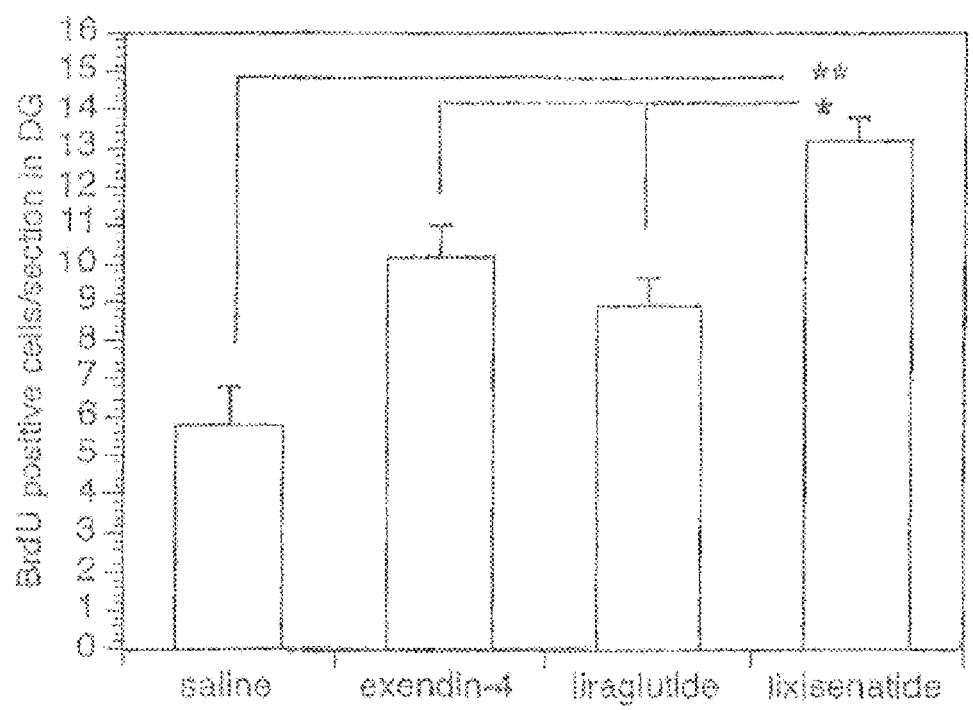
FIG. 4 shows the effect of once-daily injection of either exendin-4, liraglutide or lixisenatide 25 nmol/kg bw, for 3 weeks on cell proliferation in the dentate gyrus (BrdU staining). Values are the mean±S.E.M. *$p<0.05$, **$p<0.01$. Lixisenatide shows an increased cell proliferative activity compared to exendin-4 and liraglutide ($p<0.05$) and controls ($p<0.01$).
Figure 5:
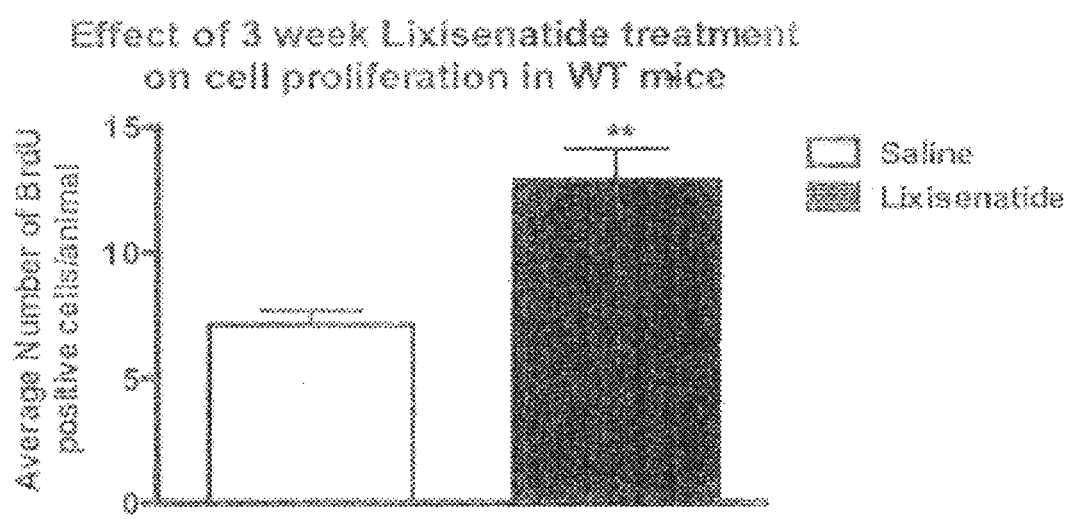
FIG. 5 shows histological analysis of chronic injection of lixisenatide ip. once-daily for 3 weeks (25 nmol/kg bw ip.). In a BrdU immuno-histological analysis, more new cells were found in the dentate gyrus brain area. Also, more young neurons were found (double cortin stain). Values are the mean±S.E.M. *=$p<0.05$, **=$p<0.01$.

The effects of chronic injection of lixisenatide i.p., exendin-4 i.p. and liraglutide i.p. for 3 weeks upon neuronal progenitor stem cell proliferation was investigated. An enhanced stem cell proliferation in the dentate gyrus was found (BrdU stain, FIGS. 4 and 5). Surprisingly, lixisenatide had significantly enhanced cell proliferation (*=p<0.05) when compared with exendin-4 or liraglutide, indicating that lixisenatide is more effective in the brain than exendin-4 and liraglutide when injected at the same dose.

In addition, the number of young neurons in the dentate gyrus was increased after lixisenatide injection when compared to liraglutide (double cortin stain, data not shown), indicating that the progenitor cells differentiate into neurons. This demonstrates that lixisenatide induces lasting improvements.

These effects of lixisenatide on stem cells (proliferation and differentiation) are an important aspect for brain repair, so these effects can provide a disease-modifying effect in neurodegenerative diseases, such as Alzheimer's disease, Parkinson's disease, and stroke.

Neuroprotective Effects of Lixisenatide in the Brain

In neuronal cell culture studies, lixisenatide has been tested to investigate if it has neuroprotective effects in cellular stress conditions. The toxic drug Methyl Glyoxal was used to reduce cell viability. Addition of lixisenatide showed neuroprotective effects in a dose-dependent manner (FIG. 6a), affording 100% protection at all doses with the lowest concentration of Methyl Glyoxal and maintaining protection even with the highest concentration of Methyl Glyoxal tested. A dose of 10 nM lixisenatide was sufficient in protecting cells from 1200 µM Methyl Glyoxal stress.

Figure 6A:
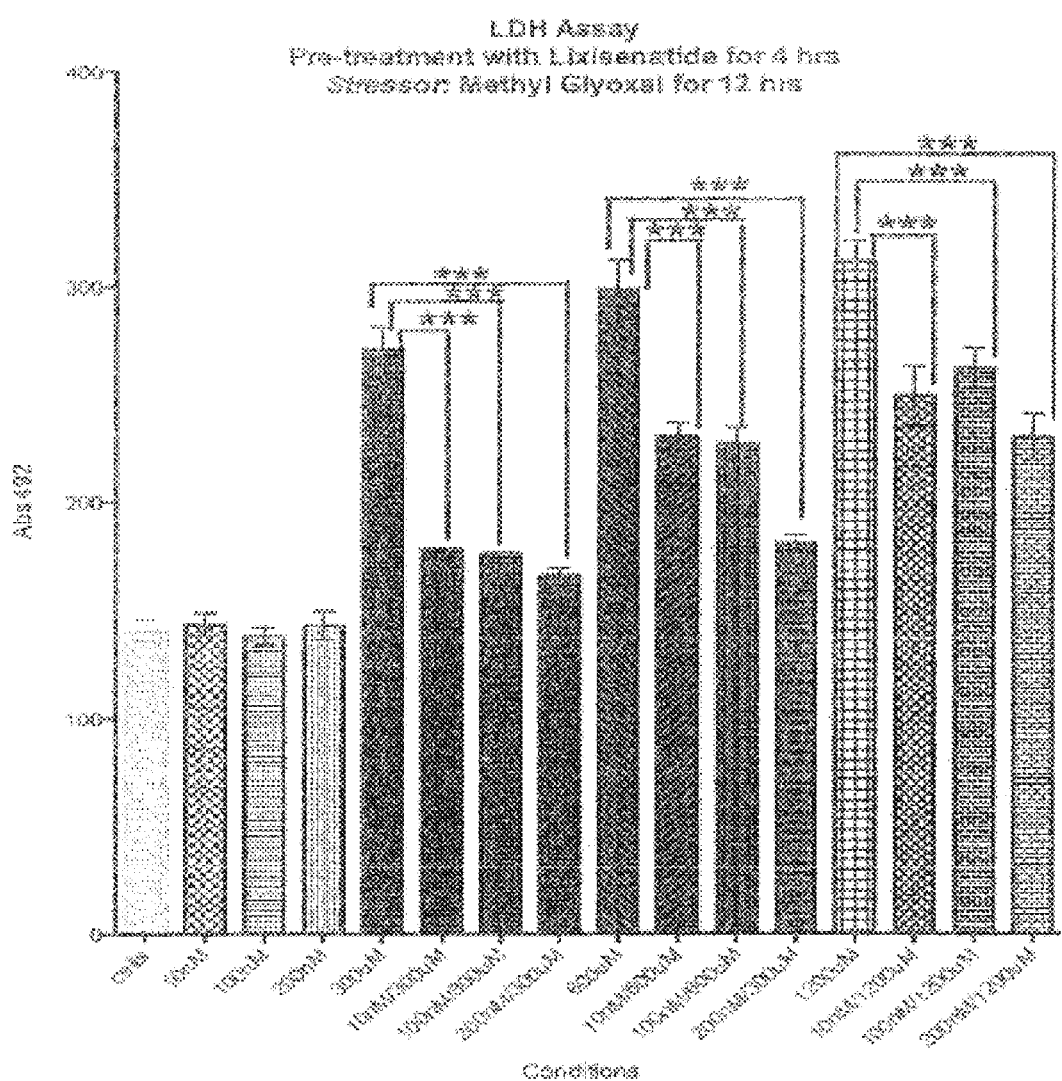
FIG. 6A shows LDH Assay. Pre-treatment of SH-SY5Y cells with lixisenatide followed by Methyl Glyoxal Stress. (***<0.0001). A dose of 10 nM lixisenatide was sufficient in protecting cells from 1200 μM Methyl Glyoxal stress.
Figure 6B:
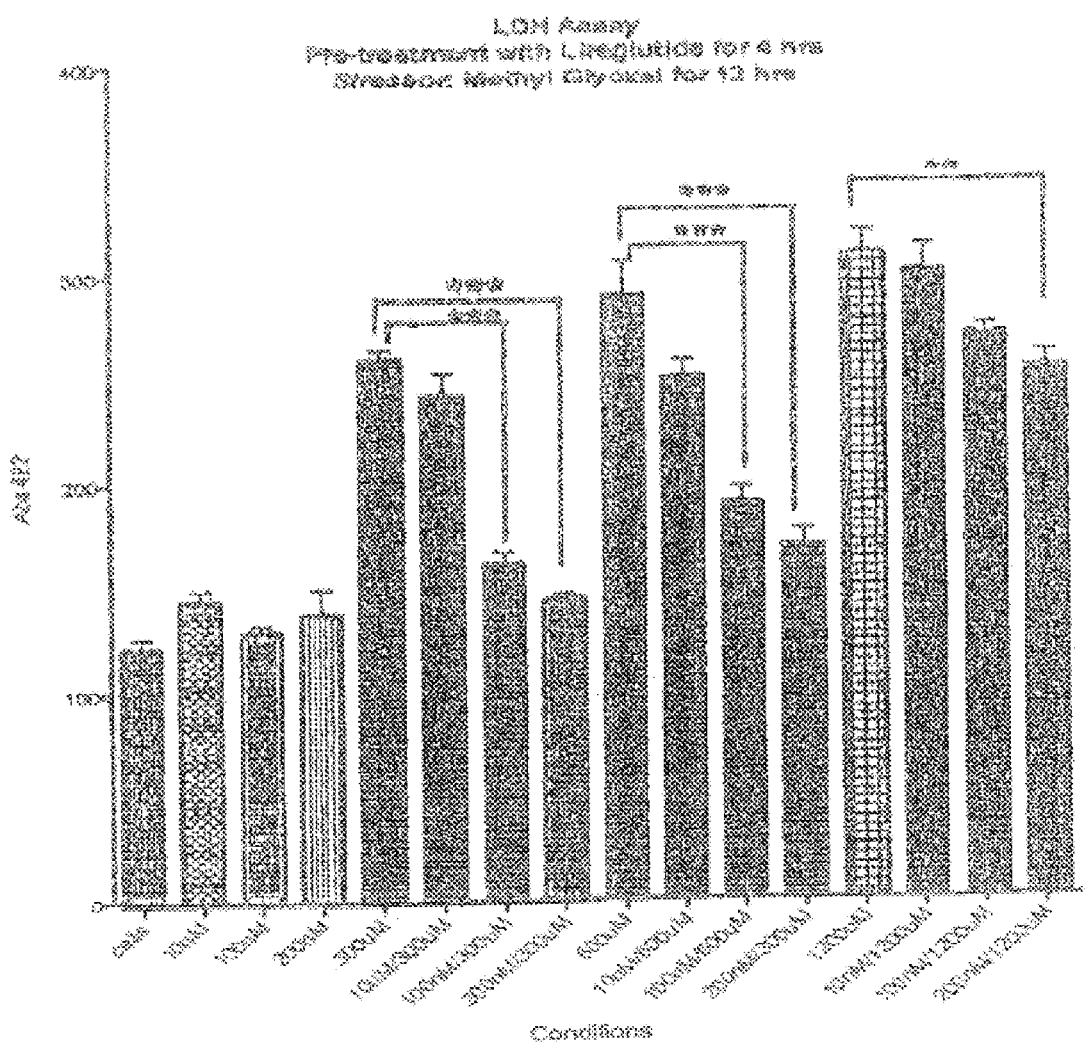
FIG. 6B shows LDH Assay. Pre-treatment of SH-SY5Y cells with liraglutide followed by Methyl Glyoxal Stress. (*$p<0.05$. $p<0.001$, *$p<0.0001$). A dose of 200 nM liraglutide was 10 sufficient in protecting cells from 1200 μM Methyl Glyoxal stress. The lower doses of 10 nM or 100 nM showed no effect.

In addition, lixisenatide showed superior protection compared with liraglutide. In FIG. 6b, it is shown that liraglutide was not able to protect cells at a does of 10 nM. A dose of 200 nM liraglutide was required in order to protect the cells from 1200 µM Methyl Glyoxal stress, the lower doses of 10 or 100 nM showed no effect.

Materials and Methods

Measurement of cAMP in the Brain

Animals

Female wild type (C57BL/6 background) mice were used, 5 per group. For cAMP measurement, mice were injected i.p. with 25 nmol/kg body weight (bw) liraglutide, lixisenatide or saline (0.9% w.v.) as control in two separate experiments. 30 min post injection mice brains were immediately removed and snap frozen.

Tissue Extraction of cAMP

Each brain was extracted using 0.1 M HCl. 10 ml of 0.1 M HCl per g of tissue was added. Samples were sonicated then centrifuged at 10,000 rpm for 15 min at 4° C. The supernatant was poured off and used directly for measurement by direct cAMP ELISA kit (Enzo Life Sciences). Dilutions were made using the 0.1 M HCl provided in the kit.

Immunohistochemistry

Animals were administered BrdU (180 mg/kg bw; i.p.) 18 h prior to being anaesthetized with pentobarbitone (0.3 ml; Euthanal, Bayer AG, Leverkusen, Germany) and perfused transcardially with PBS followed by 4% paraformaldehyde. The brains were removed and put into 30% sucrose in PBS overnight. Immunohistochemistry for BrdU or doublecortin (DCX) was performed on 45 µm free floating sections.

Endogenous peroxidase activity was quenched by incubation of sections in 3% hydrogen peroxide. Denaturation of DNA involved incubation in 2N HCl, followed by 0.1 M borax for 10 min. Sections were incubated in a primary antibody for BrdU (1:200, mouse monoclonal anti-BrdU, Sigma) or for DCX gout polyclonal anti-doublecortin (1:200, Santa Cruz, USA, sc-710) overnight at 4° C. Then secondary antibody (1:200, horse anti-mouse, Vector elite ABC kit, mouse, Vector laboratories) was applied. Sections were incubated in an avidin biotin enzyme reagent and incubated in Vector SG substrate chromogen (see Gengler et al. 2010) for details.

Microscopy

The sections were analysed using an Olympus CX 40 microscope, using stereological techniques. This involves starting the sectioning randomly and collecting every 5 m section throughout the granule cell layer (GCL) of the dentate gyrus (DG). Analysis was performed using a ×40 objective and representative images were taken using a 5.1 MPix digital camera. For each drug group, 4-6 mice brains were analysed. Between 8 and 12 sections were taken for each brain. The brain regions analysed ranged from −1.3 to −2.5 mm bregma. All positive cells in the DG were counted using ImageJ software (freeware of the NIH, http://rsbweb-.nih.govl/ij/). In the GCL, cells positive for BrdU or DCX were counted.

SH-SY5Y Cell Line

SH-SY5Y is a thrice-cloned human neuroblastoma cell line that was established in 1970 from a bone marrow biopsy of a metastatic neuroblastoma site in a four year-old female. These cells are dopamine beta hydroxylase active, acetyicholinergic, glutamatergic and adenosinergic. SH-SY5Y cells grow as a mixture of floating and adherent cells as well as form clusters of neuroblastic cells with multiple, short, fine cell processes. Retinoic acid and cholesterol treatment can force the cells to grow dendrites and differentiate.

Pre-Treatment of SH-SY5Y Cells with Lixisenatide or Liraglutide Followed by Methyl Glyoxal Stress SH-SY5Y cells were cultured in Dulbecco's minimum essential medium with F12 (1:1) and Glutamax supplemented with 10% heat inactivated (heated at 56° C. for 20 min) fetal bovine serum and penicillin and streptomycin, and incubated in a humidified, 5% $CO_2$, 37° C. incubator. Cells were trypsinized at 80% confluency and after counting cells by trypan blue exclusion method (Countess, Invitrogen), $2 \times 10^4$ cells were plated in Laminin coated 96-well plate (Nunc, Inc) at 95% cell viability. After 12 hours of cell attachment, cells were pre-treated with lixisenatide or liraglutide at different doses as at 10 nM, 100 nM and 200 nM, followed by the addition of stressor Methyl Glyoxal in the serum free media at concentrations 300 µM, 600 µM (and 1200 µM (FIGS. 6A and 6B). Data was analyzed by PRISM 5.0C (GraphPad Software, Inc.) and significance was defined as p values of <0.05 or smaller.

Effect of Lixisenatide or Liraglutide Pre-Treatment on Hydrogen Peroxide Stressed SH-SY5Y Cells Cells were pre-treated with 10 nM and 100 nM liraglutide or lixisenatide, followed by the addition of stressor hydrogen peroxide in the serum free media at concentrations 200 µM, 400 µM and 800 µM.

LDH Assay

Cell culture media were analysed using a sensitive lactatedehydrogenase (LDH) assay (by Sigma). The LDH assay provides a measure of the number of dead cells via total cytoplasmic LDH or by membrane integrity as a function of the amount of cytoplasmic LDH released into the medium. The measurement of released LDH is based on the reduction of NAD by the action of LDH. The resulting reduced NAD (NADH) is used in the stoichiometric conversion of a tetrazolium dye. The final colored compound is measured by colorimetry.

Summary

The data of the present example demonstrates that lixisenatide is suitable for the treatment or/and prevention of neurodegenerative diseases, such as Alzheimer's disease, Parkinson's disease, progressive supranuclear palsy, multiple system atrophy, Lewy body dementia, Parkinson's disease dementia or stroke. Furthermore, lixisenatide has superior properties compared to the GLP-1 analog liraglutide and to exendin-4, both of which are currently used as treatments for type 2 diabetes.

In particular, the data of the present example demonstrates that (a) surprisingly, lixisenatide can cross the blood brain barrier. The data of the present invention indicate that the transport is regulated, as the transport rate at high concentrations is limited to a maximum level. Furthermore, lixisenatide is taken up into the brain at a lower parenteral dose as compared with liraglutide.

(b) lixisenatide activates GLP-1 receptors in the brain and induces cAMP production. Surprisingly, lixisenatide produces higher levels of cAMP than liraglutide, demonstrating higher effectiveness at activating the GLP-1 receptor at the same dose.

(c) lixisenatide can induce proliferation of progenitor cells in the dentate gyrus. Compared with exendin-4 or with liraglutide, lixisenatide surprisingly provides enhanced effects when administered at the same dose. In neurodegenerative diseases, these effects can constitute a diseasemodifying effect (d) surprisingly, lixisenatide showed superior neuroprotective effects (against cellular stress) in the dentate gyrus when compared with liraglutide.

(e) surprisingly, a pre-treatment with a dose of 10 nM lixisenatide was sufficient in protecting SH-SY5Y neuroblastoma cells from 1200 µM Methyl Glyoxal stress. A dose of 200 nM liraglutide was necessary in protecting cells from 1200 µM Methyl Glyoxal stress, indicating that a lower dose of lixisenatide is sufficient to induce protection.

EXAMPLE 2

Post-Stress Treatment with Lixisenatide or Liraglutide after Methyl Glyoxal (MG) and Hydrogen Peroxide ($H_2O_2$) Treatment SHSY-5Y cells were seeded in 96 well plates and after 12 hours of serum starvation, were stressed with 600 µM and 1 mM of $H_2O_2$ and 1 mM and 2 mM of MG for 3 hrs. The cells were treated with 0, 1, 10, 50 and 100 nM of Lixisenatide and 0, 10, 50, 100 and 200 nM of Liraglutide. After 24 hrs 50 µL of XTT reagent was added and incubated for 8 hrs. The assay volume was 100 µL.

Figure 7A:
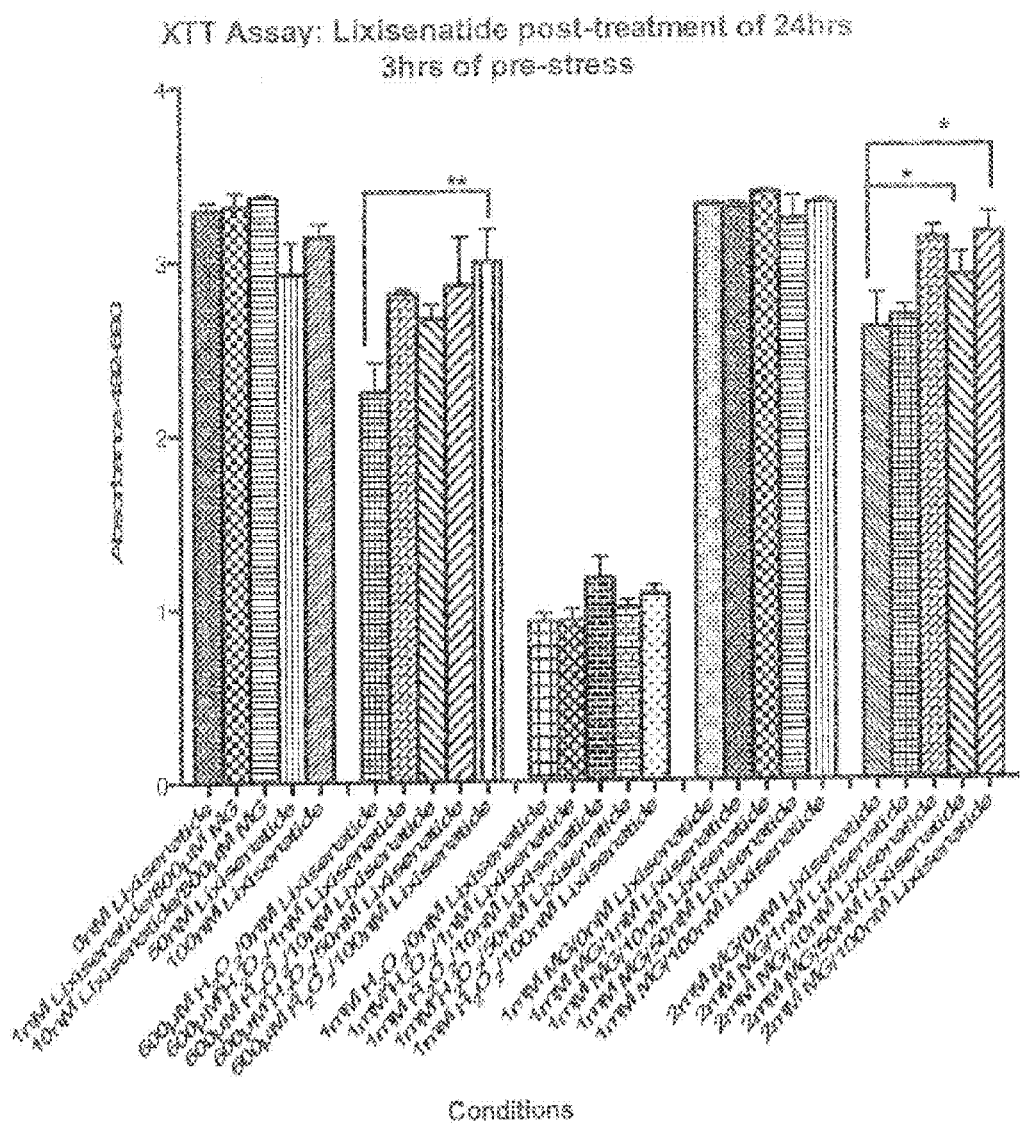
FIG. 7A shows post-stress treatment with Lixisenatide after Methyl Glyoxal (MG) and Hydrogen Peroxide ($H_2O_2$) treatment. The X-axis refers to various assay conditions and the Y-axis represents the absorbance. *=$p<0.05$, **=$p<0.01$.
Figure 7B:
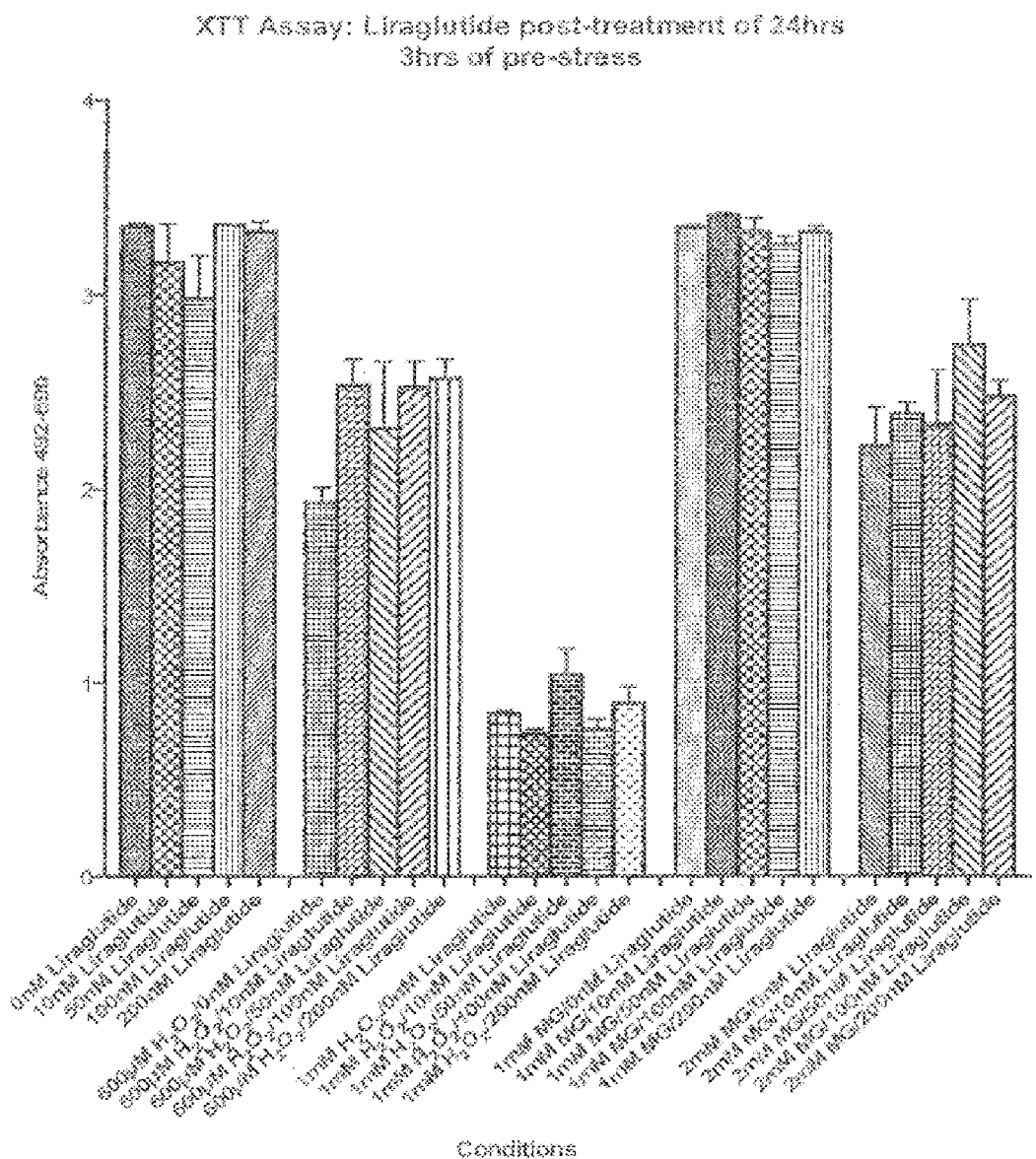
FIG. 7B shows post-stress treatment with Liraglutide after Methyl Glyoxal (MG) and Hydrogen Peroxide ($H_2O_2$) treatment. The X-axis refers to various assay conditions and the Y-axis represents the absorbance. *=$p<0.05$, **=$p<0.01$.

FIG. 7 demonstrates that the post-treatment with Lixisenatide significantly increased the number of surviving cells after stress with MG or $H_2O_2$ in a dose-dependent way (see in particular data obtained with 600 µM $H_2O_2$, and 2 mM MG in FIG. 7A). Liraglutide did not protect cells from the stress by MG or $H_2O_2$ (FIG. 7B).

Pre-Treatment with Lixisenatide or Liraglutide Followed by Methyl Glyoxal (MG) Stress SHSY-5Y cells were seeded in 96 well plates and after 12 hours of serum starvation and were treated with 0, 1, 10, 50 and 100 nM of Lixisenatide and 0, 10, 50, 100 and 200 nM of Liraglutide and Exendin-4 for 4 hrs, after being stressed with 400 µM and 600 µM of MG for 14 hrs. 50 µL of XTT reagent was added and plates incubated for 8 hrs.

Figure 8A:
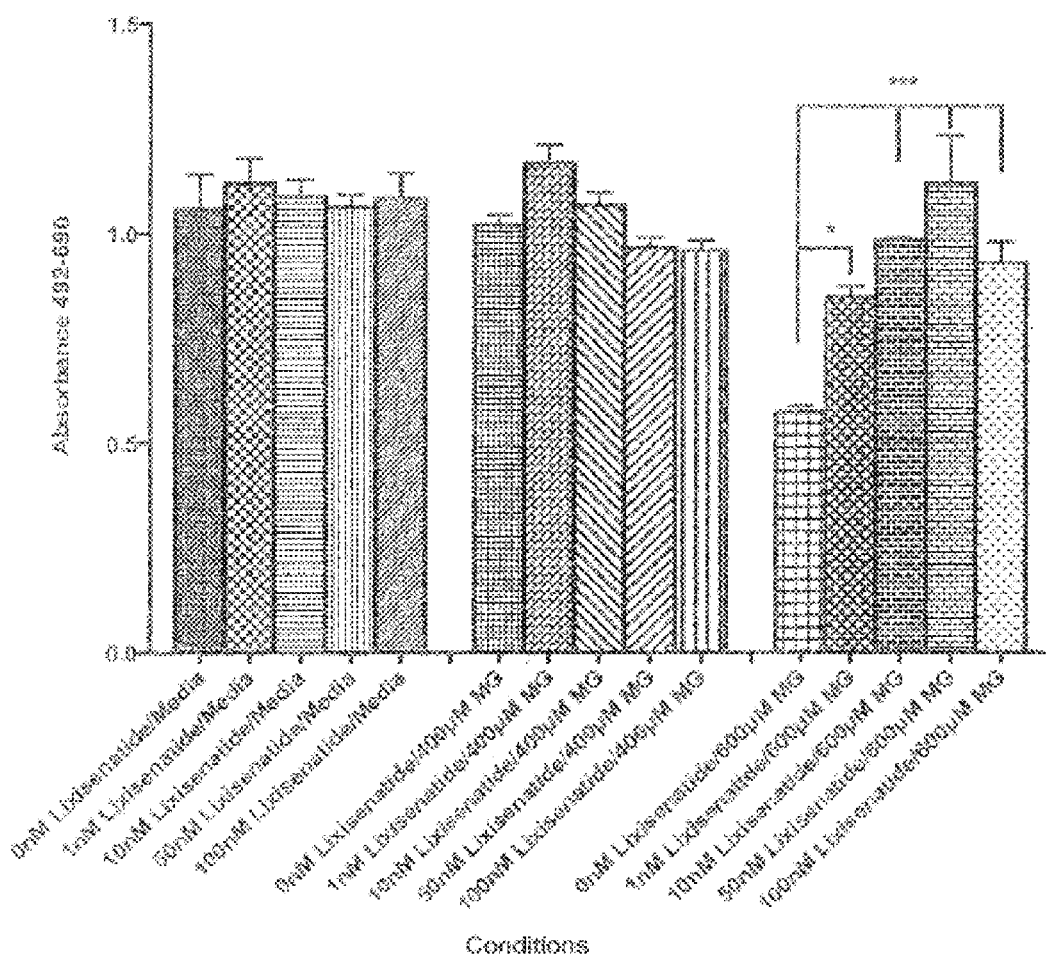
FIG. 8A shows pre-treatment effect of Lixisenatide followed by Methyl Glyoxal (MG) stress. The X-axis refers to various assay conditions and the Y-axis represents the absorbance. *=$p<0.05$, ***=$p<0.001$.
Figure 8B:
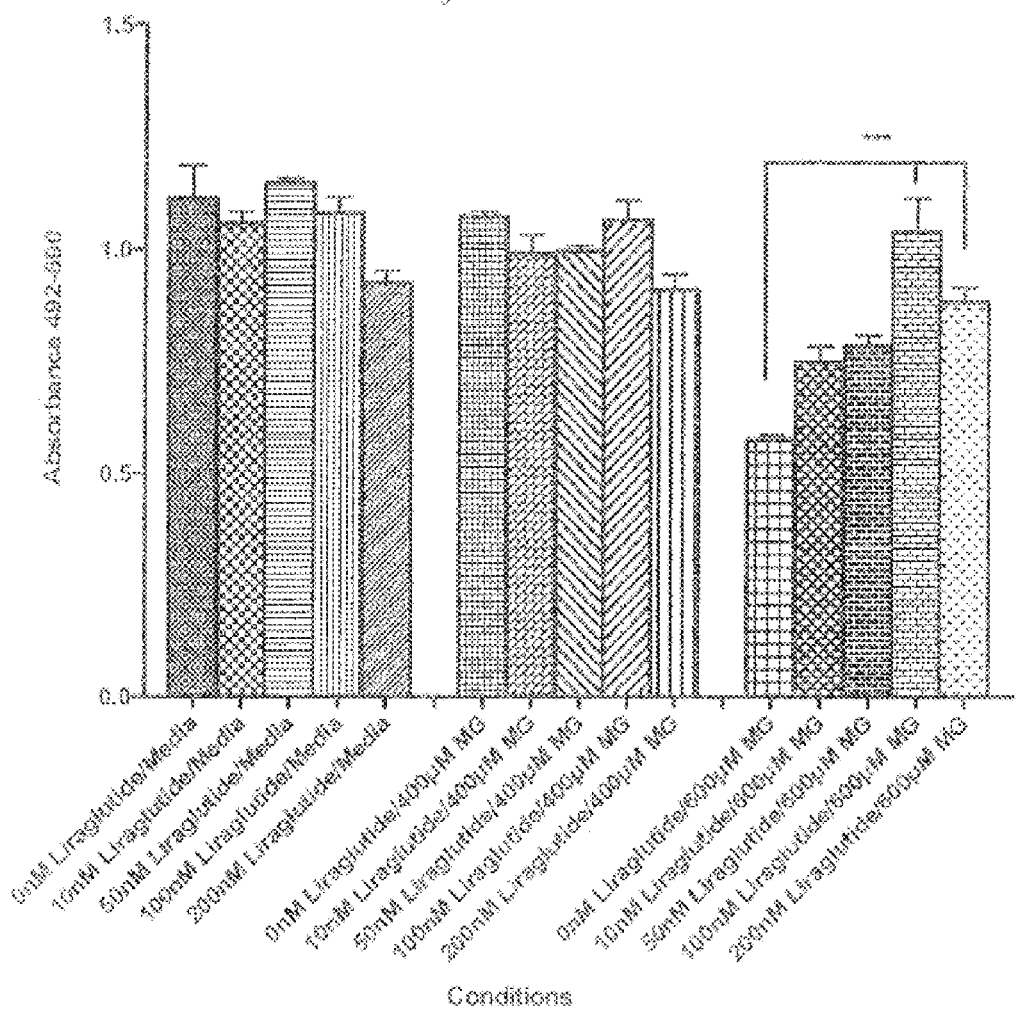
FIG. 8B shows pre-treatment effect of Liraglutide followed by Methyl Glyoxal (MG) stress. The X-axis refers to various assay conditions and the Y-axis represents the absorbance. *=$p<0.05$, ***=$p<0.001$.
Figure 8C:
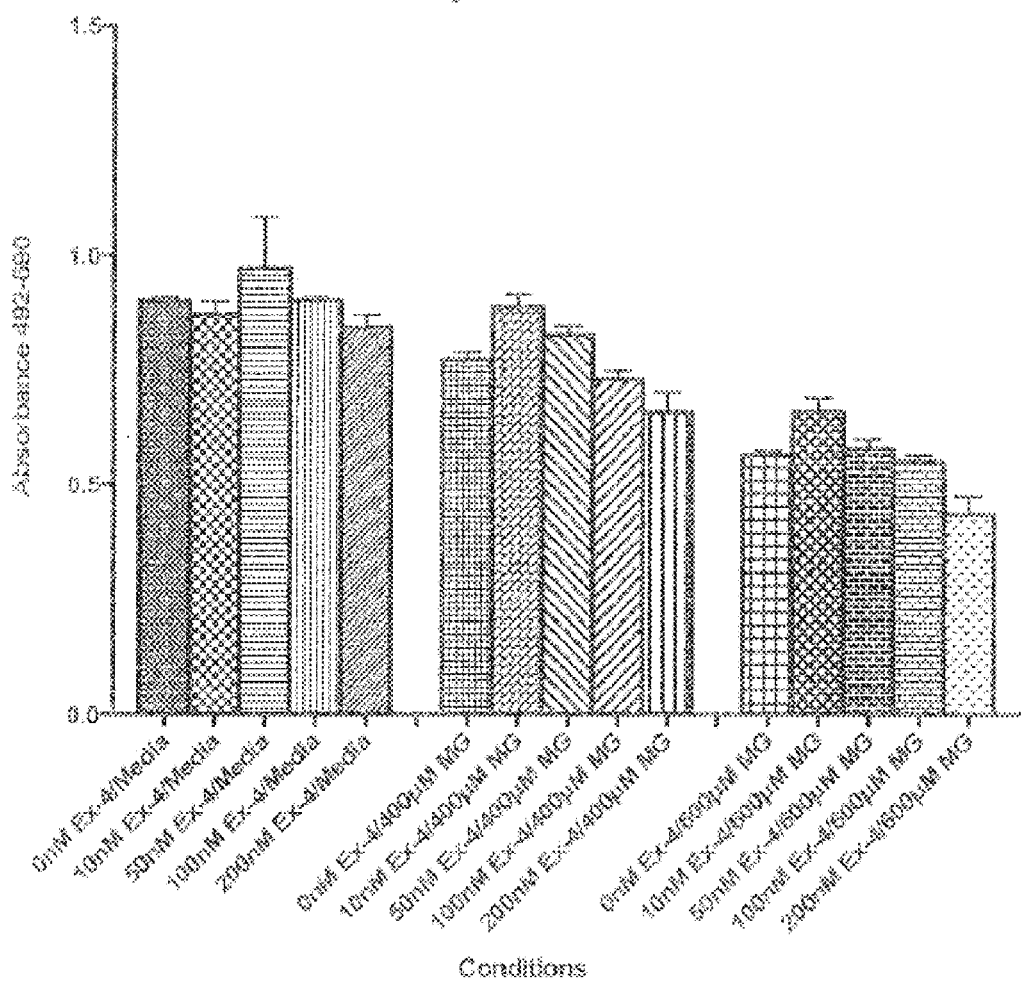
FIG. 8C shows pre-treatment effect of Exendin-4 followed by Methyl Glyoxal (MG) stress. The X-axis refers to various assay conditions and the Y-axis represents the absorbance. *=$p<0.05$, ***=$p<0.001$.

FIG. 8 demonstrates that the pre-treatment with Lixisenatide before stress with MG or $H_2O_2$ significantly increased the number of surviving cells in a dose-dependent way, starting with the lowest dose of 1 nM with best results at 50 nM (FIG. 8A). Liragutide also protected the cells, but only at a higher dose of 100 nM (FIG. 8B). Exendin-4 did not protect cells from the stress by MG or $H_2O_2$ (FIG. 8C).

Material and Methods

Pre-Treatment Assay with SHSY-5Y Cells Using Methyl Glyoxal as Stressor

1. SHSY-5Y cells were maintained in DMEM+F12 Glutamax media (Cat No. 313310, Invitrogen Inc.) with 10% FBS (Cat No. 10437, Invitrogen Inc.) and 1% Penn Strep (Cat No. 15070063, Invitrogen Inc.).
2. 80-90% confluent cultures were trypsinized using 0.25× trypsin EDTA solution and were seeded in 96 well plates (Cat No. 55301, Orange Scientific) which were previously coated with Laminin (L2020, Sigma) at a concentration of 1 µg/cm$^2$ for 2 hours at 37° C. in a $CO_2$ incubator and were washed 2 times with sterile double distilled water.
3. After 12-15 hours media was changed from 10% FBS containing to serum free media (SFM) for next 12 hours.
4. Cells were pre-treated with incretins for 4 hours, the assay was performed in 150 µl volume format of different concentrations and fresh SFM was added to the controls respectively, for 4 hrs.
5. The wells were washed with 1×HBSS and 150 µl of 600 µM Methyl Glyoxal (Cat No. M0252, Sigma) and SFM was added to the test wells and controls respectively for 12 hrs.
6. The supernatant was collected to perform the LDH assay and stored at −20° C.
7. 75 µl of XTT solution (Cat No. 11465015001, Roche Inc.) (Containing the coupling reagent) was added to the remaining cells and incubated at 37° C. for 4 hours. The assay is based on the ability of metabolic active cells to reduce the tetrazolium salt XTT to colored compounds which can be determined by absorbance measurement. An increased absorbance indicates an increased number of metabolic active cells.
8. Absorbance was obtained by measuring at 492 nm and 690 nm for each well and subtracting $A_{690}$ from $A_{492}$.
9. For the LDH (Cat No. G1780, Promega) assay the 50 µl of the supernatant was added to a 96 well plate along with 50 µl of the substrate and incubated in dark at room temperature for 60 minutes.
10. 50 µl of Stop solution was added and the absorbance measured at 490 nm.
11. The data for XTT and LDH assays was analyzed using Prism V.

Summary

The data of example 2 demonstrates that lixisenatide is suitable for the treatment or/and prevention of neurodegenerative diseases, such as Alzheimer's disease, Parkinson's disease, progressive supranuclear palsy, multiple system atrophy, Lewy body dementia, Parkinson's disease dementia or stroke. Furthermore, lixisenatide has superior properties compared to the GLP-1 analogs liraglutide and exenatide.

A pre-treatment with a dose of 10 nM lixisenatide was sufficient in protecting SH-SY5Y neuroblastoma cells from 600 µM Methyl Glyoxal stress. A dose of 100 nM-200 nM liraglutide was sufficient in protecting cells from 600 µM Methyl Glyoxal stress, indicating that a lower dose of lixisenatide is sufficient to induce protection. Lixisenatide is thus suitable for the prevention of the diseases as indicated above. These data are in line with the data obtained in Example 1 (FIGS. 6A and B), demonstrating that lixisenatide showed superior neuroprotective effects (against cellular stress) in SH-SY5Y neuroblastoma cells when compared with liraglutide.

Furthermore, a post-treatment with lixisenatide was sufficient in protecting SH-SY5Y neuroblastoma cells after from 2 mM Methyl Glyoxal stress or 1 mM $H_2O_2$ stress. In contrast, Liraglutide did not protect cells from the stress by MG or $H_2O_2$.

EXAMPLE 3

Treatment with the Glucagon-Like Peptide-1 Receptor (GLP-1R) Agonist Lixisenatide Protects Human Neuronal Cells Against Rotenone Toxicity In this Example, neuroprotection experiments in cellular models are described supporting the use of Lixisenatide in the treatment of Parkinson's disease, Parkinson's disease dementia, progressive supranuclear palsy, multiple system atrophy, and Lewy body dementia. The Example demonstrates that Lixisenatide could slow-down, arrest or reverse the progression of Parkinson's disease, Parkinson's disease dementia, progressive supranuclear palsy, multiple system atrophy, and Lewy body dementia by protecting the neurons vulnerable in this disease. These diseases are associated with loss of neurons utilizing dopamine as neurotransmitter.

The Example refers to in vitro cultures assays using a human cell line that is being dopaminergic in nature called Lund Human Mesencephalic neurons (LUHMES cells). These cells are described in Lotharius et al. (2002). Cultures from these cells were exposed in vitro to rotenone known to kill dopaminergic cells and to be associated with Parkinson's disease upon accidental or environmental exposure to humans. The association of rotenone with Parkinson's disease is described in Sherer et al., 2003 and Tanner et al., 2011. Rotenone can cause parkinsonism by killing dopamine-producing neurons and thereby experimentally reproducing the major features of the human Parkinson's disease.

Figure 9:
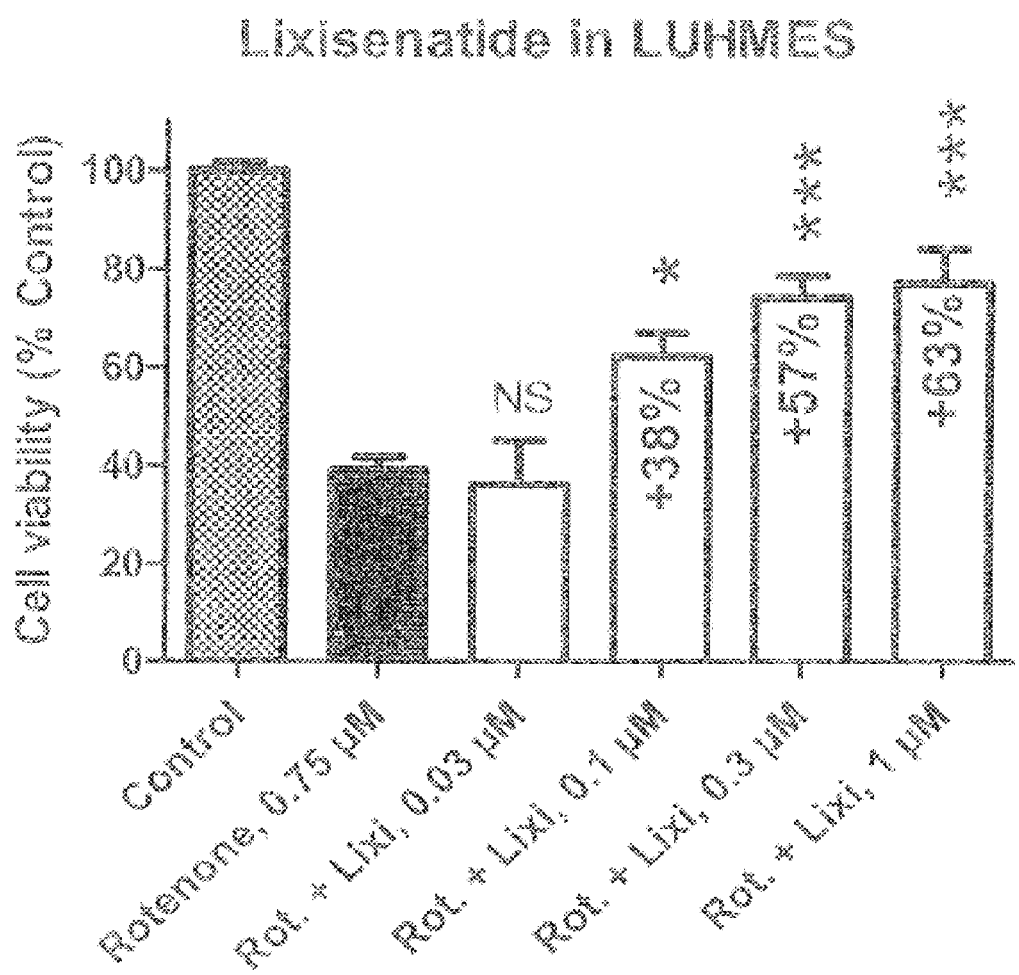
FIG. 9 shows neuroprotection of LUHMES cells (expressed as percentage reversal of the normalized cell viability decrease induced by rotenone exposure) in the presence of various concentrations of Lixisenatide. Rot.=rotenone. NS=not significant; *=$p<0.05$; ***=$p<0.001$.
Figure 11:
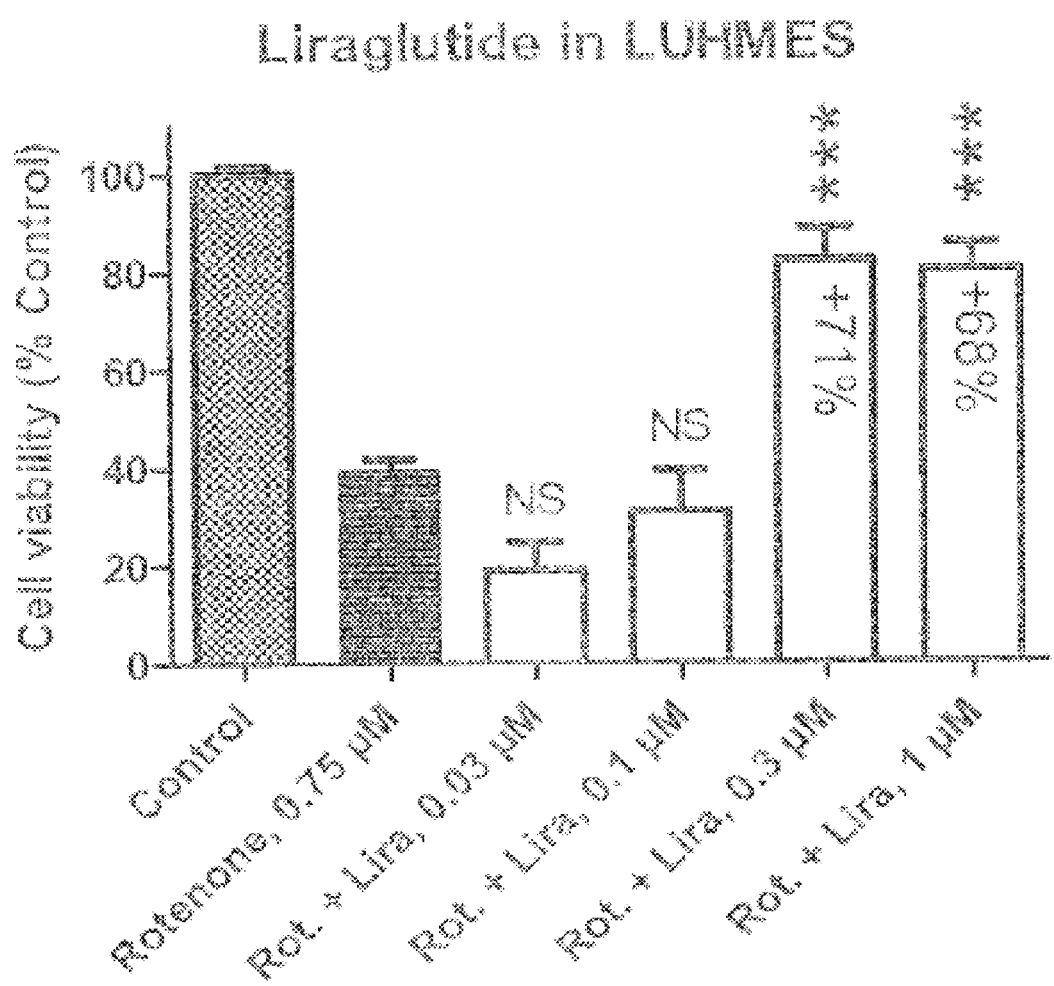
FIG. 11 shows neuroprotection of LUHMES cells (expressed as percentage reversal of the normalized cell viability decrease induced by rotenone exposure) in the presence of various concentrations of Liraglutide. Rot.=rotenone. NS=not significant; ***=$p<0.001$.

In the present Example, the glucagons-like peptide-1 receptor (GLP-1R) agonist Lixisenatide exhibits significant neuroprotective effects in LUHMES cells against neurodegeneration induced by rotenone (FIG. 9). Lixisenatide provides advantages compared with other GLP-1 receptor (GLP-1R) agonists. The neuroprotective effect of Lixisenatide against rotenone in LUHMES cells is significantly active at 3-fold lower concentrations than Liraglutide (FIGS. 9 and 11), a result comforting the unexpected superior activity effect of Lixisenatide seen previously in the Methyl Glyoxal model of Example 1.

Figure 10:
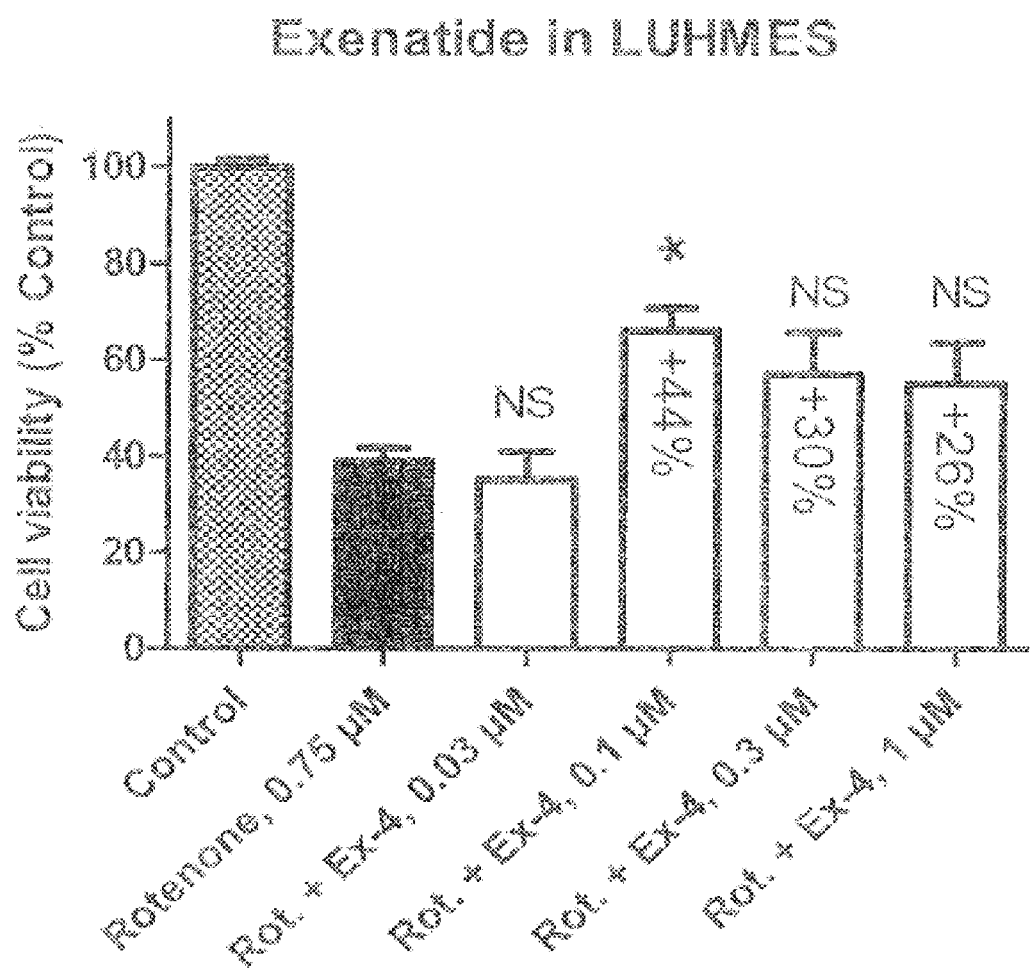
FIG. 10 shows neuroprotection of LUHMES cells (expressed as percentage reversal of the normalized cell viability decrease induced by rotenone exposure) in the presence of various concentrations of Exendin-4/Exenatide. Rot=rotenone. NS=not significant. *=$p<0.05$.

Exenatide does not induce an improved viability at a concentration of 0.3 µM or 1 µM. In contrast, Lixisenatide provides a significant improvement of viability at these concentrations (FIGS. 9 and 10).

Material and Methods

To assess neuroprotection against rotenone, LUHMES cells were grown at 37° C. in a humidified 95% air, 5% $CO_2$ atmosphere in standard cell-culture media. After 2 days culture in plastic flasks, differentiation medium containing growth factors was added and cells were incubated for another 2 days. Cells were dissociated and seeded into coated multi-well plates and fresh differentiation medium was added for another 4 days. On day 6 of differentiation, cells were treated with various concentrations of Lixisenatide, Exenatide (Exendin-4) or Liraglutide 1 hour before treatment with rotenone (0.75 µM). Neuroprotection was measured after 72 hrs. with a resazurin-based assay, an indicator of metabolically active cells generating a fluorescent product through cellular oxidation-reduction. The fluorescence produced is proportional to the number of viable cells in the cultures and thus measures the degree of protection of the neuronal LUHMES cells provided by the treatments. Data from n=12 measurements were compared following normalization of cell viability readings with respect to controls without rotenone. A one-way analysis of variance followed by a Dunnett's test was used for statistical comparisons between experimental groups. Values of p<0.05 were considered as significant and denoted in the graphs with asterisks as follows: *=p<0.05; =p<0.01; *=p<0.001; NS=not significant.

Neuroprotection was expressed as percent reversal of viability decrease induced by rotenone.

Summary

The data of example 3 demonstrates that lixisenatide is suitable for the treatment or/and prevention of neurodegenerative diseases, such as Parkinson's disease, progressive supranuclear palsy (PSP), multiple system atrophy (MSA), Lewy body dementia, Parkinson's disease dementia or stroke. Furthermore, lixisenatide has superior properties compared to the GLP-1 analog liraglutide and to exendin-4.

In the present Example, Lixisenatide exhibits significant neuroprotective effects in LUHMES cells against neurodegeneration induced by rotenone (FIG. 9). Lixisenated provides advantages compared with other GLP-1 receptor (GLP-1R) agonists. In rotenone treated LUHMES cells, Lixisenatide is significantly active at 3-fold lower concentrations than Liraglutide. At a concentration of 0.3 µM or 1 µM Exenatide, no significant effect could be observed. In contrast, Lixisenatide provides a dose-dependent improvement of viability at these concentrations.

EXAMPLE 4

The Effect of Lixisenatide in $APP_{SWE}/PS1_{\Delta E9}$ Transgenic Mice

To further demonstrate the interest of lixisenatide for the treatment of neurodegenerative diseases such as Alzheimer's Disease, in the present example, it is described the effect of lixisenatide treatment in transgenic mice bearing amyloid plaques in their brain. $APP_{swe}/PS1_{\Delta E9}$ transgenic mice are a well characterized model of Alzheimer's disease showing an amyloid brain pathology. Lixisenatide treatment (10 nmol/kg, i.p., daily) was initiated in 7-month old APP/PS1 transgenic mice at an age when amyloid plaques have already developed in the brain and lasted for 70 days.

Transgenic Animals $APP_{swe}/PS1_{\Delta E9}$ mice with a C57Bl/6 background were obtained from the Jackson lab (http://research.jax.org/repository/alzheimers.html). Heterozygous males were bred with wild-type C57/Bl6 females bought locally (Harlan, UK). Offspring were ear punched and genotyped using PCR with primers specific for the APP-sequence (Forward "GAATTCCGACATGACTCAGG, SEQ ID NO:4", Reverse: "GTTCTGCTGCATCTTGGACA, SEQ ID NO:5"). Mice not expressing the transgene were used as wild-type controls. Male animals were used in all studies. Animals were caged individually and maintained on a 12/12 light-dark cycle (lights on at 08h00, off at 20h00), in temperature-controlled room (T:21.5° C.±1). Food and water were available ad libitum. Animals were handled daily for two weeks prior to commencement of the study.

Treatment with Lixisenatide

Mice were 7 months of age when treatment began. At that time, mice already showed amyloid brain pathology. Mice were injected intraperitoneally (i.p.) once daily with Lixisenatide (10 nmol/kg body weight) or Saline (0.9% w/v) for 70 days. Experiments were licensed by the UK home office in accordance with the Animal (scientific procedures) Act of 1986.

Lixisenatide was supplied by Sanofi. Lyophylised peptide was reconstituted in Milli-Q water at a concentration of 1 mg/ml. Aliquots were stored in the freezer and reconstituted in 0.9% saline for injection.

Histological Preparation

Animals were perfused transcardially with PBS buffer followed by ice-cold 4% paraformaldehyde in PBS. Brains were removed and fixed in 4% paraformaldehyde for at least 24 h before being transferred to 30% sucrose solution overnight. Brains were then snap frozen using Envirofreez™ and coronal sections of 40-micron thickness were cut at a depth of −2 to −3 Bregma using a Leica cryostat. Sections were chosen according to stereological rules with the first section taken at random and every 6th section afterwards.

Using standard methods (see McClean et al. 2011 for details), beta amyloid was stained using rabbit polyclonal anti amyloid beta peptide (1:200, Invitrogen, UK, 71-5800), and dense core plaques were stained using congo red. Beta amyloid and congo red were analysed by taking 2 images (using a 10× objective) of cortex per section (with 7-10 sections per brain; n=6 for Lixisenatide 10 nmol/kg bw, n=12 for saline). All staining was visualized by Axio Scope 1 (Zeiss, Germany) and analyzed using a multi threshold plug-in with Image J (NIH, USA).

Results

Figure 12:
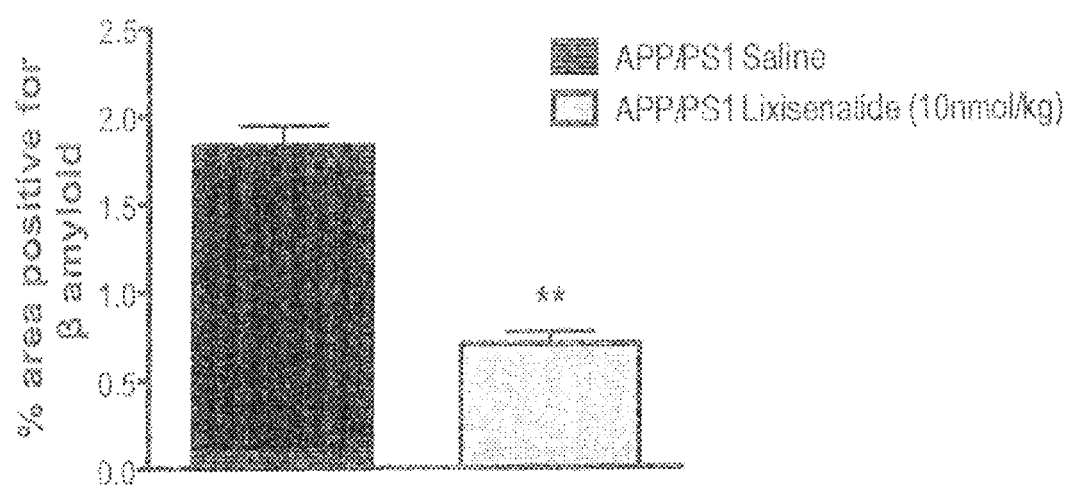
FIG. 12 shows Lixisenatide treatment reduces amyloid plaque load in the brain of Alzheimer's Disease transgenic mice, Lixisenatide treatment in 7-month old APP/PS1 transgenic mice for 70 days (10 nmol/kg, i.p., daily) reduces beta amyloid plaque load in the brain as quantified by beta amyloid immunohistochemistry and determination of the % area positive for 1 amyloid in cross sections of the brain cortex. Values are mean+/−SEM (**=$p<0.01$).

In $APP_{swe}/PS1_{\Delta Ee}$ transgenic mice already bearing amyloid brain pathology at initiation of treatment, lixisenatide treatment for 70 days lead to a reduction of beta amyloid plaque load as measured by beta amyloid immunoreactivity by 62% (p<0.0039; repeated measures t-test), compared with Saline-treated mice (FIG. 12).

Figure 13:
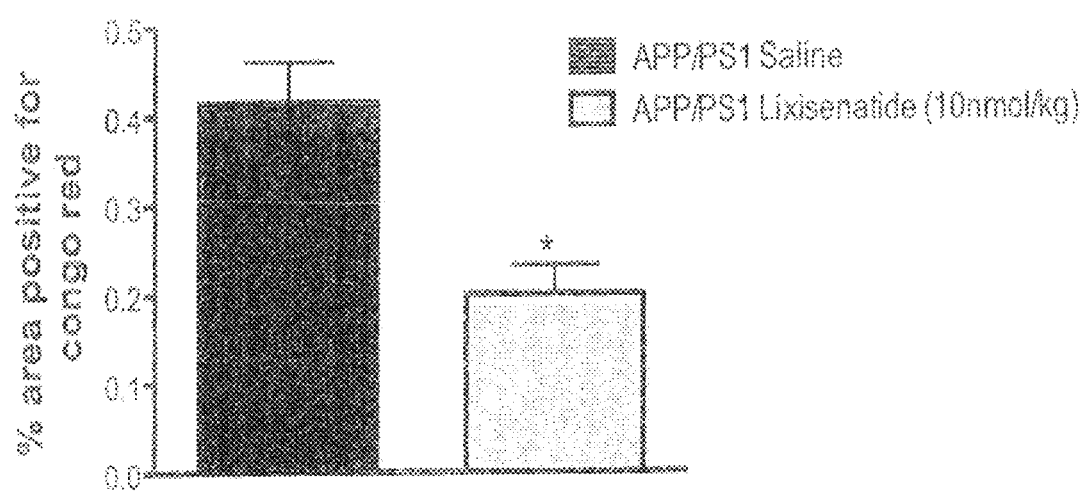
FIG. 13 shows Lixisenatide treatment reduces amyloid plaque load in the brain of Alzheimer's Disease transgenic mice. Lixisenatide treatment in 7-month old APP/PS1 transgenic mice (Alzheimer's disease model) for 70 days 10 nmol/kg, i.p., daily) reduces mature amyloid plaque load in the brain as quantified by histological staining with Congo red and determination of the % area positive for Congo red in cross sections of the brain cortex. Values are mean+/− SEM (*=p<0.05).

Similarly, lixisenatide treatment reduced dense core amyloid plaque load as quantified by Congo red histological staining by 52% (p=0.0419; repeated measures t-test) compared with respective Saline-treated APP/PS1 mice (FIG. 13).

The activity was observed at lower dose (10 nmol/kg) than previously described for liraglutide (25 nmolm/kg, McClean et al 2011).

Summary

These data using two independent techniques demonstrate that lixisenatide can reduce brain amyloid pathology in an animal model of Alzheimer's disease. The data demonstrates that lixisenatide is suitable for the treatment or/and prevention of neurodegenerative diseases, such as Alzheimer's disease by decreasing brain amyloid plaque pathology. Therefore in addition to its neuroprotective properties, lixisenatide can decrease pathological lesions such as amyloid plaques and represent therefore an attractive treatment or/and prevention for Alzheimer's disease. Furthermore, activity is achieved at dose lower than those previously described for the GLP-1 analog liraglutide as expected from the data of Example 1.

REFERENCES

1. Bertram L, Lill C M, and Tanzi R E, 2010. The Genetics of Alzheimer Disease: Back to the Future, *Neuron*, 68, 270-281.

2. Mancuso M, Orsucci D, LoGerfo A, Calsolaro V, Siciliano G, 2010, Clinical features and pathogenesis of Alzheimer's disease: involvement of mitochondria and mitochondrial DNA, *Adv Exp Med Biol.*, 685, 34-44.
3. Varadarajan S, Yatin S, Aksenova M, and Butterfield D A, 2000. Review: Alzheimer's Amyloid b-Peptide-Associated Free Radical Oxidative Stress and Neurotoxicity, *Journal of Structural Biology*, 130, 184-208.
4. Higginsa G C, Beart P M, Shin Y S, Chene M J, Cheunge N S and Nagley P, 2010, Oxidative Stress: Emerging Mitochondrial and Cellular Themes and Variations in Neuronal Injury, *Journal of Alzheimer's Disease*, 20, S453-8473.
5. Wollen K A, 2010, Alzheimer's disease: the pros and cons of pharmaceutical, nutritional, botanical, and stimulatory therapies, with a discussion of treatment strategies from the perspective of patients and practitioners, *Altern Med Rev.*, 15(3), 223-44.
6. Aderinwale O G, Ernst H W, Mousa S A, 2010, Current therapies and new strategies for the management of Alzheimer's disease, *Am J Alzheimers Dis Other Demen.*, 25(5), 414-24.
7. Kaduszkiewicz, H., Zimmermann T, Beck-Bomholdt H P, van den Bussche H (2005). Cholinesterase inhibitors for patients with Alzheimer's disease: systematic review of randomised clinical trials. BMJ 331: 321 doi: 10.1136/bmj.331.7512.321
8. Hölscher C, 2005, Development of Beta-Amyloid-induced neurodegeneration in Alzheimer's disease and novel neuroprotective strategies, *Reviews in Neuroscience*, 16, 181-212.
9. De Rosa, Garcia R, Braschi A A, Capsoni C. Maffei S, Berardi L, Cattaneo N, 2005, Intranasal administration of nerve growth factor (NGF) rescues recognition memory deficits in AD11 anti-NGF transgenic mice. Proc Natl Acad Sci., 102, 3811-3816.
10. Hölscher C, Li L, 2010, New roles for insulin-like hormones in neuronal signaling and protection: New hopes for novel treatments of Alzheimer's disease? *Neurobiology of Aging*, 31, 1495-1502.
11. Hölscher C, (2010b), The role of GLP-1 in neuronal activity and neurodegeneration, *Vitamins and hormones*, 84, 331-54.
12. McClean P L, Parthsarathy V, Faivre E, Hölscher C (2011): The diabetes drug Liraglutide prevents degenerative processes in a mouse model of Alzheimer's disease. J Neurosci., 31: 6587-6594.
13. Li H, Lee C H. Yoo K Y, Choi J H, Park O K, Yan B C. Byun K, Lee B, Hwang J K, Won M H (2010) Chronic treatment of exendin-4 affects cell proliferation and neuroblast differentiation in the adult mouse hippocampal dentate gyrus. Neurosci Lett 19: 1205-1219.
14. Li Y, Duffy K, Ottinger M, Ray B, Bailey J, Holloway H, Tweedie D, Perry T, Mattson M, Kapogiannis D, Sambamurti K. Lahiri D, Greig N (2010) GLP-1 Receptor Stimulation Reduces Amyloid-beta Peptide Accumulation and Cytotoxicity in Cellular and Animal Models of Alzheimer's Disease. J Alzheimers Dis 19:1205-1219.
15. Gandhi S, Wood N W (2005) Molecular pathogenesis of Parkinson's disease. Hum Mol Genet 14: 2749-2755.
16. Schapira A H (2001) Causes of neuronal death in Parkinson's disease. Adv Neurol 86: 155-162.
17. Perry T, Lahiri D K, Chen D, Zhou J, Shaw K T Y, Egan J M, Grieg N H (2002) A novel neurotrophic property of glucagon-like peptide 1: a promoter of nerve cell growth factor mediated differentiation on PC12 cells. J Pharmacol exp 300: 958-966.
18. Perry T A, Haughey N J, Mattson M P, Egan J M, Grieg N N (2002) Protection and reversal of excitotoxic neuronal damage by glucagon-like peptide-1 and exendin-4. J Pharmacol Exp Ther 302: 881-888.
19. Harkavyl A, Abuirmeileh A, Lever R, Kingsbury A E, Biggs C S. Whitton P S. (2008) Glucagon-like peptide I receptor stimulation reverses key deficits in distinct rodent models of Parkinson's disease. J Neuroinflamm 5: 19, 1-9.
20. Li A, Perry T A, Kindy M S, Harvey B K, Tweedie D, Holloway H W, Powers K, Shen H, Egan J M, Sambamurti K, Brossi A, Lahiri D K, Mattson M P, Hoffer B J, Wang Y, Greig N H (2009) GLP-1 receptor stimulation preserves primary cortical and dopaminergic neurons in cellular and rodent models of stroke and Parkinsons. PNAS 106: 4 1285-1290.
21. Martin B, Golden E, Carlson O D, Pistell P. Zhou J, Kim W, Frank B P, Thomas S, Chadwick A, Greig N H, Bates G P, Sathasivam K, Bernier M, Maudsley S, Mattson M P, Eagn J M (2009) Exendin-4 improves glycemic control, ameliorates brain and pancreatic pathologies and extends survival in a mouse model of Huntington's Disease. Diabetes 58: 2, 318-328.
22. Mattson M P (2007) Calcium and neurodegeneration. Aging Cell 6: 337-350
23. Lee C H, Yan B, Yo K Y, Choi J H, Kwon S H, Her S, Hwang I K, Cho J H, Kim Y M, Won M H (2011) Ischemia-induced changes in glucagon-like peptide-1 receptor and neuroprotective effect of its agonist exendin-4, in experimental transient cerebral ischemia. J Neurosc Res 89: 1103-1113.
24. Teramoto S, Miyamoto N, Yatomi K, Tanaka Y, Oishi H, Arai H, Hattori N, Urabe T (2011) Exendin-4, a glucagon-like peptide-1 receptor agonist, provides neuroprotection in mice transient focal cerebral ischemia. J Cerebr Blood Flow Metab 31:8, 1696-1705.
25. Nakagawa A, Satake H, Nakabayashi H (2004) Receptor gene expression of glucagon-like peptide-1, but not of glucose-dependent insulinotropic polypeptide, in rat nodose ganglion cells. Auton Neurosci 110: 36-43.
26. Perry T A, Holloway H, Weerasuriya A, Mouton P R, Duffy K, Mattison J A, Greig N H (2007) Evidence of GLP-1-mediated neuroprotection in an animal model of pyridoxine-induced peripheral sensory neuropathy. Exp Neurol 203: 2, 293-301.
27. During M H, Cao L, Zuzga D S, Francis J S, Fitzsimons H L, Jiao X, Bland R J, Klugmann M, Banks W A, Drucker D J, Haile C N (2003) Glucagon-like peptide-1 receptor is involved in learning and neuroprotection. Nat Med 9: 1173-1179.
28. Isacson R, Nielsen E, Dannaeus K, Bertilsson G, Patrine C, Zachrisson O, Wikström L (2009) The glucagon-like peptide 1 receptor agonist exendin-4 improves reference memory performance and decreases immobility in the forced swim test. Eur J Pharmacol 10: 650, 249-55.
29. Himeno T, Kamiya H, Naruse K, Harada N, Ozaki N, Seino Y, Shibata T, Kondo M, Kato J, Okawa T, Fukami A, Hamada Y, Inagaki N, Drucker D J, Oiso Y, Nakamura J (2011) Beneficial effects of exendin-4 on experimental polyneuropathy in diabetic mice. Diabetes 60:2397-2406.
30. Porter D W, Kerr B D, Flatt P R, Hölscher C, Gault V A (2010) Four weeks administration of Liraglutide improves memory and learning as well as glycemic control in mice with high fat dietary-induced obesity and insulin resistance. Diab Obes Metab 12: 891-899, 2010.

31. Doyle M E, Egan J M., Mechanisms of action of glucagon-like peptide 1 in the pancreas. Pharmacol Ther. 2007 March; 113(3):546-93. Epub 2006 Dec. 28.
32. Host (1999), Curr. Med. Chem 6: 1005
33. Nauck et al. (1997) Exp Clin Endocrinol Diabetes 105: 187
34. Lopez-Delgado et al. (1998) Endocrinology 139:2811.
35. McClean P L, Gault V A, Harriott P, Hölscher C, 2010, Glucagon-like peptide-1 analogues enhance synaptic plasticity in the brain: A link between diabetes and Alzheimer's disease, *European Journal of Pharmacology*, 630, 158-162.
36. Kastin A J, Akerstrom V, Pan W, 2001, Interactions of Glucagon-like peptide (GLP-1) with blood brain barrier, *Journal of Molecular Neuroscience*, 18(2), 7-14.
37. Perry T and Greig N, 2003, The glucagon-like peptides: a double-edged therapeutic sword? *Trends in Pharmacological Sciences*, 24, 377-383.
38. Li H, Lee C H, Yoo K Y, Choi J H, Park O K, Yan B C. Byun K, Lee B, Hwang J K, Won M H (2010) Chronic treatment of exendin-4 affects cell proliferation and neuroblast differentiation in the adult mouse hippocampal dentate gyrus. Neurosci Lett 19: 1205-1219.
39. Hamilton A., S. Patterson, D. Porter, V. A. Gault and C. Hölscher (2011): Novel GLP-1 mimetics developed to treat type 2 diabetes promote progenitor cell proliferation in the brain. J Neurosci Res, 89:481-489.
40. Gengler S, McClean P. McCurtin R, Gault V. Holscher C (2012) Val(8)GLP-1 rescues synaptic plasticity and reduces dense core plaques in APP/PS1 mice. Neurobiol Aging 33:265-276.
41. Sherer, T. B. Kim, J.-H, Betarbet, R. and Greenamyre, J. T., Subcutaneous Rotenone Exposure Causes Highly Selective Dopaminergic Degeneration and α-Synuclein Aggregation, 2003, *Experimental Neurology*, 179: 9-16.
42. Lotharius, J., Barg, S., Wiekop, P., Lundberg. C., Raymon, H. K., and Brundin, P., Effect of Mutant α-Synuclein on Dopamine Homeostasis in a New Human Mesencephalic Cell Line, 2002, *Journal of Biological Chemistry*, 277: 38884-38894.
43. Lotharius, J. Falsig, J., van Beek, J., Payne, S., Dringen, R., Brundin, P., and Leist, M., Progressive Degeneration of Human Mesencephalic Neuron-Derived Cells Triggered by Dopamine-Dependent Oxidative Stress Is Dependent on the Mixed-Lineage Kinase Pathway, 2005, *Journal of Neuroscience*, 25: 6329-6342.
44. Tanner, C. M., Kamel, F., Ross, G. W. Hoppin, J. A., Goldman, S. M., Korell, M., Marras, C., Bhudhikanok, G. S., Kasten, M., Chade, A. R. Comyns, K., Richards, M. B., Meng, C., Priestley, B., Fernandez. H. H., Cambi, F., Umbach, D. M., Blair, A., Sandier, D. P., and Langston, J. W., Rotenone, Paraquat, and Parkinson's Disease, 2011, *Environmental Health Perspectives*, 119: 866-872.
45. Kim, S., Moon, M. and Park, S., Exendin-4 protects dopaminergic neurons by inhibition of microglial activation and matrix metalloproteinase-3 expression in an animal model of Parkinson's disease, 2009, J. Endocrinology, 202: 431-439.
46. Dubois B. et al. Revising the definition of Alzheimer's disease: a new lexicon. *Lancet Neurol.* 2010; 9:1118-27.

The invention claimed is:

1. A method for treating Parkinson's disease in a patient in need thereof, comprising
administering to said patient a therapeutically effective amount of a pharmaceutical composition comprising desPro$^{36}$Exendin-4(1-39)-Lys$_6$-NH$_2$ ("lixisenatide") or a pharmaceutically acceptable salt thereof, and
optionally a pharmaceutically acceptable carrier, adjuvant, auxiliary substance or a combination thereof.

2. The method according to claim 1, wherein the lixisenatide or pharmaceutically acceptable salt thereof is administered parenterally.

3. The method according to claim 1, wherein the lixisenatide or pharmaceutically acceptable salt thereof is administered in a daily dose of 10 μg to 20 μg.

4. The method according to claim 1, wherein the Parkinson's disease is associated with neuronal loss.

5. The method of claim 4, wherein the neuronal loss is a loss of dopaminergic neurons.

6. The method of claim 4, wherein the neuronal loss is a neuronal loss in the substantia nigra resulting in a lack of dopamine.

7. The method according to claim 1, wherein the Parkinson's disease is associated with cognitive impairment.

8. The method according to claim 1, wherein the Parkinson's disease is an early-stage Parkinson's disease.

9. The method according to claim 1, wherein the progression of the Parkinson's disease is slowed down.

10. The method according to claim 1, wherein the Parkinson's disease is associated with oxidative stress, inflammatory response, apoptosis, neuronal loss, or a combination thereof.

11. The method according to claim 2, wherein the lixisenatide or pharmaceutically acceptable salt thereof is administered by subcutaneous injection.

12. The method according to claim 2, wherein the lixisenatide or pharmaceutically acceptable salt thereof is administered by intramuscular injection.

13. The method according to claim 1, wherein the lixisenatide or pharmaceutically acceptable salt thereof is administered in a daily dose of 1 μg to 50 μg.

14. The method according to claim 1, wherein the lixisenatide or pharmaceutically acceptable salt thereof is administered in a daily dose of 5 μg to 40 μg.

15. The method according to claim 1, wherein the lixisenatide or pharmaceutically acceptable salt thereof is administered in a daily dose of 10 μg to 30 μg.

16. The method according to claim 1, wherein the lixisenatide or pharmaceutically acceptable salt thereof is administered in a daily dose of 10 μg to 15 μg.

17. The method according to claim 1, wherein the lixisenatide or pharmaceutically acceptable salt thereof is administered in a daily dose of 15 μg to 20 μg.

* * * * *